(12) United States Patent
Thayumanavan et al.

(10) Patent No.: US 12,215,078 B2
(45) Date of Patent: Feb. 4, 2025

(54) COMPOSITIONS AND METHODS FOR PROTEIN LABELING, MODIFICATION, ANALYSIS, AND TARGETED DELIVERY

(71) Applicant: University of Massachusetts, Boston, MA (US)

(72) Inventors: Sankaran Thayumanavan, Amherst, MA (US); Richard W. Vachet, Belchertown, MA (US); Jiaming Zhuang, Amherst, MA (US); Bo Zhao, Sunderland, MA (US)

(73) Assignee: University of Massachusetts, Boston, MA (US)

( * ) Notice: Subject to any disclaimer, the term of this patent is extended or adjusted under 35 U.S.C. 154(b) by 857 days.

(21) Appl. No.: 17/254,433

(22) PCT Filed: Jun. 28, 2019

(86) PCT No.: PCT/US2019/039697
§ 371 (c)(1),
(2) Date: Dec. 21, 2020

(87) PCT Pub. No.: WO2020/006340
PCT Pub. Date: Jan. 2, 2020

(65) Prior Publication Data
US 2021/0380635 A1  Dec. 9, 2021

Related U.S. Application Data

(60) Provisional application No. 62/823,447, filed on Mar. 25, 2019, provisional application No. 62/691,248, filed on Jun. 28, 2018.

(51) Int. Cl.
| | |
|---|---|
| *C07C 69/736* | (2006.01) |
| *A61K 47/54* | (2017.01) |
| *C07C 69/593* | (2006.01) |
| *C07C 229/30* | (2006.01) |
| *C07C 229/34* | (2006.01) |
| *C07C 235/28* | (2006.01) |
| *C07C 271/28* | (2006.01) |
| *C07C 311/53* | (2006.01) |
| *C07C 323/54* | (2006.01) |
| *C07D 213/20* | (2006.01) |
| *C07D 213/74* | (2006.01) |
| *C07K 1/13* | (2006.01) |

(52) U.S. Cl.
CPC ............ *C07C 69/736* (2013.01); *A61K 47/54* (2017.08); *C07C 69/593* (2013.01); *C07C 229/30* (2013.01); *C07C 229/34* (2013.01); *C07C 235/28* (2013.01); *C07C 271/28* (2013.01); *C07C 311/53* (2013.01); *C07C 323/54* (2013.01); *C07D 213/20* (2013.01); *C07D 213/74* (2013.01); *C07K 1/13* (2013.01)

(58) Field of Classification Search
CPC ...... C07K 1/13; A61K 47/54; A61K 47/6803; C07C 69/593
See application file for complete search history.

(56) References Cited

U.S. PATENT DOCUMENTS

| | | | |
|---|---|---|---|
| 2012/0016095 A1* | 1/2012 | Saito ...................... | C07C 67/31 526/309 |
| 2021/0380635 A1* | 12/2021 | Thayumanavan ...... | A61P 35/00 |

OTHER PUBLICATIONS

Bischoff et al., Amino acids: Chemistry, functionality and selected non-enzymatic post-translational modifications, Journal of Proteomics, 75 (2012) 2275-2296, Publication Date: Feb. 22, 2012 (Year: 2012).*
Zhuang et al., A programmable chemical switch based on triggerable Michael acceptors, Chem. Sci., 2020, 11, 2103-2111 (Year: 2020).*
Dorwald F. A. Side Reactions in Organic Synthesis, 2005, Wiley: VCH, Weinheim p. IX of Preface p. 1-15. (Year: 2005).*
Krishnan et al., Design of Reversible, Cysteine-Targeted Michael Acceptors Guided by Kinetic and Computational Analysis, J. Am. Chem. Soc. 136, 12624-12630, Publication Date: Aug. 25, 2014 (Year: 2014).*
Shannon et al., Covalent protein modification: the current landscape of residue-specific electrophiles, Current Opinion in Chemistry Biology, 24: 18-26, Publication Date: Nov. 11, 2014 (Year: 2014).*
Furman et al., A Genetically Encoded aza-Michael Acceptor for Covalent Cross-Linking of Protein—Receptor Complexes, J. Am. Chem. Soc. 136, 8411-8417, Publication Date: May 20, 2014 (Year: 2014).*
Lin et al., Organocatalytic Asymmetric C-S Bond Formation: Synthesis of a-Methylene-b-mercapto Esters with Simple Alkyl Thiols, Adv. Synth. Catal. 2011, 353, 3301-3306, Publication Date: Dec. 8, 2011 (Year: 2011).*

* cited by examiner

*Primary Examiner* — Peter J Reddig
*Assistant Examiner* — Cheng Lu
(74) *Attorney, Agent, or Firm* — Milstein Zhang & Wu LLC

(57) ABSTRACT

The invention relates to chemically reactive and/or biologically active compounds, reagents and compositions thereof. More particularly, the invention provides novel reagents that are useful in chemical synthesis, functionalization, delivery, probing and/or analytical measurements of small molecule drugs, proteins, antibodies and other biomolecules. The invention provides novel biologically active agents useful as diagnostics or therapeutics, and related composition and methods of uses thereof.

8 Claims, 38 Drawing Sheets
Specification includes a Sequence Listing.

SEQUENCE LISTING

```
<160> NUMBER OF SEQ ID NOS: 10

<210> SEQ ID NO 1
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Leu Ile Val Thr Gln Thr Met Lys Gly Leu Asp Ile Gln Lys Val Ala
1               5                   10                  15

Gly Thr Trp Tyr Ser Leu Ala Met Ala Ala Ser Asp Ile Ser Leu Leu
            20                  25                  30

Asp Ala Gln Ser Ala Pro Leu Arg Val Tyr Val Glu Glu Leu Lys Pro
        35                  40                  45

Thr Pro Glu Gly Asp Leu Glu Ile Leu Leu Gln Lys Trp Glu Asn Gly
    50                  55                  60
```

```
Glu Cys Ala Gln Lys Lys Ile Ile Ala Glu Lys Thr Lys Ile Pro Ala
 65                  70                  75                  80

Val Phe Lys Ile Asp Ala Leu Asn Glu Asn Lys Val Leu Val Leu Asp
                 85                  90                  95

Thr Asp Tyr Lys Lys Tyr Leu Leu Phe Cys Met Glu Asn Ser Ala Glu
            100                 105                 110

Pro Glu Gln Ser Leu Ala Cys Gln Cys Leu Val Arg Thr Pro Glu Ala
        115                 120                 125

Asp Asp Glu Ala Leu Glu Lys Phe Asp Lys Ala Leu Lys Ala Leu Pro
    130                 135                 140

Met His Ile Arg Leu Ser Phe Asn Pro Thr Gln Leu Glu Glu Gln Cys
145                 150                 155                 160

His Ile

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggtggtggtg gttgtggtgg tggtggt                                              27

<210> SEQ ID NO 3
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (5)..(18)
<223> OTHER INFORMATION: Intrachain disulfide bond

<400> SEQUENCE: 3

Tyr Leu Leu Phe Cys Met Glu Asn Ser Ala Glu Pro Glu Gln Ser Leu
 1               5                  10                  15

Ala Cys Gln Cys Leu Val Arg
             20

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Asp Ala Leu Asn Glu Asn Lys Val Leu Val Leu Asp Thr Asp Tyr
 1               5                  10                  15

Lys

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 5

Lys Ile Ile Ala Glu Lys
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Asp Lys Ala Leu Lys
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Leu Val Leu Asp Thr Asp Tyr Lys Lys
1               5                   10

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Lys Ile Pro Ala Val Phe Phe
1               5

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Tyr Val Glu Glu Leu Lys Pro Thr Pro Glu Gly Asp Leu Glu Ile
1               5                   10                  15

Leu Leu Gln Lys
            20

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Ala Arg Arg His Pro Tyr Phe Leu
1               5
```

COMPOSITIONS AND METHODS FOR PROTEIN LABELING, MODIFICATION, ANALYSIS, AND TARGETED DELIVERY

PRIORITY CLAIMS AND RELATED PATENT APPLICATIONS

This application is the U.S. national phase of and claims priority to PCT/US19/39697, filed Jun. 28, 2019, which claims the benefit of priority to U.S. Provisional Application Ser. Nos. 62/691,248, filed on Jun. 28, 2018, and 62/823,447, filed Mar. 25, 2019, the entire content of each of which is incorporated herein by reference.

STATEMENT REGARDING FEDERALLY FUNDED RESEARCH OR DEVELOPMENT

This invention was made with government support under Grant Nos. CHE-1307118 awarded by the National Science Foundation and 2R01GM075092-13 and CA-169140 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jun. 18, 2024, is named UOMA-054US_SL.txt and is 4,306 bytes in size.

TECHNICAL FIELD OF THE INVENTION

The invention relates to chemically reactive and/or biologically active compounds, reagents and compositions thereof. More particularly, the invention relates to novel molecular scaffolds and compounds that are useful in chemical synthesis, functionalization, delivery, probing and/or analytical measurements of small molecule drugs, proteins, antibodies and other biomolecules. The invention further provides novel biologically active probes and agents that are useful in analytical, diagnostic or therapeutic applications, as well as related compositions and methods of uses thereof.

BACKGROUND OF THE INVENTION

Click chemistry as a modular synthetic approach to new molecular entities has had a profound impact on a variety of applications, ranging from drug discovery to drug delivery, and from biorthogonal chemistry to proteomics and functional materials. (Kolb, et al. 2001 *Angew. Chem. Int. Ed.* 40, 2004-2021; Thirumurugan, et al. 2013 *Chem. Rev.* 113, 4905-4979; Kolb 2003 *Drug Discovery Today* 8, 1128-1137; Sletten, et al. 2009 *Angew. Chem. Int. Ed.* 48, 6974-6998; McKay, et al. 2014 *Chem Biol.* 21, 1075-1101; Patterson, et al. 2014 *ACS Chem. Biol.* 9, 592-605; Lee, et al. 2014 *ACS Nano* 8, 2048-2063; Lallana, et al. 2012 *Pharm Res.* 29, 1-34; Wright, et al. 2016 *Nat. Prod. Rep.* 33, 681-708; Yang, et al. 2017 *Nat. Commun.* 8, 2240-2249; DeForest, et al. 2011 *Nat. Chem.* 3, 925-931; Xi, et al. 2014 *Adv. Funct. Mater.* 24, 2572-2590.)

Represented by azide-alkyne cycloaddition, Diels-Alder, thiol-based, SuFEx, and carbonyl click reactions, current interests mainly focus on the bond formation process. (Tornoe, et al. 2002 *J. Org. Chem.* 67, 3057-3064; Rostovtsev, et al. 2002 *Angew. Chem. Int. Ed.* 41, 2596-2599; Dommetholt, et al. 2014 *Nat. Commun.* 5, 5378; Agard, et al. 2004 *J. Am. Chem. Soc.* 126, 15046-15047; Song, et al. 2008 *Angew. Chem. Int. Ed.* 47, 2832-2835; Blackman, et al. 2008 *J. Am. Chem. Soc.* 130, 13518-13519; Durmaz, et al. 2007 *Macromolecules* 40, 191-198; Truong, et al. 2013 *Angew. Chem. Int. Ed.* 52, 4132-4136; Nair, et al. 2014 *Chem. Mater.* 26, 724-744; Killops, et al. 2008 *J Am. Chem. Soc.* 130, 5062-5064; Dong, et al. 2014 *Angew. Chem. Int. Ed* 0.53, 9430-9448; Kölmel, et al. 2017 *Chem. Rev.* 117, 10358-10376.)

The importance of click-type chemistry for bond cleavage remains underexplored. The debonding click chemistry can be categorized into two approaches: (i) click-to-release strategies, where an efficient bond formation reaction triggers specific cleavage of masked functionalities; and (ii) reversible click or 'declick' reactions, where the click product can be chemically, thermally or mechanically reversed to liberate the original starting materials. The ability to incorporate various releasable functionalities with the click-to-release approach has impacted antibody drug conjugates (ADCs) and neuromodulator delivery strategies. (Azoulay, et al. 2006 *Bioorg. Med. Chem. Lett.* 16, 3147-3149; Versteengen, et al. 2013 *Angew. Chem. Int. Ed.* 52, 14112-14116; Carlson, et al. 2018 *J. Am. Chem. Soc.* 140, 3603-3612; Bernard, et al. 2017 *Angew. Chem. In. t Ed.* 56, 15612-15616; Jiménez-Moreno, et al. 2017 *Angew. Chem. Int. Ed.* 56, 243-247; Krupička, et al. 2017 *Angew. Chem. In.t Ed.* 56. 7745-7749; Wiggins, et al. 2011 *J. Am. Chem. Soc.* 133, 7180-7189; Fan, et al. 2016 *Angew. Chem. Int. Ed.* 55, 14046-14050; Diehl, et al. 2016 *Nat. Chem.* 8, 968-973; Sun, et al. 2017 *Nat. Chem.* 9, 817-823; Rossin, et al. 2018 *Nat. Commun.* 9, 1484; Zheng, et al. 2018 *Nat. Chem.* 10, 787-794; Ji, et al. 2016 *Angew. Chem. Int. Ed.* 55, 15846-15851; Zhao, et al. 2016 *Angew. Chem. Int. Ed.* 55, 14638-14642.)

Similarly, the reversibility and dynamic nature of the declick reaction offer unique access to manipulating new materials properties. (Sung, et al. 2018 *J. Am. Chem. Soc.* 140, 5000-5003; Li, et al. 2014 *J. Am. Chem. Soc.* 136, 15925-15928; Billiet, et al. 2014 *Nat. Chem.* 6, 815-821; Discekici, et al. 2018 *J. Am. Chem. Soc.* 140, 5009-5013.)

Click reactions that concurrently capture the triggered uncaging of functional groups with the click-to-release, and triggered reversibility akin to declick reactions are not currently available.

Moreover, programmable kinetics and customizable reversibility of these reactions, which opens up new avenues in applications in variety of areas from chemistry to materials science to biology, are rarely achieved.

Current analytical techniques are inadequate for delivering easy to obtain, high-resolution structural information for proteins, particularly their higher order structure and interactions with other proteins and ligands. Commonly used methods such as size-exclusion chromatography (SEC), circular dichroism (CD), analytical ultracentrifugation, dye binding assays, and FTIR only show structural averages, and are unable to detect subtle structural changes or protein interaction sites. High-resolution methods such as X-ray crystallography and NMR are unsuitable for routine analyses as they are time consuming, require considerable expertise, and are typically not compatible with certain protein samples.

Hydrogen-deuterium exchange mass spectrometry (HDX-MS) is an emerging technology with potential to overcome these limitations, but high back exchange and the need for specialized training and expensive equipment have limited the widespread adoption of this technique. In addition, HDX-MS is unable to be used directly with many protein samples and requires sample dilutions or solvent exchange.

Novel covalent labeling reagents that can react with a wider range of amino acid side chains and are resistant to hydrolysis are urgently needed. While protein-labeling reagents are available, real time evaluation of the extent of label is not yet achieved. Also desirable is enhancement of protein stability due to presence of modification and improved efficacy when released as pristine protein when encountering the therapeutic target. However, the current reversible modification methods are very limited and mainly based on cysteine and lysine modifications.

One of the critical factors in developing antibody-drug conjugation is the linker that links the antibody and drug molecules and release the active drug form in response to disease environment with appropriate kinetics. A specially designed linker is required each given drug. Re-design of linkers are required for drugs with different functionalities.

Thus, improved molecular scaffolds and analytical techniques are desired for synthesis, functionalization, delivery, probing and/or analytical measurements of small molecule drugs, proteins, antibodies and other biomolecules for use in a wide range of applications.

SUMMARY OF THE INVENTION

The invention provides novel molecular scaffolds and reagents that are useful in chemical functionalization and/or for probing and analytical measurements of proteins and other biomolecules. The invention also provides for novel probing agents and techniques and for improved delivery of biologically active agents that are useful as diagnostics or therapeutics. The invention additionally provides compositions and methods of use of the above.

In particular, a core feature of the invention is a chemical switch, an activated Michael acceptor bearing a good leaving group at the α-position, that undergoes a click-to-release process where promoted nucleophilic addition occurs to generate a less activated Michael acceptor (bonding) and release the leaving group (debonding). The less activated Michael acceptor can be further reversed to liberate original nucleophiles akin to a declick reaction by a second nucleophile.

The molecular switch disclosed herein offers the ability to bond and debond with a variety of functional groups with tunable kinetics, selectivity and reversibility. Within a very small molecular volume of the switch, five locations are engineered to achieve programmable click-to-release kinetics and customizable declick reversibility. The profound impact of this chemistry is partially demonstrated by its applications for (i) chemo-selective, reversible, quantifiable protein modifications; (ii) universal uncaging strategy for functionality recovery; and (iii) orthogonally manipulatable functional hydrogels.

The α-substituted methacrylate based molecular scaffold can be made to react with a broad spectrum of nucleophiles with high fidelity, controllable selectivity and kinetic tunability. The molecular scaffold is useful for a variety of applications, including protein covalent labeling and simultaneous quantification of the covalent labeling, reversible protein modification and traceless delivery, and as a general-purpose linker for diverse types of releasable antibody-drug conjugations.

In one aspect, the invention generally relates to a compound of the structural formula:

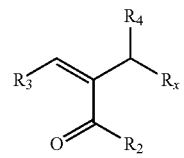

(I)

wherein
$R_x$ is a leaving group, optionally represented by $X-R_1$, wherein X is NH, $NR_6$ or O and each of $R_1$ and $R_6$ independently comprises one or more carbon atoms directly bound to X via single or double C—X bond(s);

$R_2$ is $OR_5$ or $NHR_5$, wherein $R_5$ is H, a linear or branched $C_1$-$C_{24}$ alkyl, an alkyl chain bearing anionic and cationic hydrophilic functional groups, or an alkyl chain bearing a charge neutral group optionally selected from oligoethyleneglycols;

$R_3$ is H or comprises an aliphatic or aromatic group, and optionally $R_3$ comprises a polypeptide; and $R_4$ is H or an alkyl group.

In another aspect, the invention generally relates to a reaction product formed by reacting a disclosed compound of a nucleophile.

In yet another aspect, the invention generally relates to a compound of the structural formula:

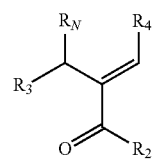

(II)

wherein
$R_2$ is $OR_5$ or $NHR_5$, wherein $R_5$ is H, a linear or branched $C_1$-$C_{24}$ alkyl, an alkyl chain bearing anionic and cationic hydrophilic functional groups, or an alkyl chain bearing a charge neutral group optionally selected from oligoethyleneglycols;

$R_3$ is H or comprises an aliphatic or aromatic group, and optionally $R_3$ comprises a polypeptide;

$R_4$ is H or an alkyl group; and $R_N$ comprises a polypeptide sequence.

In yet another aspect, the invention generally relates to a method for performing a chemical transformation, comprising shifting between two or more molecular states as represented by (I), (II) and (III):

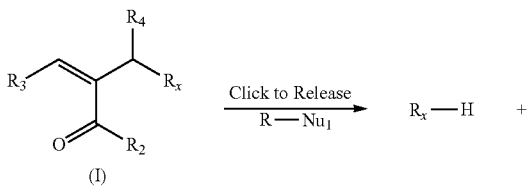

-continued $$\underset{(II)}{\overset{R}{\underset{R_3}{\bigvee}}\overset{Nu_1}{\underset{O}{\bigvee}}\overset{R_4}{\underset{R_2}{\bigvee}}} \xrightarrow{\text{Click to Release}}_{R'—Nu_2}$$

$$\underset{(III)}{\overset{R_3}{\underset{O}{\bigvee}}\overset{R_4}{\underset{R_2}{\bigvee}}\overset{Nu_2—R'}{\underset{}{}}} + R—Nu_1$$

wherein each of molecular entities of (I), (II) and (III) is a stable compound, $R_x$ is a leaving group, optionally represented by X—$R_1$, wherein X is NH, $NR_6$ or O and each of $R_1$ and $R_6$ independently comprises one or more carbon atoms directly bound to X via single or double C—X bond(s);

$R_2$ is $OR_5$ or $NHR_5$, wherein $R_5$ is H, a linear or branched $C_1$-$C_{24}$ alkyl, an alkyl chain bearing anionic and cationic hydrophilic functional groups, or an alkyl chain bearing a charge neutral group optionally selected from oligoethyleneglycols;

$R_3$ is H or comprises an aliphatic or aromatic group, and optionally $R_3$ comprises a polypeptide;

$R_4$ is H or an alkyl group;

$Nu_1$ is a first nucleophilic group capable of undergoing click chemistry with (I) to form (II) while releasing $R_x$, and $Nu_2$ is a second nucleophilic group capable of undergoing click chemistry with (II) to form (III) while releasing R-$Nu_1$, each of R and R' comprises an aliphatic or aromatic group, and optionally R comprises a polypeptide.

In yet another aspect, the invention generally relates to a method for covalently labeling a protein, comprising reacting a protein with a compound disclosed herein to form a covalent bond therebetween.

In yet another aspect, the invention generally relates to a method for covalently labeling an antibody or antibody fragment, comprising reacting an antibody or antibody fragment with a compound disclosed herein to form a covalent bond therebetween.

In yet another aspect, the invention generally relates to a covalently labeled protein, antibody or antibody fragment produced by a method disclosed herein.

In yet another aspect, the invention generally relates to a method for labeling a protein, comprising: providing a protein of formula (IV) comprising a nucleophilic group (Nu) at a point of desired labeling:

R-Nu; (IV)

reacting the protein (IV) with a compound of formula (V) having both a label and a reporter group:

$$\underset{(V)}{\overset{O}{\underset{R_3}{\bigvee}}\overset{}{\underset{R_4}{\bigvee}}\overset{Reporter}{\underset{O}{\bigvee}}\overset{}{\underset{Y}{\bigvee}}\overset{L}{\underset{Label}{\bigvee}}}$$

wherein $R_3$ is H or an aliphatic or aromatic group;

$R_4$ is H or an alkyl group;

Y is O or $NR_5$, wherein $R_5$ is H or a $C_1$-$C_{12}$ alkyl;

L is a linking group, and the reaction results in releasing of the reporter and formation of a labeled protein of formula (VI)

$$\underset{(VI)}{\overset{R}{\underset{R_3}{\bigvee}}\overset{Nu}{\underset{O}{\bigvee}}\overset{R_4}{\underset{Y}{\bigvee}}\overset{L}{\underset{Label}{\bigvee}}} + \text{Reporter};$$

and detecting a signal of the reporter and/or the presence of the label to analyze or quantify the protein.

In yet another aspect, the invention generally relates to a method for analyzing a higher order structure of proteins, comprising: reacting a reference protein with a molecular scaffold disclosed herein under a set of conditions to form a covalently labeled reference protein; reacting a target protein with the molecular scaffold under the set of conditions to form a covalently labeled target protein; and analyzing the covalently labeled target protein and the covalently labeled reference protein, wherein the reference protein and the target protein have identical primary structures.

In yet another aspect, the invention generally relates to an antibody-drug conjugate of formula (VII):

$$\underset{(VII)}{\overset{Dtg}{\underset{R_3}{\bigvee}}\overset{Nu}{\underset{O}{\bigvee}}\overset{R_4}{\underset{Y}{\bigvee}}\overset{L}{\underset{Antibody}{\bigvee}}}$$

wherein

"Drug" is a biologically active payload;

"Antibody" is an antibody or antibody fragment;

$R_3$ is H, an aliphatic or aromatic group;

$R_4$ is H or an alkyl group;

Y is O or $NR_5$, wherein $R_5$ is H or alkyl; and

L is a linking group.

In yet another aspect, the invention generally relates to a method for releasing a protein, comprising reacting an antibody-drug conjugate disclosed herein with a nucleophilic reagent.

In yet another aspect, the invention generally relates to a polymer comprising a monomer unit having a pendent group of formula (VIII):

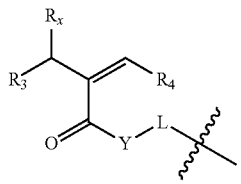

(VIII)

wherein
$R_x$ is a leaving group;
$R_3$ is H, an aliphatic or aromatic group;
$R_4$ is H or an alkyl group;
Y is O or $NR_5$, wherein $R_5$ is H or alkyl; and
L is a linking group.

In yet another aspect, the invention generally relates to a method for releasing a drug, comprising reacting a polymer disclosed herein with a nucleophilic reagent.

In yet another aspect, the invention generally relates to a method for preparing a polymer or a hydrogel composition, comprising: reacting

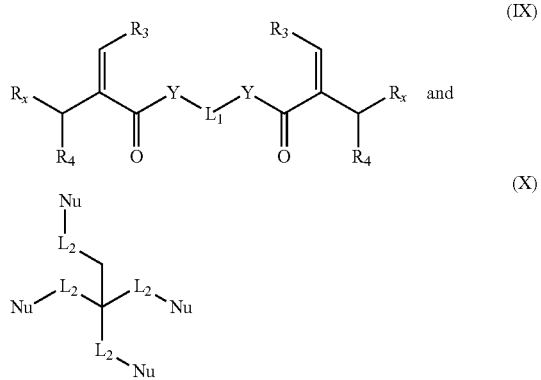

under conditions to form a polymer therebetween, wherein
$R_x$ is a leaving group;
$R_3$ is H, an aliphatic or aromatic group;
$R_4$ is H or an alkyl group;
Nu is a nucleophilic group;
Y is O or $NR_5$, wherein $R_5$ is H or alkyl; and
$L_1$ and $L_2$ are linking groups.

In yet another aspect, the invention generally relates to a hydrogel composition, comprising a three-dimensional polymer network disclosed herein and one or more payload materials enclosed therein.

In yet another aspect, the invention generally relates to a device or implant comprising a hydrogel composition disclosed herein.

In yet another aspect, the invention generally relates to a pharmaceutical composition comprising a compound, an antibody-drug-conjugate, a polymer-drug conjugate or a hydrogel disclosed herein, a pharmaceutically acceptable excipient, carrier, or diluent.

In yet another aspect, the invention generally relates to a method for treating a disease or condition, comprising administering to a subject in need thereof a therapeutically effective amount of a pharmaceutical composition disclosed herein.

In yet another aspect, the invention generally relates to a protein labeling kit comprising a compound disclosed herein.

DEFINITIONS

Figure 1:
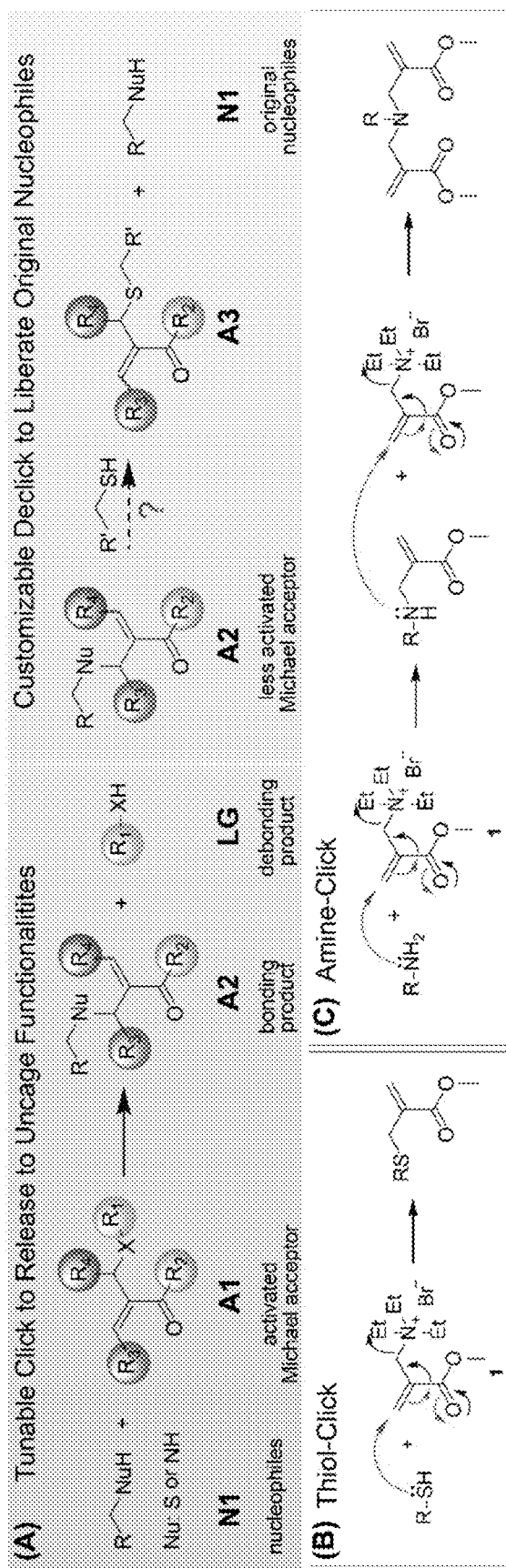
FIG. 1. Clickable chemical switch for bonding and debonding. (A) Schematic presentation of click-to-release as a universal strategy for uncaging of functional groups (left) and declick of corresponding click-to-release product, the reversibility of which can be structurally customized (right). (B) Proposed thiol-based click-to-release. (C) Proposed amine-based click-to-release.

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

Definitions of specific functional groups and chemical terms are described in more detail below. When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, the term "aliphatic" refers to a group or moiety that is not aromatic. An aliphatic group or moiety may be cyclic or non-cyclic, un-saturated or saturated, linear or branched.

As used herein, the term "alkyl" refers to a straight or branched hydrocarbon chain radical consisting solely of carbon and hydrogen atoms, containing no unsaturation, having from one to ten carbon atoms (e.g., $C_{1-10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, "alkyl" can be a $C_{1-6}$ alkyl group. In some embodiments, alkyl groups have 1 to 10, 1 to 8, 1 to 6, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, $-Si(R^a)_3$, $-OR^a$, $-SR^a$, $-OC(O)-R^a$, $-N(R^a)_2$, $-C(O)R$, $-C(O)OR^a$, $-OC(O)N(R^a)_2$, $-C(O)N(R^a)_2$, $-N(R^a)C(O)OR^a$, $-N(R^a)C(O)R^a$, $-N(R^a)C(O)N(R^a)_2$, $-N(R^a)C(NR^a)N(R^a)_2$, $-N(R^a)S(O)_tN(R^a)_2$ (where t is 1 or 2), $-P(=O)(R^a)(R^a)$, or $-O-P(=O)(OR^a)_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. In a non-limiting embodiment, a substituted alkyl can be selected from fluoromethyl, difluoromethyl, trifluoromethyl, 2-fluoroethyl, 3-fluoropropyl, hydroxymethyl, 2-hydroxyethyl, 3-hydroxypropyl, benzyl, and phenethyl.

As used herein, the term "alkoxy" refers to the group —O-alkyl, including from 1 to 10 carbon atoms ($C_{1-10}$) of a straight, branched, saturated cyclic configuration and combinations thereof, attached to the parent molecular structure through an oxygen. Examples include methoxy, ethoxy, propoxy, isopropoxy, butoxy, t-butoxy, pentoxy, cyclopropyloxy, cyclohexyloxy and the like. "Lower alkoxy" refers to alkoxy groups containing one to six carbons. In some embodiments, $C_{1-3}$ alkoxy is an alkoxy group that encompasses both straight and branched chain alkyls of from 1 to 3 carbon atoms. Unless stated otherwise in the specification, an alkoxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$_a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "aromatic" or "aryl" refer to a radical with 6 to 14 ring atoms (e.g., C$_{6-14}$ aromatic or C$_{6-14}$ aryl) that has at least one ring having a conjugated pi electron system which is carbocyclic (e.g., phenyl, fluorenyl, and naphthyl). In some embodiments, the aryl is a C$_{6-10}$ aryl group. For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. Polycyclic aryl groups include bicycles, tricycles, tetracycles, and the like. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$_a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the term "halogen" refers to fluorine (F), chlorine (Cl), bromine (Br), or iodine (I). As used herein, the term "halide" or "halo", means fluoro, chloro, bromo or iodo.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

DETAILED DESCRIPTION OF THE INVENTION

The invention provides a novel molecular scaffold (e.g., a molecular switch) that reacts with a broad spectrum of nucleophiles with high fidelity, controllable selectivity and kinetic tunability. The molecular scaffold employs click-to-release and declick chemistry and is useful for wide ranging applications such as including protein covalent labeling and simultaneous quantification of the covalent labeling, reversible protein modification and traceless delivery, and as a general-purpose linker for diverse types of releasable antibody-drug conjugations.

The nucleophilic Michael addition based molecular switch afford the key advantages of click to release and declick features. Structural versatility offers an excellent way to control over both click-to-release and declick processes to access finely tunable reaction kinetics and the capability for reversing the click reaction. These features were translated to chemoselectively modifying cysteine over other nucleophilic residues.

By capturing on the structure-based variations on the reactivity, the ability to more indiscriminately modify proteins is also demonstrated where the modifications can be reversed to tracelessly recover proteins. A wide variety of masked functionalities can be introduced into the chemical switch, as demonstrated with conjugation to polymers and aptamers, where the functional molecules can be revealed in response to a thiol-based stimulus. Fast kinetics and chemical orthogonality of the click and declick reactions also allowed for facile preparation of orthogonally manipulatable functional hydrogels.

This molecular scaffold disclosed herein provides an unconventional class of reagents that can react with a wide range of amino acid residues on proteins and can be used to study protein structures or protein interactions especially when combined with mass spectrometry as a readout technique.

This invention significantly improves methods that use mass spectrometry to study the higher order structures of proteins or protein interactions with other proteins and ligands (e.g., antibody epitope mapping). The novel platform disclosed herein enables efficient incorporation of a wide variety of functionalities and simultaneous probing and quantification on protein labeling with readily assessable chromogenic readout.

The unique platform provides greater structural coverage than previous covalent labeling reagents and allows labeling at a wide variety of locations of a protein (e.g., cysteine, lysine, histidine, arginine, tyrosine, serine, threonine, aspartic acid, glutamic acid, tryptophan, asparagine, glutamine) which makes the modification much more efficient. Residues modified by this novel class of reagents are less prone to hydrolysis than previous labeling reagents. The result is that protein structures can be more sensitively analyzed (e.g., by mass spectrometry) when using this new type of reagents. The reagents are also modular and can be readily varied to incorporate a wide range of functional groups that modulate reactivity or improve mass spectrometry analysis.

The modification on protein residues can also be reversed to release the pristine protein when appropriate functionalities are included on the reagent.

The same platform can also be used to attach drugs with different functionalities to antibody and release them with tunable kinetics.

Thus, the compounds and materials, along with the synthetic methodologies disclosed herein can have broad impact on such diverse fields of analytics, mass spectrometry, proteomics, diagnostic or therapeutic delivery of agents.

In one aspect, the invention generally relates to a compound of the structural formula:

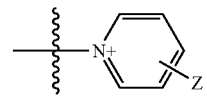

(I)

wherein
$R_x$ is a leaving group, optionally represented by X—$R_1$, wherein X is NH, $NR_6$ or O and each of $R_1$ and $R_6$ independently comprises one or more carbon atoms directly bound to X via single or double C—X bond(s);
$R_2$ is $OR_5$ or $NHR_5$, wherein $R_5$ is H, a linear or branched $C_1$-$C_{24}$ (e.g., $C_1$-$C_{12}$, $C_1$-$C_6$) alkyl, an alkyl chain bearing anionic and cationic hydrophilic functional groups, or an alkyl chain bearing a charge neutral group optionally selected from oligoethyleneglycols;
$R_3$ is H or comprises an aliphatic or aromatic group, and optionally $R_3$ comprises a polypeptide; and
$R_4$ is H or an alkyl group.

In certain embodiments, $R_4$ is H.

In certain embodiments, $R_2$ is $OR_5$. In certain embodiments, $R_2$ is $NHR_5$. In certain embodiments, $R_5$ is a $C_1$-$C_3$ alkyl (e.g., methyl, ethyl).

In certain embodiments, $R_2$ comprises an oligoethyleneglycol group represented by —$(CH_2CH_2O)_n$—, wherein n is an integer from about 1 to about 10 (e.g., 1, 2, 3, 4, 5, 6, 7, 8, 9, 10).

In certain embodiments, $R_3$ comprises an aliphatic group. In certain embodiments, $R_3$ comprises an aromatic group. In certain embodiments, $R_3$ is H.

In certain embodiments, $R_x$ comprises a primary amino, secondary amino, tertiary amino, or quaternary ammonium group. In certain embodiments, $R_x$ comprises a quaternary ammonium group.

In certain embodiments, $R_x$ comprises NR'R"R''', wherein each of R', R" and R''' is independently selected from H and a $C_1$-$C_6$ (e.g., $C_1$-$C_3$) alkyl. In certain embodiments, $R_x$ comprises:

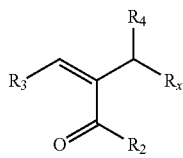

wherein Z is H, halogen, alkyl, amino, hydroxy, alkyloxy, carboxylic ester or carboxylic amide.

In certain embodiments, $R_x$ comprises a group selected from carboxylic ester, carbamate, carbonate, thiocarbonate and thiocarbamate.

In another aspect, the invention generally relates to a reaction product formed by reacting a disclosed compound of a nucleophile.

In certain embodiments, the nucleophile comprises a polypeptide sequence.

In certain embodiments, the nucleophile comprises a protein.

In certain embodiments, the nucleophile comprises an antibody or antibody fragment.

In certain embodiments, the nucleophile comprises a nucleic acid or a peptide aptamer.

In certain embodiments, the nucleophile comprises a polymer.

Non-limiting examples of compounds of the invention include:

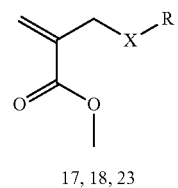

17, 18, 23

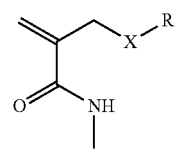

19

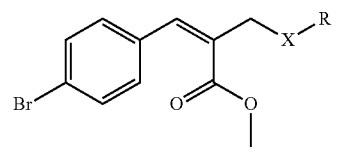

20

-continued

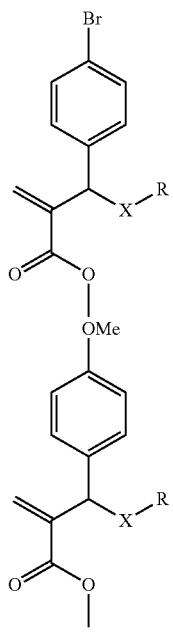

22, 24

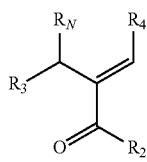

wherein X is NH, NR$_6$ or O and each of R and R$_6$ independently comprises one or more carbon atoms directly bound to X via single or double C—X bond(s).

In yet another aspect, the invention generally relates to a compound of the structural formula:

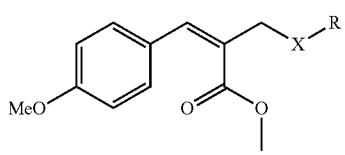

(II)

wherein
  R$_2$ is OR$_5$ or NHR$_5$, wherein R$_5$ is H, a linear or branched C$_1$-C$_{24}$ (e.g., C$_1$-C$_{12}$, C$_1$-C$_6$) alkyl, an alkyl chain bearing anionic and cationic hydrophilic functional groups, or an alkyl chain bearing a charge neutral group optionally selected from oligoethyleneglycols;
  R$_3$ is H or comprises an aliphatic or aromatic group, and optionally R$_3$ comprises a polypeptide;
  R$_4$ is H or an alkyl group; and
  R$_N$ comprises a polypeptide sequence.

In certain embodiments, R$_4$ is H.

In certain embodiments, R$_2$ is OR$_5$. In certain embodiments, R$_2$ is NHR$_5$. In certain embodiments, R$_5$ is C$_1$-C$_6$ (e.g., C$_1$-C$_3$) alkyl.

In certain embodiments, R$_3$ is H.

In certain embodiments, R$_N$ comprises a protein. In certain embodiments, R$_N$ comprises an antibody or antibody fragment.

In yet another aspect, the invention generally relates to a method for performing a chemical transformation, comprising shifting between two or more molecular states as represented by (I), (II) and (III):

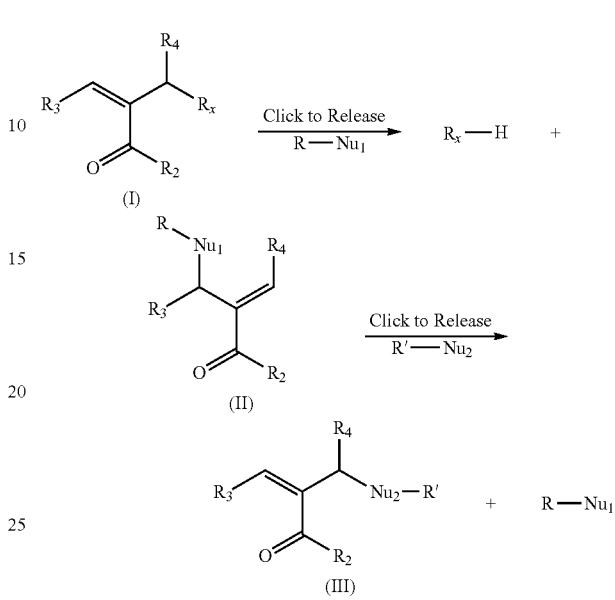

wherein
  each of molecular entities of (I), (II) and (III) is a stable compound,
  R$_x$ is a leaving group, optionally represented by X—R$_1$, wherein X is NH, NR$_6$ or O and each of R$_1$ and R$_6$ independently comprises one or more carbon atoms directly bound to X via single or double C—X bond(s);
  R$_2$ is OR$_5$ or NHR$_5$, wherein R$_5$ is H, a linear or branched C$_1$-C$_{24}$ (e.g., C$_1$-C$_{12}$, C$_1$-C$_6$) alkyl, an alkyl chain bearing anionic and cationic hydrophilic functional groups, or an alkyl chain bearing a charge neutral group optionally selected from oligoethyleneglycols;
  R$_3$ is H or comprises an aliphatic or aromatic group, and optionally R$_3$ comprises a polypeptide;
  R$_4$ is H or an alkyl (e.g., C$_1$-C$_3$) group;
  Nu$_1$ is a first nucleophilic group capable of undergoing click chemistry with (I) to form (II) while releasing R$_x$, and
  Nu$_2$ is a second nucleophilic group capable of undergoing click chemistry with (II) to form (III) while releasing R-Nu$_1$,
  each of R and R' comprises an aliphatic or aromatic group, and optionally R comprises a polypeptide.

In certain embodiments, R$_4$ is H.

In certain embodiments, R$_2$ is OR$_5$. In certain embodiments, R$_2$ is NHR$_5$.

In certain embodiments, R$_2$ comprises an oligoethyleneglycol group represented by —(CH$_2$CH$_2$O)$_n$—, wherein n is an integer from about 1 to about 10 (e.g., 1, 2, 3, 4, 5, 6, 7, 8, 9, 10).

In certain embodiments, R$_3$ is H.

In certain embodiments, R$_x$ comprises a primary amino, secondary amino, tertiary amino, or quaternary ammonium group. In certain embodiments, R$_x$ comprises a quaternary ammonium group.

In certain embodiments, $R_x$ comprises NR'R"R'", wherein each of R', R" and R'" is independently selected from H and a $C_1$-$C_6$ alkyl. In certain embodiments, $R_x$ comprises:

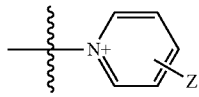

wherein Z is H, halogen, alkyl, amino, hydroxy, alkyloxy, carboxylic ester or carboxylic amide.

In certain embodiments, $R_x$ comprises a carboxylic ester group.

In certain embodiments, $Nu_1$ comprises a thiol group. In certain embodiments, $Nu_1$ comprises an amino group. In certain embodiments, $Nu_1$ comprises an ethylene oxide or PEG group.

In certain embodiments, R comprises a protein. In certain embodiments, R comprises an antibody or an antibody fragment.

In certain embodiments, R comprises a nucleic acid, for example, an aptamer or aptamer fragment.

In certain embodiments, the covalent conjugation of (I) to form (II) is irreversible.

In certain embodiments, the molecular switch allows switching among the molecular entities of (I), (II) and (III).

In yet another aspect, the invention generally relates to a method for covalently labeling a protein, comprising reacting a protein with a compound disclosed herein to form a covalent bond therebetween.

In yet another aspect, the invention generally relates to a method for covalently labeling an antibody or antibody fragment, comprising reacting an antibody or antibody fragment with a compound disclosed herein to form a covalent bond therebetween.

In certain embodiments, the covalent bond is formed between a thiol group on the protein, antibody or antibody fragment and the compound.

In certain embodiments, the covalent bond is formed between an amino group on the protein, antibody or antibody fragment and the compound.

In yet another aspect, the invention generally relates to a covalently labeled protein, antibody or antibody fragment produced by a method disclosed herein.

In yet another aspect, the invention generally relates to a method for labeling a protein, comprising: providing a protein of formula (IV) comprising a nucleophilic group (Nu) at a point of desired labeling:

R-Nu;     (IV)

reacting the protein (IV) with a compound of formula (V) having both a label and a reporter group:

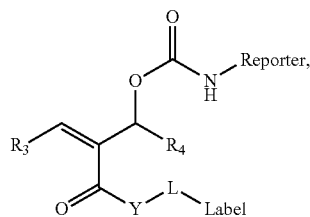

wherein
$R_3$ is H or an aliphatic or aromatic group;
$R_4$ is H or an alkyl group;
Y is O or $NR_5$, wherein $R_5$ is H or a $C_1$-$C_{12}$ alkyl (e.g., $C_1$-$C_3$ alkyl);
L is a linking group, and the reaction results in releasing of the reporter and formation of a labeled protein of formula (VI)

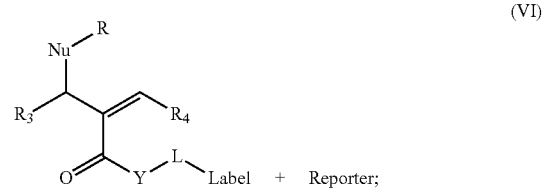

detecting a signal of the reporter and/or the presence of the label to analyze or quantify the protein.

In certain embodiments, R-Nu comprises R—SH.
In certain embodiments, $R_3$ is H.
In certain embodiments, Y is O. In certain embodiments, Y is NH.
In certain embodiments, L comprises —$(CH_2CH_2O)_n$—, wherein n is an integer from about 1 to about 10.

In certain embodiments, the point of desired labeling is selected from cysteine, lysine, histidine, arginine, threonine, tyrosine, serine, aspartic acid, glutamic acid, tryptophan, asparagine and glutamine. In certain embodiments, the point of labeling is cysteine. In certain embodiments, the point of labeling is lysine.

In certain embodiments, the reporter is a chromogenic upon release from compound (IV). In certain embodiments, the reporter is fluorescent.

In certain embodiments, the method further comprises: removing the label from the protein to re-generate the protein in its pristine form.

In yet another aspect, the invention generally relates to a method for analyzing a higher order structure of proteins, comprising: reacting a reference protein with a molecular scaffold disclosed herein under a set of conditions to form a covalently labeled reference protein; reacting a target protein with the molecular scaffold under the set of conditions to form a covalently labeled target protein; and analyzing the covalent labeled target protein and the covalently labeled reference protein, wherein the reference protein and the target protein have identical primary structures.

In certain embodiments, the method further comprises: determining whether there is a difference in the higher order structure of the reference protein and the target protein.

In certain embodiments, the higher order structure comprises secondary, tertiary, and/or quaternary protein structure In certain embodiments, the reference protein and the target protein comprises at least one amino acid selected from the groups consisting of cysteine, lysine, histidine, arginine, threonine, tyrosine, serine, aspartic acid, glutamic acid, tryptophan, asparagine and glutamine.

In certain embodiments, the target protein is selected from the group of proteins consisting of; antibodies, enzymes, ligands, peptide aptamers, and regulator factors.

In certain embodiments, the target protein is analyzed as a member of a protein-protein complex.

In certain embodiments, analyzing the covalently labeled target protein and the covalently labeled reference protein comprises mass spectrometric and/or fluorometric analysis.

In certain embodiments, the method is performed for analyzing protein-ligand binding.

In certain embodiments, the target protein has been contacted with a target ligand and the reference protein has not been contacted with any ligand or has been contacted with a reference ligand.

In yet another aspect, the invention generally relates to an antibody-drug conjugate of formula (VII):

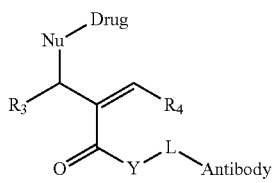

(VII)

wherein
"Drug" is a biologically active payload;
"Antibody" is an antibody or antibody fragment;
$R_3$ is H, an aliphatic or aromatic group;
$R_4$ is H or an alkyl group;
Y is O or $NR_5$, wherein $R_5$ is H or alkyl (e.g., $C_1$-$C_3$ alkyl); and
L is a linking group.

In certain embodiments, Y is O. In certain embodiments, Y is NH.

In certain embodiments, $R_3$ is H.

In certain embodiments, $R_4$ is H. In certain embodiments, $R_4$ is an alkyl (e.g., $C_1$-$C_3$ alkyl).

In certain embodiments, L comprises —(CH$_2$CH$_2$O)$_n$—, wherein n is an integer from about 1 to about 10 (e.g., 1, 2, 3, 4, 5, 6, 7, 8, 9, 10).

In certain embodiments, the biologically active payload is an anti-tumor agent. In certain embodiments, the anti-tumor agent is a chemotherapy agent. In certain embodiments, wherein the biologically active payload is selected from Bexarotene, Desmethyl Tamoxifen, Celecoxib, Vorinostat, Abiraterone, Abiraterone, monomethyl auristatin E (MMAE) and mertansine (DM-1).

In yet another aspect, the invention generally relates to a method for releasing a protein, comprising reacting an antibody-drug conjugate disclosed herein with a nucleophilic reagent.

In certain embodiments, the nucleophilic reagent is a thiol compound. In certain embodiments, the nucleophilic reagent is a glutathione.

In yet another aspect, the invention generally relates to a polymer comprising a monomer unit having a pendent group of formula (VIII):

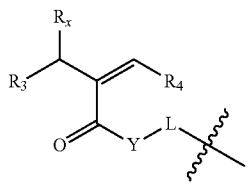

(VIII)

wherein
$R_x$ is a leaving group;
$R_3$ is H, an aliphatic or aromatic group;
$R_4$ is H or an alkyl group;
Y is O or $NR_5$, wherein $R_5$ is H or alkyl (e.g., $C_1$-$C_3$ alkyl); and
L is a linking group.

In certain embodiments, $R_x$ comprises a drug moiety.
In certain embodiments, $R_x$ comprises a protein.
In certain embodiments, Y is O. In certain embodiments, Y is NH.

In yet another aspect, the invention generally relates to a method for releasing a drug, comprising reacting a polymer disclosed herein with a nucleophilic reagent.

In certain embodiments, the nucleophilic reagent is a thiol compound. In certain embodiments, the nucleophilic reagent is a glutathione.

In certain embodiments, the drug is an anti-tumor agent. In certain embodiments, the anti-tumor agent is a chemotherapy agent. In certain embodiments, wherein the biologically active payload is selected from Bexarotene, Desmethyl Tamoxifen, Celecoxib, Vorinostat, Abiraterone, Abiraterone, monomethyl auristatin E (MMAE) and mertansine (DM-1).

In yet another aspect, the invention generally relates to a method for preparing a polymer or a hydrogel composition, comprising reacting

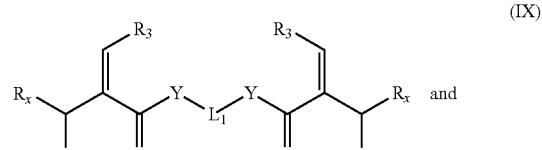

(IX)

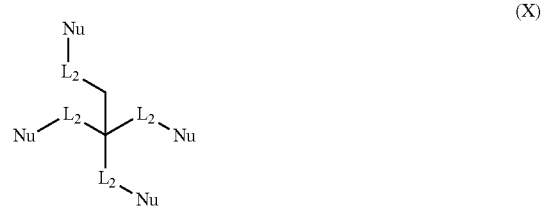

(X)

under conditions to form a polymer therebetween, wherein
$R_x$ is a leaving group;
$R_3$ is H, an aliphatic or aromatic group;
$R_4$ is H or an alkyl (e.g., $C_1$-$C_3$ alkyl) group;
Nu is a nucleophilic group;
Y is O or $NR_5$, wherein $R_5$ is H or alkyl (e.g., $C_1$-$C_3$ alkyl); and
$L_1$ and $L_2$ are linking groups.

In certain embodiments, the polymer or a hydrogel composition comprises a crosslinked three-dimensional polymer network.

In certain embodiments, the method further comprises encapsulating one or more payload materials (e.g., a biologically active protein or peptide).

In yet another aspect, the invention generally relates to a hydrogel composition, comprising a three-dimensional polymer network disclosed herein and one or more payload materials enclosed therein.

In yet another aspect, the invention generally relates to a device or implant comprising a hydrogel composition disclosed herein.

In yet another aspect, the invention generally relates to a pharmaceutical composition comprising a compound, an antibody-drug-conjugate, a polymer-drug conjugate or a hydrogel disclosed herein, a pharmaceutically acceptable excipient, carrier, or diluent.

In yet another aspect, the invention generally relates to a method for treating a disease or condition, comprising administering to a subject in need thereof a therapeutically effective amount of a pharmaceutical composition disclosed herein.

In certain embodiments, the disease or condition is tumor or cancer.

In yet another aspect, the invention generally relates to a protein labeling kit comprising a compound disclosed herein.

In certain embodiments of the compounds disclosed herein, at least one hydrogen (H) in the compound is enriched with $H^2$.

EXAMPLES

The exemplified molecular scaffold exhibits the advantages of both click-to-release and declick processes as well as predictable tunability in reaction kinetics. Also demonstrated, in addition to being a versatile structural control, is the utility of the approach as a bonding and debonding chemical switch for chemo-selective protein modification (bonding), traceless self-immolative linker for aptamer-drug conjugates (debonding) and orthogonal manipulation of hydrogels (bonding and debonding).

A general representation of the switch (A1) is shown in FIG. 1A. The molecule is an activated Michael acceptor, bearing a good leaving group (X) at the α-position. The nucleophilic addition of N1 to A1 is already favored, but can be significantly enhanced due to the release of leaving group; the subsequent generation a less activated Michael acceptor, A2, result in a relatively stable product.

Several advantages are afforded by this unique reaction: (i) the leaving group 'X' can be used to mask and then provide activated release of a variety of functional groups, with implications in the activated release of a drug molecule or a sensing reporter (click-to-release); (ii) the product A2 can be structurally customized to be either inert or susceptible to a stronger nucleophile N2 that causes the release of the originally clicked nucleophile N1 (declick reaction); and (iii) within the relatively small molecular volume, there exists at least five different locations that impact on the kinetics of these reactions, thus offering a fundamental understanding of the structural factors that underlie these two processes.

Figure 7:
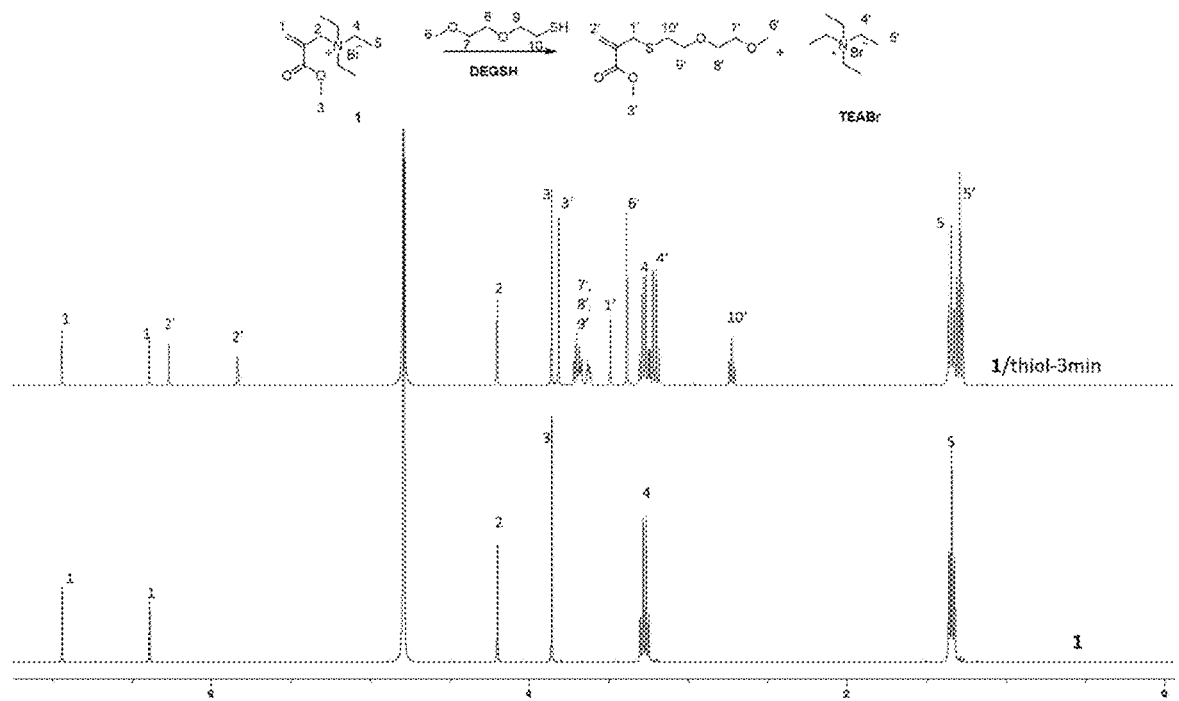
FIG. 7. Reaction of DEGSH with 1 followed by NMR. Bottom: compound 1; top: compound 1 incubated with 0.5 equivalent of thiol for 3 minutes. The reaction was carried out at 50 mM pH 7.4 phosphate buffer. Peak at 4.79 ppm belongs to $H_2O$.
Figure 8:
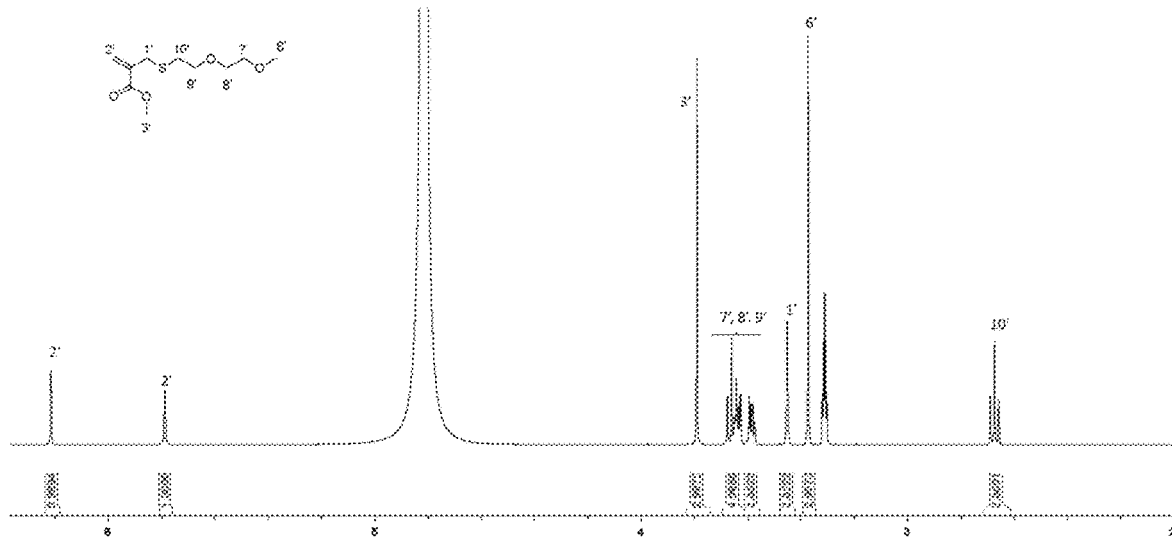
FIG. 8. NMR spectrum of isolated product from reaction of DEGSH and compound 1 in MeOH-d4.
Figure 9:
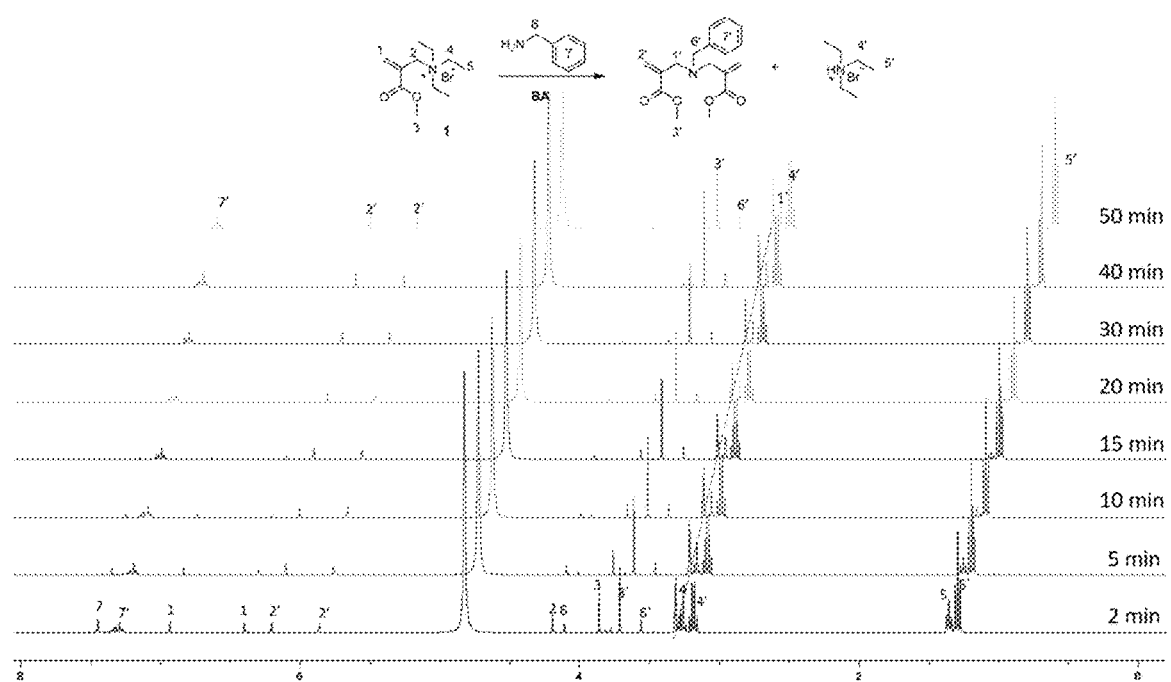
FIG. 9. Reaction of benzyl amine with 1 followed by NMR at different timepoints. Compound 1 was incubated 0.5 equivalent of benzyl amine and monitored. The reaction was carried at MeOH-d4 and 50 mM pH 7.4 phosphate buffer mixture (1:1). The spectra were aligned with MeOH-d4 peak. Peak at 4.79 ppm is attributed to $H_2O$.
Figure 10:
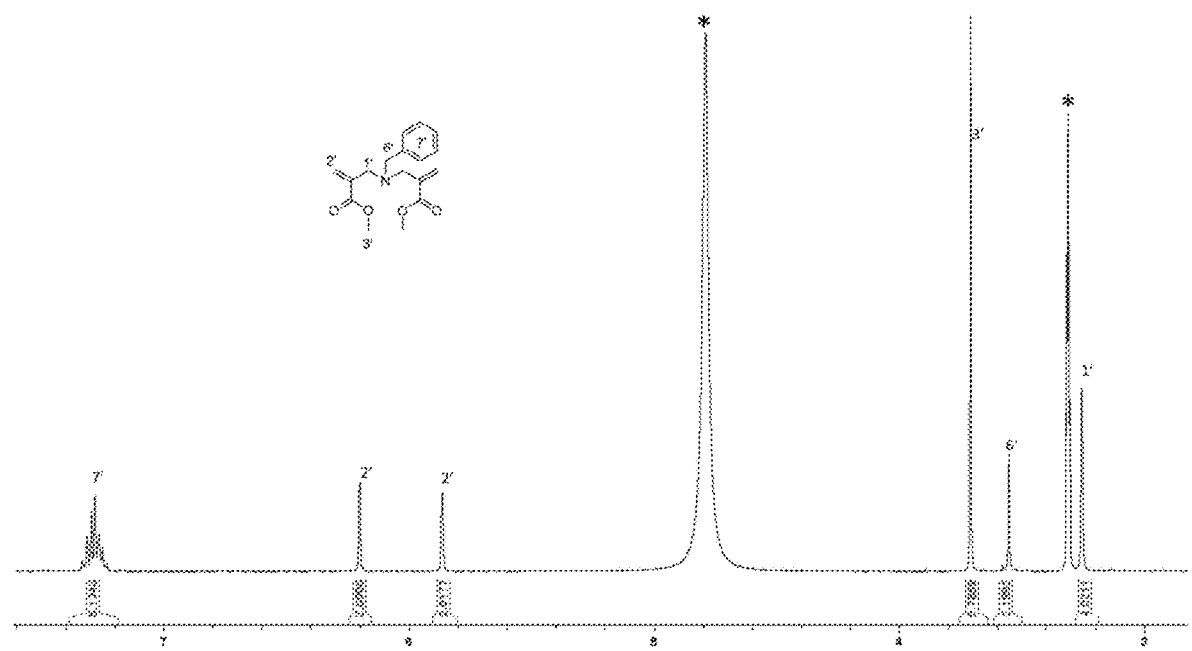
FIG. 10. NMR spectrum of isolated product from reaction of benzyl amine and compound 1 in MeOH-d4. "*" indicates solvent peaks.

Molecule 1, an acrylate with a quaternary ammonium leaving group was synthesized and evaluated for its reaction with two nucleophiles, 2-(2-methoxyethoxy)ethanethiol and benzylamine. $^1$H NMR showed that the reaction of 1 with the thiol is completed in 3 minutes (FIG. 7) and that the product is indeed due to the Michael-type addition (FIG. 1B and FIG. 8). Reaction of 1 with benzylamine was much slower at pH 7.4, where the reaction took ~50 minutes for completion. This is attributed to the weaker nucleophilicity of amines. Interestingly, the product here is the dialkylated product with no discernible monoalkylated product (FIGS. 9 and 10), likely because the secondary amine product of the first step is a much better nucleophile than the primary benzylamine.

Figure 2:
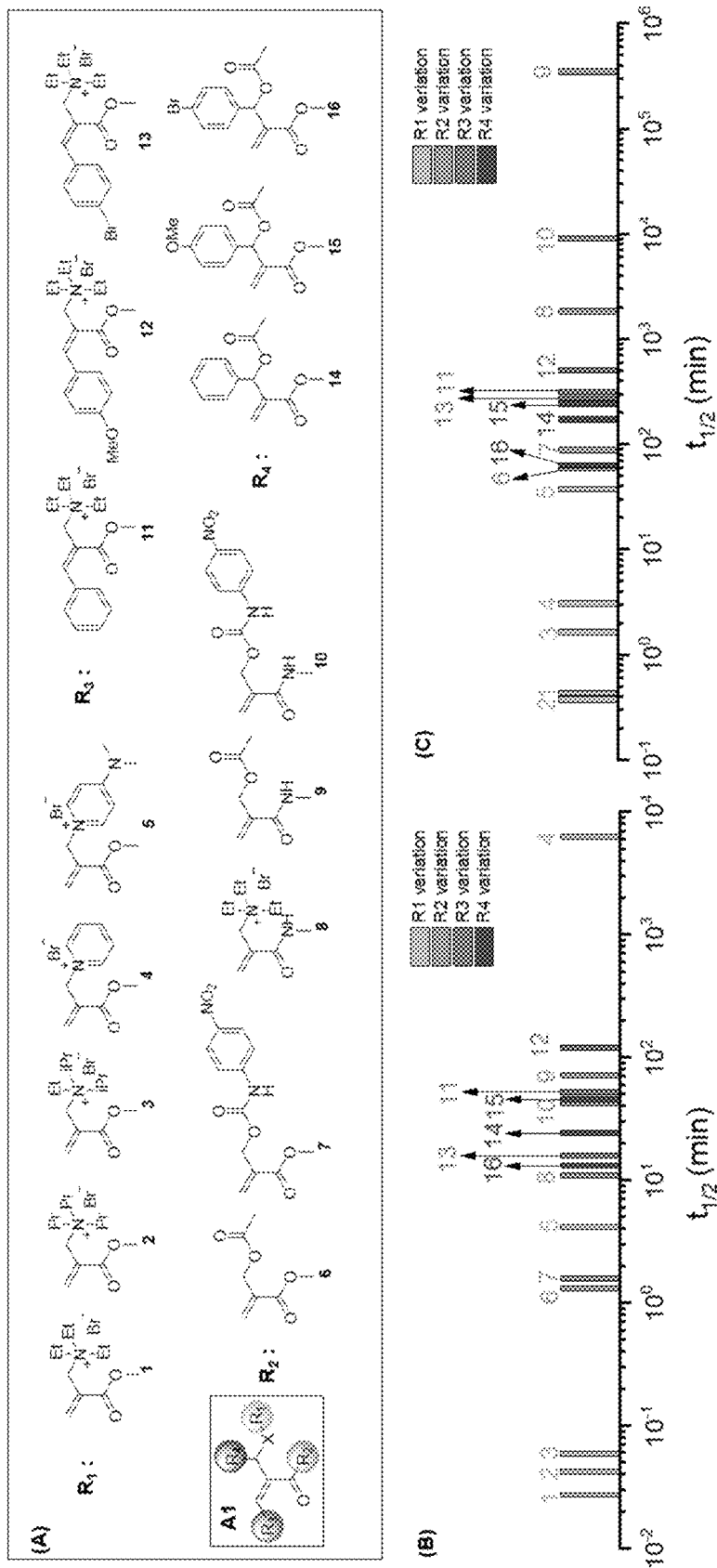
FIG. 2. Structure property relationship investigation on click-to-release kinetics. (A) Structure variations of A1. (B) Influence of substitution effect on thiol-click reactivity described by the half-life of thiol. (C) Influence of substitution on amine-click described by half-life of amine. Note: The reaction between 1-5, 8, 11-13 and thiol was carried out in MeOH-d4. Others were performed in the mixture of 50 mM phosphate buffer with specific pHs and deuterated solvent. Generally, aqueous reaction media significantly improved the reactivity. Reaction conditions and reaction kinetics of each molecules can be respectively found in method part in Supplementary Information and FIGS. 12 and 13.

To understand the factors that could influence the click-to-release kinetics, $R_1$, $R_2$, $R_3$, $R_4$ and X groups on A1 were systematically varied (FIG. 2A). The stoichiometry between A1 and nucleophiles was maintained as 2:1 in all experiments. Similarly, the reaction conditions such as solvent, concentration and pH were identical within a comparison group. However, these conditions might be different between two different comparison groups, either because of solubilization issues associated with a specific set of A1 derivatives or due to the need to slow down the reaction in order to achieve measurable kinetics. Moreover, whenever needed, at least one molecule in two different reaction conditions were also carried out to bridge reaction rates in two comparison groups.

Figure 11:
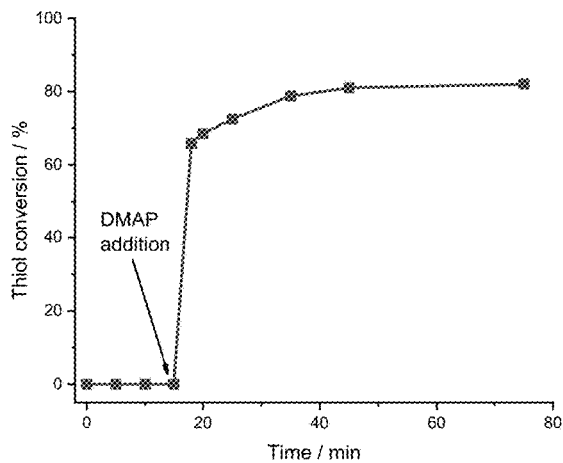
FIG. 11. Reaction of thiol with 4 enhanced by the addition of DMAP. The reaction was followed by NMR. NMR spectra can be found in FIGS. 67 & S68.
Figure 12:
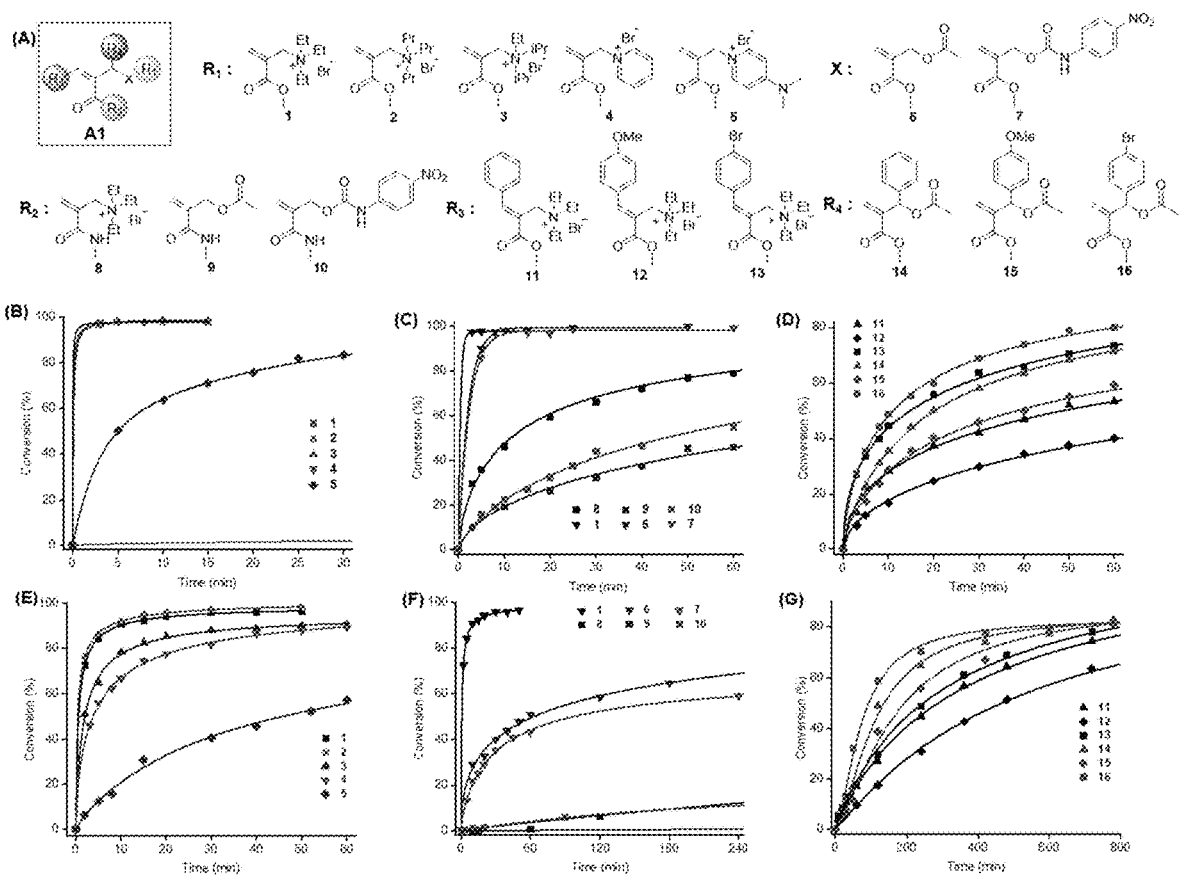
FIG. 12. Structure property relationship investigation on click-to-release kinetics. (A) Structure variations of A1. (B) Influence of $R_1$ group on thiol-click reaction. (C) Effect of $R_2$ substitution on thiol-click reaction. (D) $R_3$ and $R_4$ substitution effect on thiol-click reaction. (E) Influence of $R_1$ group on amine-click reaction. (F) Effect of $R_2$ substitution on amine-click reaction. (G) $R_3$ and $R_4$ substitution effect on amine-click. Note: Reaction between all ammoniums and thiol were performed in MeOH-d4. Others were performed in phosphate buffer and deuterated solvent mixture. Generally, aqueous reaction media significantly improve the reactivity. The specific reaction conditions can be found in Method.
Figure 13:
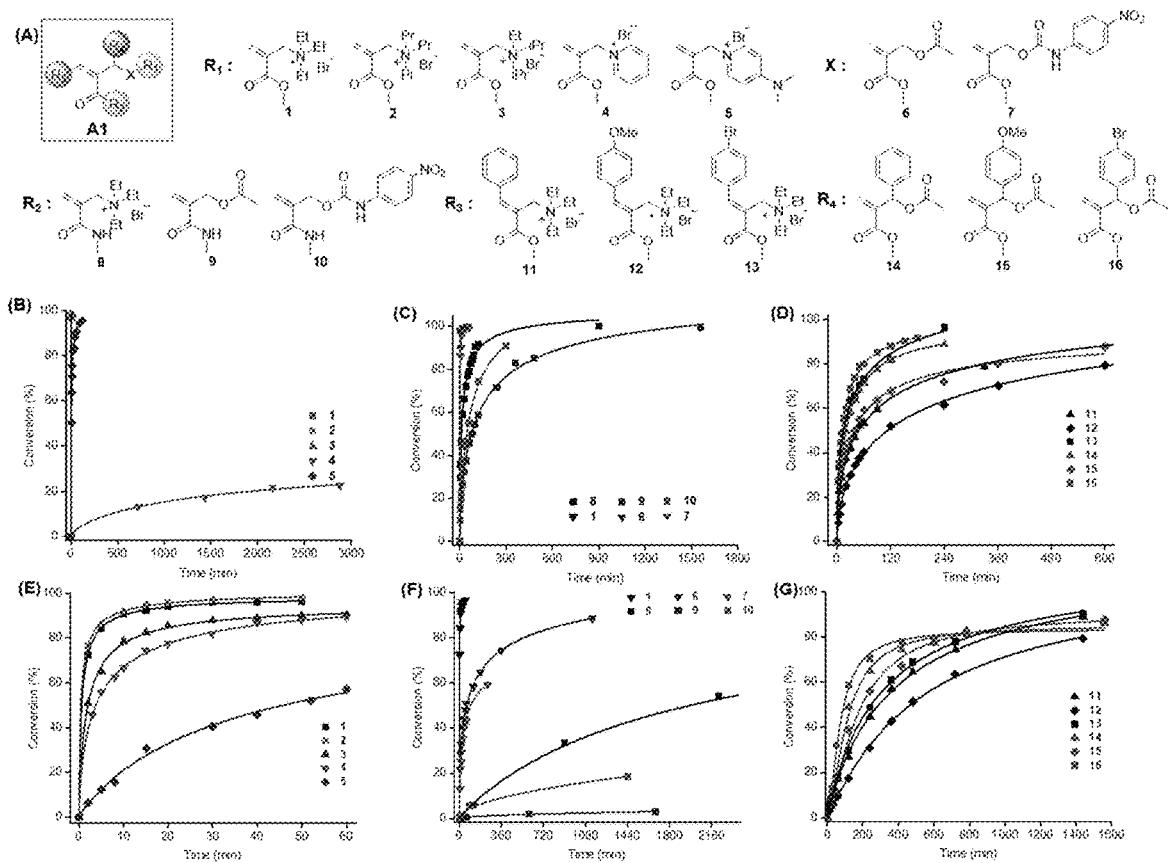
FIG. 13. Kinetics of click reaction corresponding to FIG. 12 but shown in longer time scale. (A) Structure variations of A1. (B) Influence of $R_1$ group on thiol-click reaction. (C) Effect of $R_2$ substitution on thiol-click reaction. (D) $R_3$ and $R_4$ substitution effect on thiol-click reaction. (E) Influence of $R_1$ group on amine-click reaction. (F) Effect of $R_2$ substitution on amine-click reaction. (G) $R_3$ and $R_4$ substitution effect on amine-click. Note: Reaction between all ammoniums and thiol were performed in MeOH-d4. Others were performed in phosphate buffer and deuterated solvent mixture. Generally, aqueous reaction media significantly improve the reactivity. The specific reaction conditions can be found in Method.

First, the thiol-click reactions for 1-5 with aliphatic and aromatic ammonium leaving groups were studied. The reactions were completed within just a few minutes for molecules 1-3, when the leaving group was an aliphatic ammonium moiety. However, the reaction was much slower for 4 and 5, containing aromatic ammonium leaving groups (FIG. 2B). This difference is attributed to the fact that the positive charge in aromatic ammoniums are more stabilized by delocalization. By extension, 5 would be less reactive than 4, as the electron-donating dimethylamino group can better stabilize the charge. However, it was observed that 5 was faster than 4. The observation is likely due to the basicity of the released DMAP molecule, which can accelerate the reaction in MeOH-d4 where the pH of reaction mixture could not be maintained. This assertion is supported by the drastic rate enhancement observed in the presence of extrinsic DMAP in 4/thiol reaction (FIG. 11). To further investigate this, the reactivity of 4 and 5 towards benzylamine was analyzed, where pH of solution was maintained in deuterated MeOH/buffer mixed media (FIG. 2C). Indeed, the reactivity of 4 toward amine is higher than 5 here. Overall, this study provided the initial indication that the leaving group can significantly influence the kinetics of the click-to-release reaction.

To further test the diversity of leaving groups, varied $R_1$ was varied from quaternary ammonium (1) to carboxylate (6) to carbamate moieties (7), where the released product would be a tertiary amine, carboxylic acid or a primary amine respectively. Indeed, both with the thiol and the amine addition reactions, the relative reactivities correlate (1>6>7) with the leaving group ability (FIG. 2B-2C). Considering the electronic influence on reactivity, it was hypothesized next that the reactivity can be altered by varying the electrophilicity through variations in the $R_2$ moiety. Accordingly, acrylamide molecules 8, 9, and 10 were synthesized as the weak electronic acceptor analogs of 1, 6, and 7 respectively. Indeed, the acrylamides were found to be considerably slower than the corresponding acrylates (FIG. 2B-2C).

Figure 14:
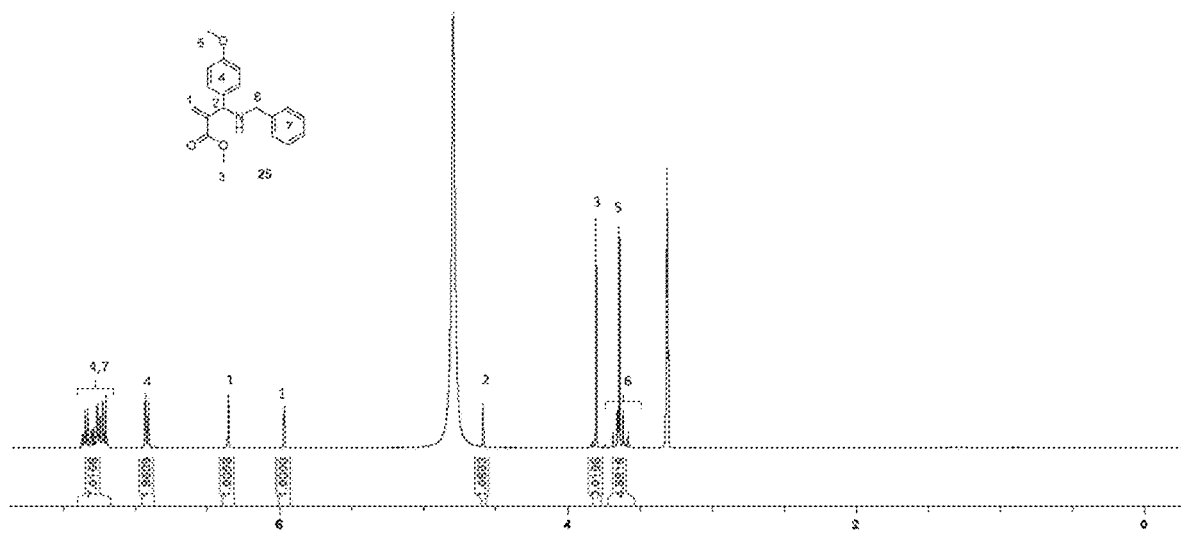
FIG. 14. Isolated product from amine-click reaction of 12 and benzyl amine.
Figure 15:
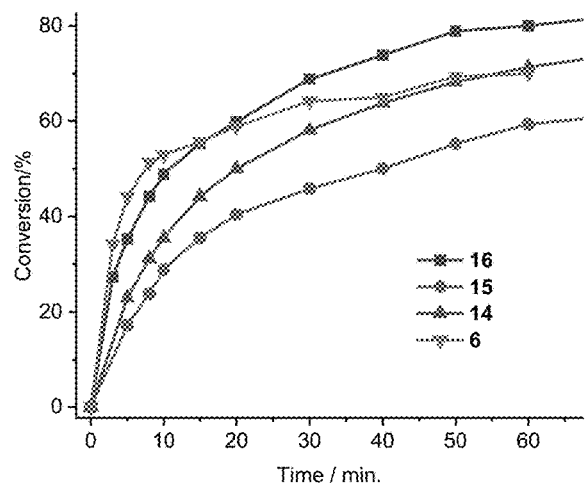
FIG. 15. Kinetics of thiol-click reaction carried at pH 6.2. All of reaction were performed at mixture of 500 μL of MeOH-d4 and 500 μL of 50 mM pH 6.2 phosphate buffer.

Next, the influence of $R_3$ substitution was investigated using 11-13, the reactivities of which were substantially lower compared to the unsubstituted olefin 1 (FIG. 2B-2C). In addition to the steric barrier for nucleophilic attack, the extended conjugation could also deactivate the double bond. In such a scenario, an electron-donating substituent should make the molecule less reactive. Indeed, it was found that the reactivity order was bromophenyl>phenyl>methoxylphenyl, for both amine and thiol reactions. Interestingly, only mono-addition product was observed for the latter, which also supports the sterics-based inhibition of this reaction (FIG. 14). When substituted phenyl groups are incorporated onto the allylic position as the $R_4$ substitution, the electron-withdrawing bromo moiety was found to accelerate the reaction. This observation was taken to indicate that the reaction goes through an enolate intermediate and the step involving the leaving group has an early transition state structure with a developing negative charge at the benzylic position (FIG. 15).

Figure 3:
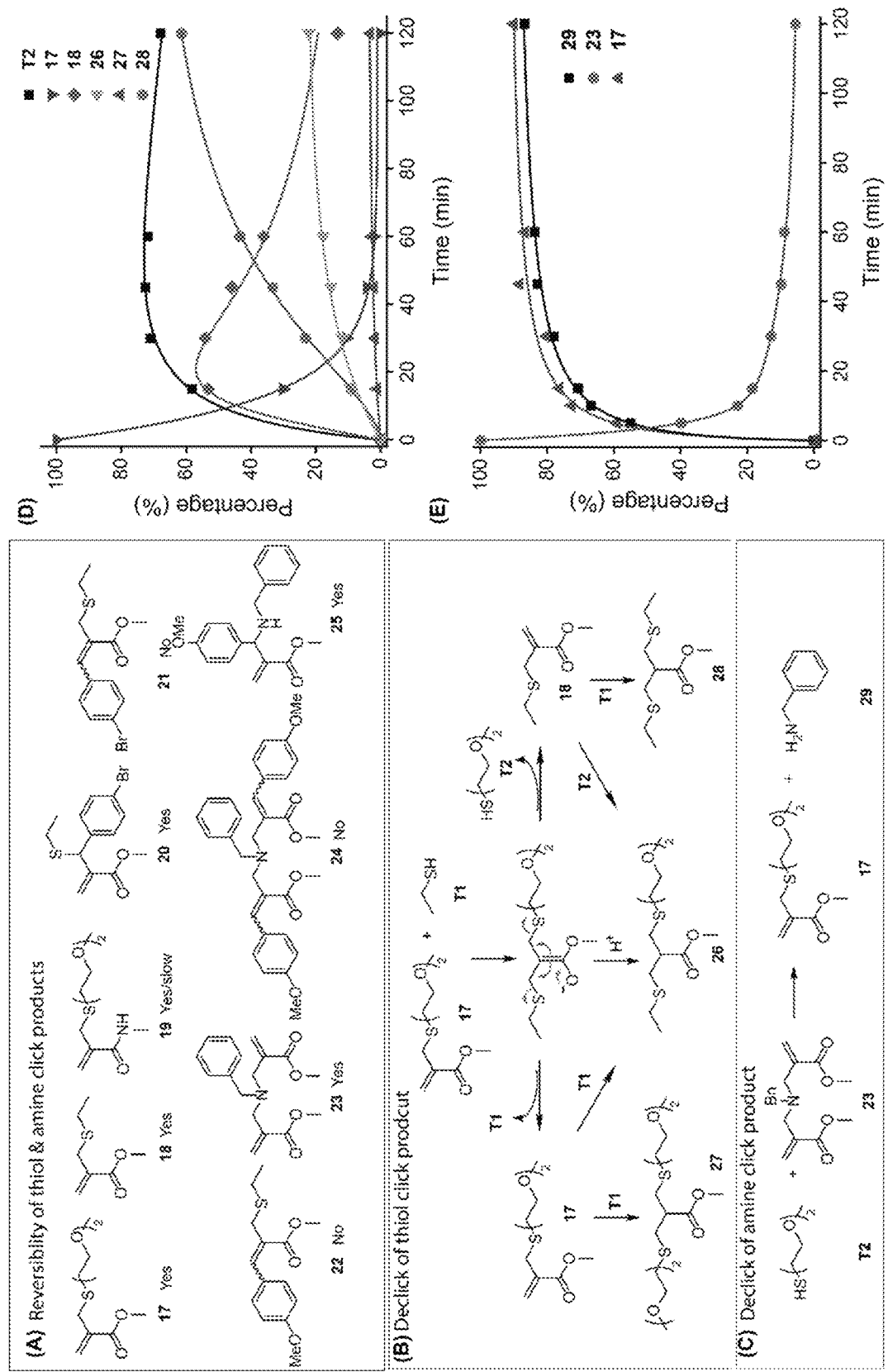
FIG. 3. Customizing the reversibility and irreversibility of thiol and amine click product. (A) Structures of products resulting from thiol and amine-based click-to-release reaction. (Occurrence of declick reaction is indicated by "Yes"). (B) Thiol-triggered declick of thiol-based click-to-release product, 17. [T1]/[17]=8. (C) Thiol-triggered declick of amine-based click-to-release product, 23. [T2]/[23]=2. (D) Percentage of existing species in the course of declick reaction of 17. (E) Percentage of existing species in the course of declick reaction of 17.
Figure 4:
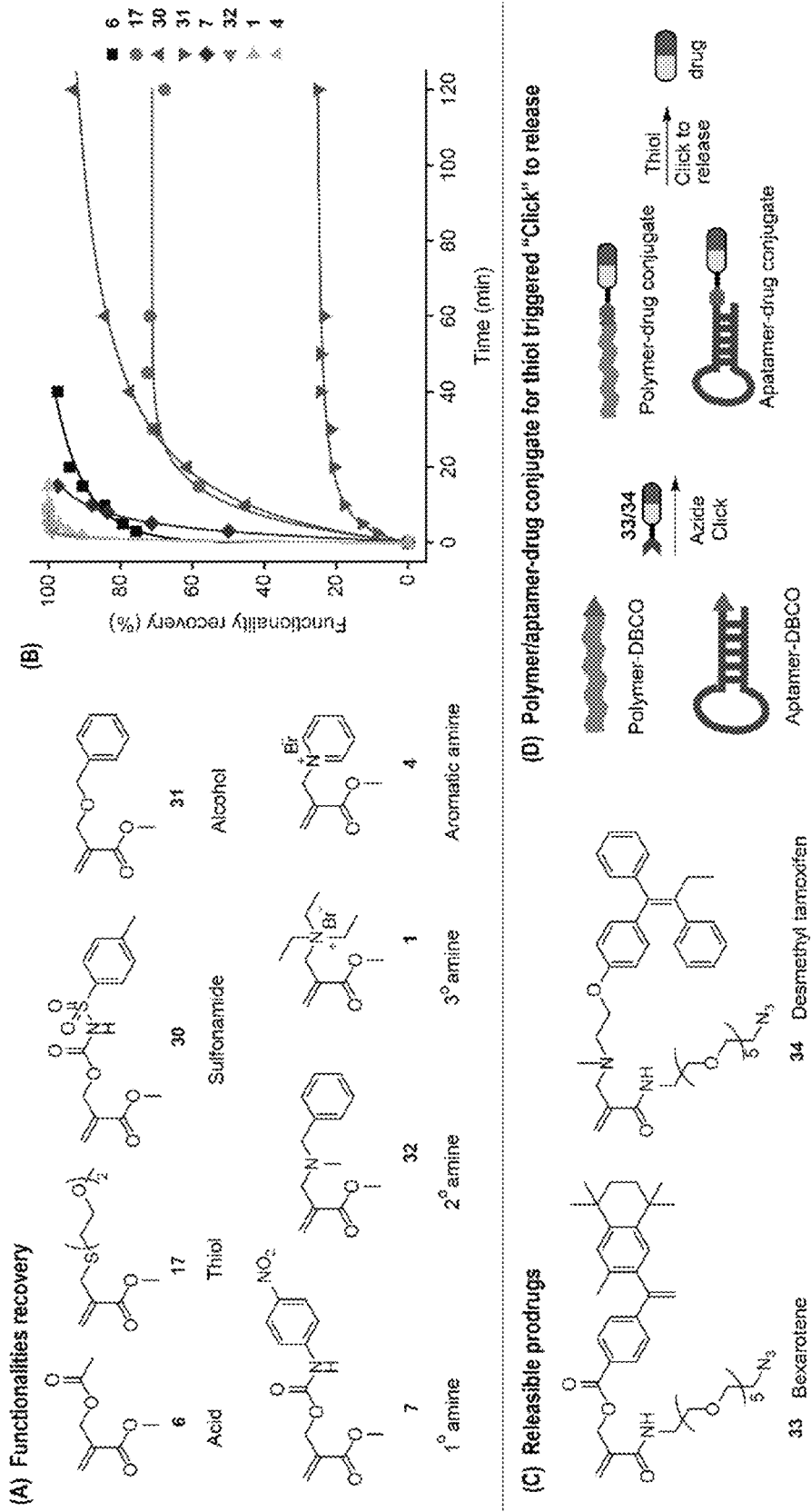
FIG. 4. Click-to-release as a universal strategy for uncaging functionalities. (A) Variations of functionalities can be recovered from the molecular switch. (B) Thiol-triggered recovery of functionality. (C) Thiol-triggered releasable prodrugs readily available for macromolecule conjugation. (D) Schematic representation of thiol induced click-to-release of active drugs from polymer/aptamer-drug conjugate FIG. 5. Protein modification with the molecular switches. (A) Schematic illustration of cysteine-selective labeling of βLGb driven by reactivity difference between 1 and 8. (B) Mass spectra of unlabeled βLGb (bottom) and βLGb labelled with 1(middle), and 8 (top). Note: The spectra show only one charge state (+17) and the full spectra are shown in FIG. 46. 1 La stands for 1 modification. Peak highlighted by * corresponds to βLGb with disaccharide PTM. (C) Schematic illustration of reversible modification of Myoglobin using compound 1. (D) Mass spectra of compound 1 modified myoglobin further incubated with and without thiol. Note: One charge state is shown and spectra with all charge states shown in FIG. 55. 1 La stands for 1 modification. (E) Influence of PEG modification on BCA activity evaluated by chromogenic assay. (F) Use the click-to-release strategy to spectroscopically monitor modification of myoglobin by following absorbance of reporter, 4-nitroaniline. (G) 4-nitroaniline absorbance evolution during myoglobin modification with compound 7. (H) The number of modifications on myoglobin corresponding to (G).
Figure 16:
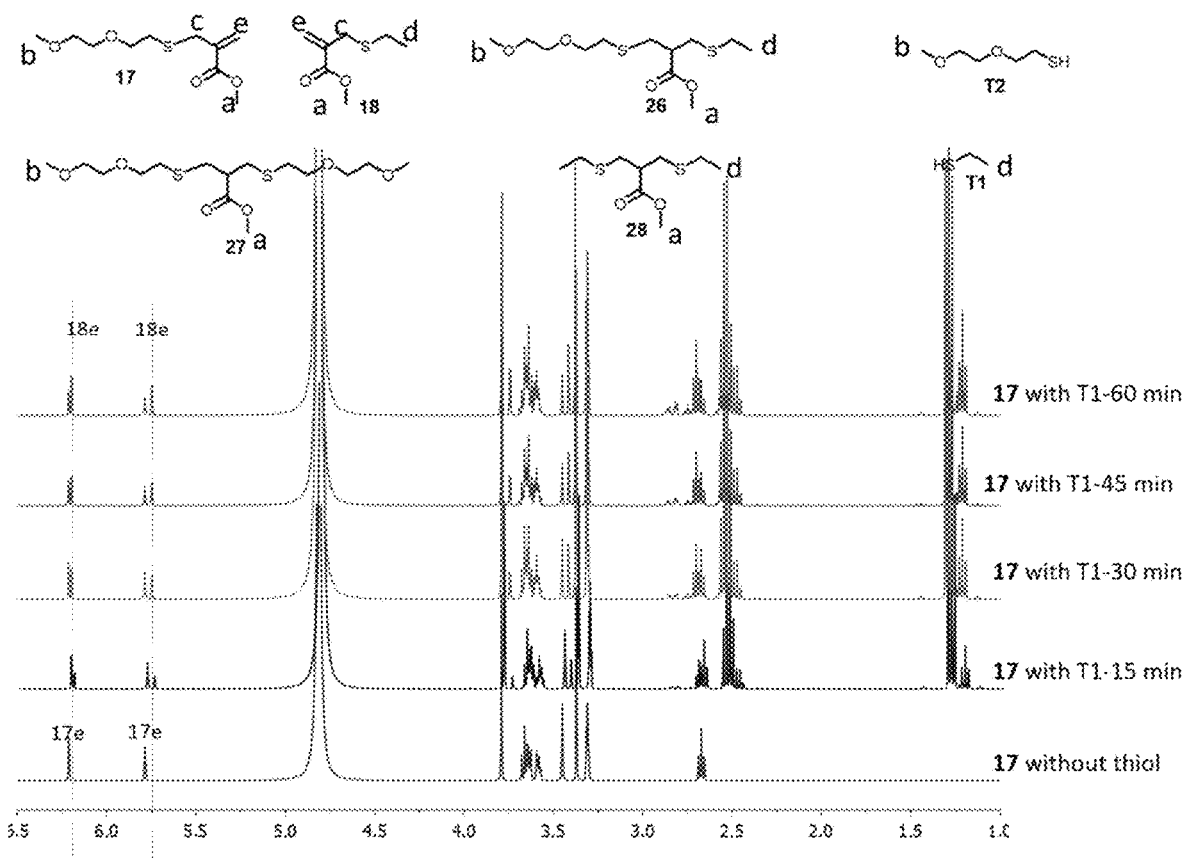
FIG. 16. Reversion of thiol-click product, 17 to T2 triggered by T1 followed by NMR. [T1]/[17]=8/1. The reaction was carried out in mixture of MeOH-d4 and 50 mM pH 6.8 phosphate buffer (1:1).
Figure 17:
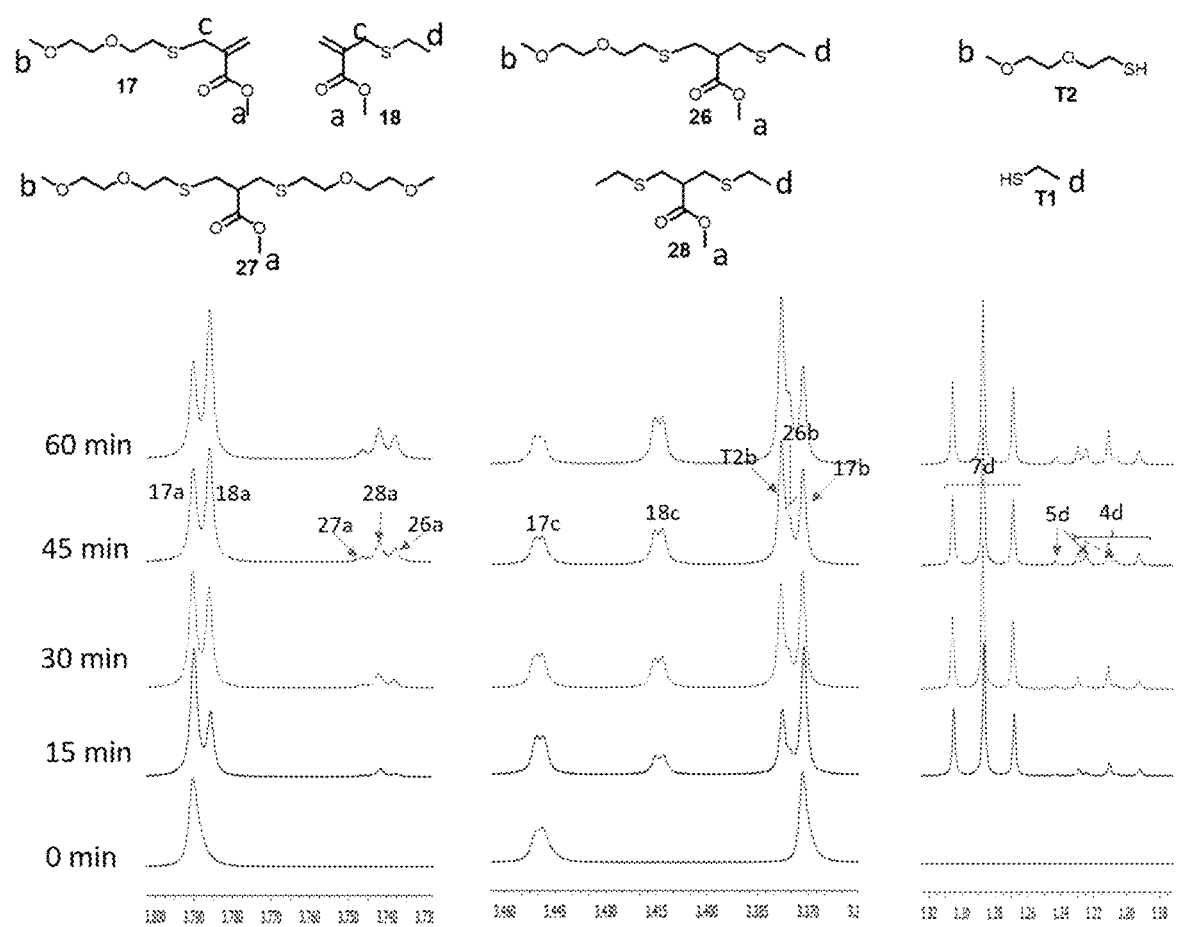
FIG. 17. Zoom-in spectra of FIG. 16. The integration of the peaks assigned was used to calculate the population of each species.
Figure 18:
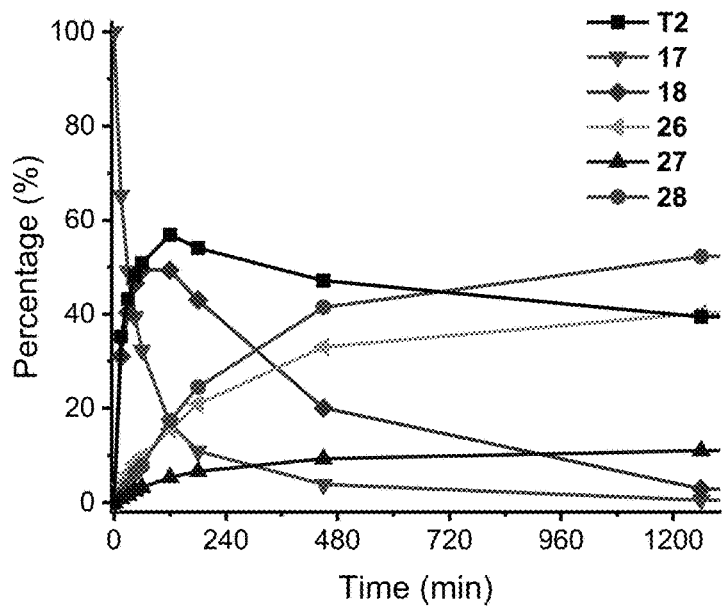
FIG. 18. Thiol-triggered "Declick" of thiol "Click" product, 17. [T1]/[17]=3. The reaction was carried out in mixture of MeOH-d4 and 50 mM pH 6.8 phosphate buffer (1:1). [17]:10 mM.

The structural factors that dictate reversibility were also evaluated. Possible products from thiol and amine based click reactions with the A1 scaffold are shown as structures 17-25 in FIG. 3A. Reversibility, i.e. the release of the originally clicked nucleophile, was studied. First, when 17 was treated with 8 equivalents of ethanethiol (T1), generation of 18 is expected along with the released diethyleneglycolthiol (T2) (FIG. 3B). Concurrent formation of other species 26-28 was also observed, which can be understood based on the Michael addition-elimination mechanism (FIGS. 16 and 17). Solely, from the declick perspective, 70% of the originally clicked T2 was released in this reaction. Lack of complete release of T2 is attributed to its reaction with 18 to generate 26. The fact that ethanethiol (T1) also reacts with 18 to form 28, relative to 26, indicates that the product distribution is simply determined by the ratio of T1 and T2 nucleophiles. This assertion was confirmed by decreasing the amount of T2, where an increase in the percentage of 26 was observed (FIG. 18).

Figure 19:
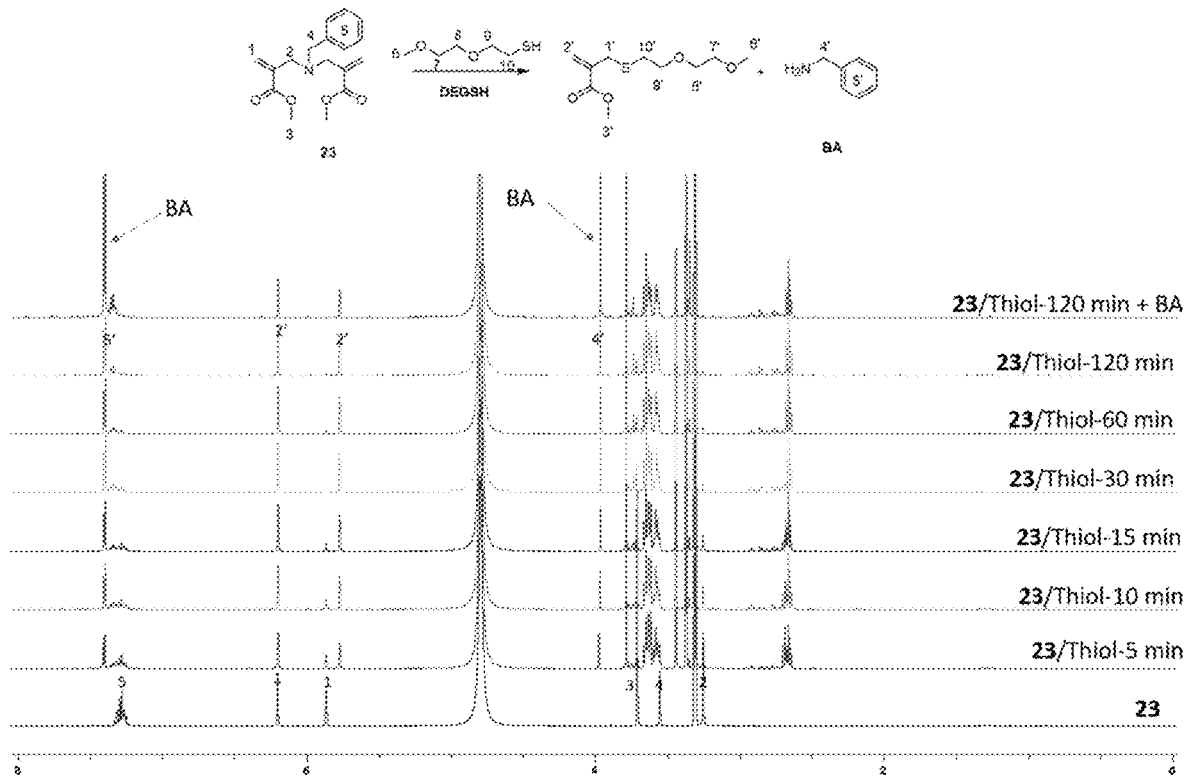
FIG. 19. Thiol triggered declick of amine-click product, 23. The progress of the reaction was followed by NMR. After 120 minutes, benzyl amine was added to the reaction mixture to identify that the released compound is actually benzyl amine. The reaction was carried out in mixture of MeOH-d4 and 50 mM pH 7.4 phosphate buffer (2:1). The ratio between 23 and DEGSH was 2:1. Concentration of 23 was 6.67 mM.

Similarly, thiol triggered declick of the amine-click 23 was also investigated (FIG. 3C). More than 80% of benzylamine (29) was released in the presence of just 2 equivalents of T2 (FIGS. 3E and 19). The rather clean conversion, even with low amounts of thiol, is attributed to the weaker nucleophilicity of benzylamine. Further studies on thiol-triggered declick of other compounds show that 17, 18, 19, 20, 23, and 25 can all be reversed to release the original thiol or amine. However, declick of 21, 22, and 24 is not available (FIGS. 20-27), likely due to the decreased electrophilicity of the phenyl-substituted double bond.

The ability to attach a functional molecule to a scaffold and then readily recover it in the presence of a trigger has implications in many applications, including in switchable catalysis, sensing, cellular manipulation and linker chemistry for prodrug and antibody-drug conjugates (ADCs). (Staben, et al. 2016 *Nat. Chem.* 8, 1112-1119; Versteegen, et al. 2018 *Angew. Chem. Int. Ed.* 57, 10494-10499.) In order to fully recognize this potential, the scope of the releasable functionalities must be broad. Disclosed herein for the first time, is a wide variety of functionalities including carboxylic acid, thiol, sulfonamide and alcohol can be released, in addition to 1°, 2°, 3°, and aromatic amines in response to a thiol trigger (FIGS. 4A-4B, 28-37). Release of these molecules was quantitative, except with the thiol (~70%) and the alcohol (~20%). In these two cases, the addition was quantitative, but did not result in the subsequent release of the original nucleophile. From a solely molecular release perspective, note that these products can be more completely released as thiols and alcohols, if the leaving groups were incorporated as thiocarbonates or carbonates respectively.

Figure 42:
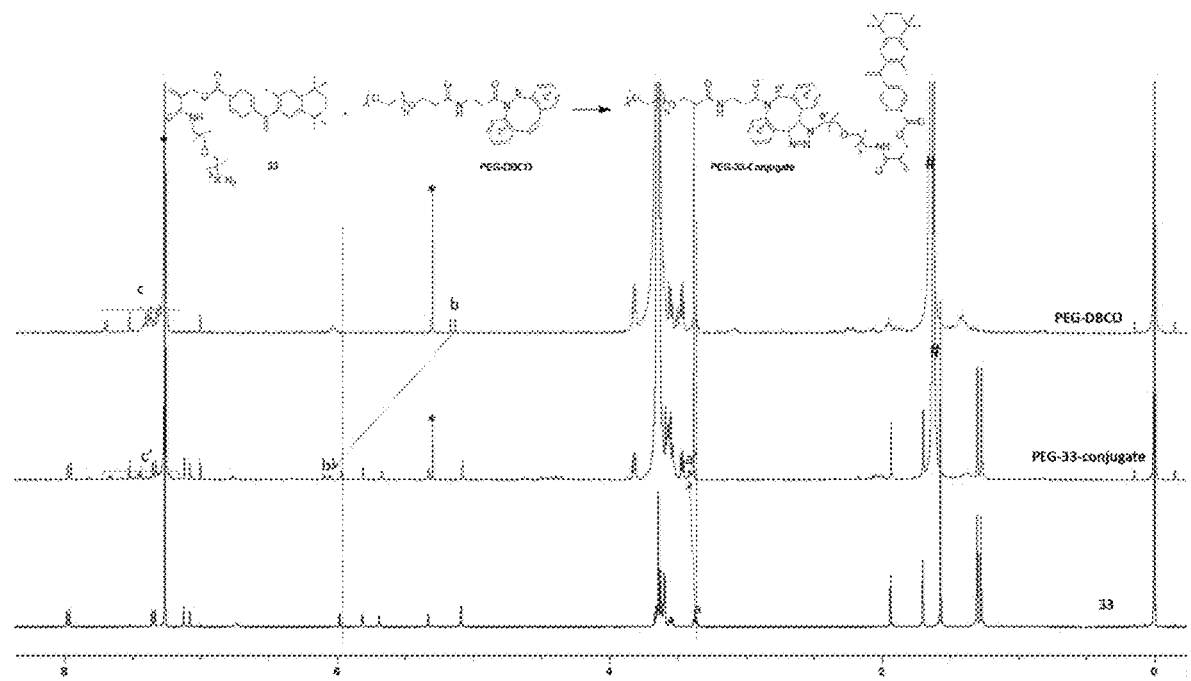
FIG. 42. Conjugation of compound 33 to PEG-DBCO followed by NMR in $CDCl_3$. (* and # are attributed to DCM and $H_2O$). Top: NMR spectrum of PEG-DBCO. Bottom: NMR spectrum of compound 33. Middle: NMR spectrum of PEG-drug conjugate. Observation of chemical shift shifting of a, b and c protons whose chemical shift should be significantly changed after click reaction and signatures from both precursors suggests successful conjugation.
Figure 43:
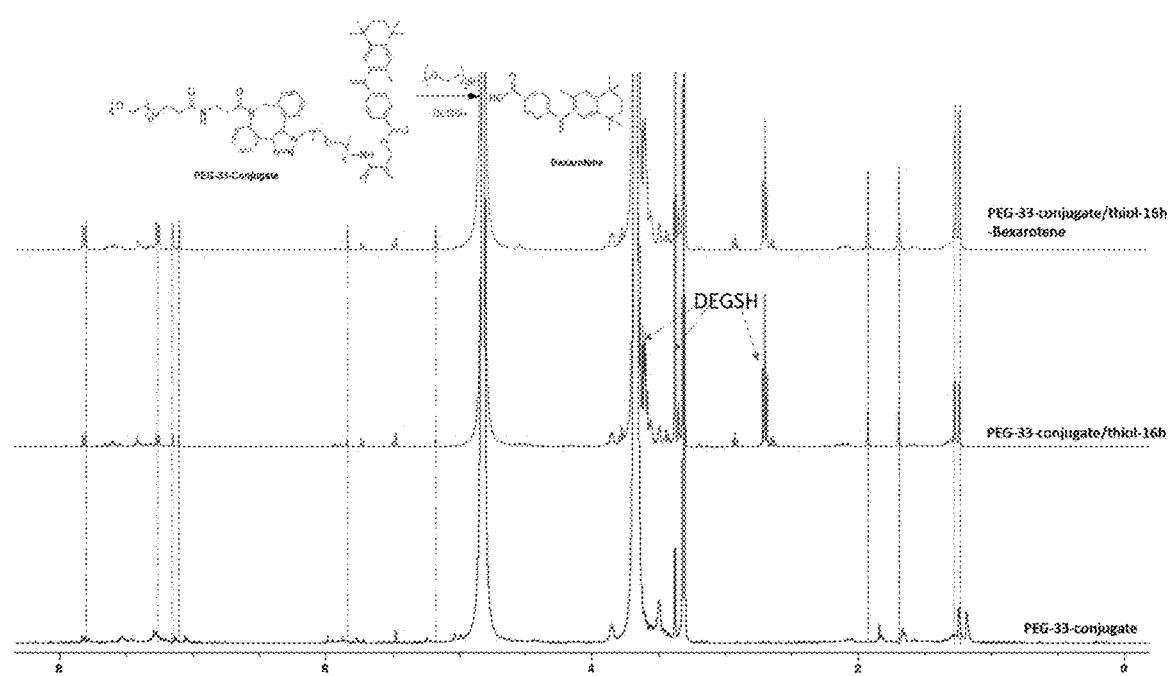
FIG. 43. Release of bexarotene from PEG-33 conjugate in the presence of thiol monitored by NMR. Bottom: PEG-33 conjugate itself. Middle: PEG-33 conjugate treated with thiol for 16 hours. Top: PEG-33 conjugate treated with thiol for 16 hours followed by addition of commercial bexarotene to validate the identity of released molecule. The fact that newly appeared peaks after thiol incubation is identical to Bexarotene proves the release of Bexaroten from polymer-drug conjugate. The reaction was carried out at MeOH-d4 and 50 mM pH 7.4 phosphate buffer (1:1). [PEG-33]/[DEGSH]=1:2. [PEG-33]: 1 mM.
Figure 44:
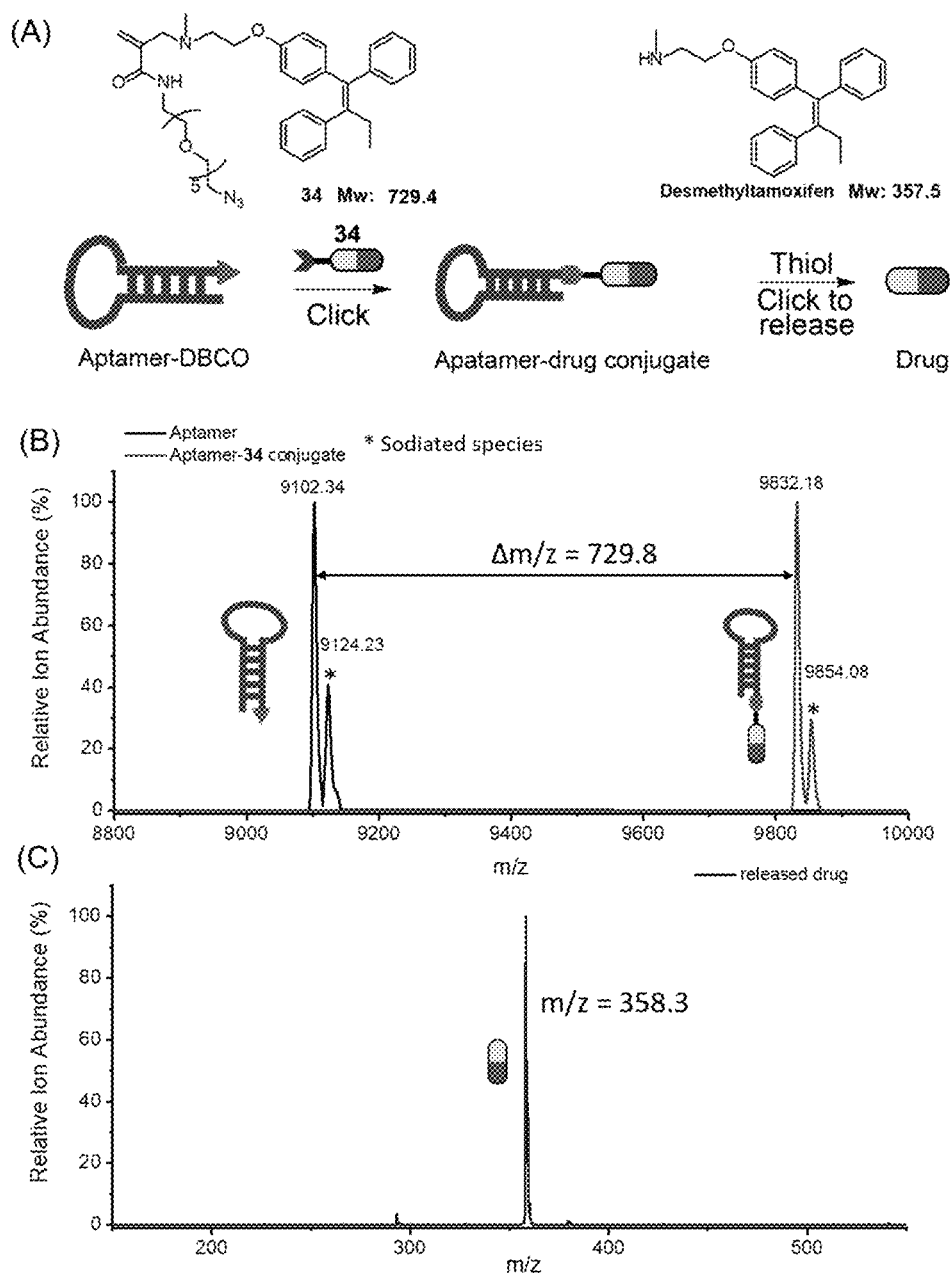
FIG. 44. Conjugation of compound 34 to aptamer (AS1411) and thiol-triggered release of desmethyltamoxifen from aptamer-drug conjugate. (A) Schematic illustration of aptamer-drug conjugation and thiol-triggered release of desmethyltamoxifen from conjugate. (B) Successful conjugation proved by the observation of mass shift of 729.8 which is identical to molecular weight of compound 34 from mass spectrometry analysis. (C) Release of desmethyltamoxifen from aptamer-drug conjugate suggested by observation of exact m/z of desmethyltamoxifen from LC-MS.

To further illustrate the scope of click-to-release approach, a carboxylic acid-based drug (bexarotene) and a 2°-amine based drug molecule (desmethyltamoxifen) were incorporated on to a polymer and a DNA aptamer respectively. To generate conjugates of these prodrugs, DBCO-terminated PEG and AS1411 aptamer were treated with azide-functionalized 33 and 34 to obtain the respective conjugates (FIGS. 4D and 38-41). Indeed, both these conjugates were able to release the drug molecules in their original form with high fidelity (FIGS. 42-44).

Figure 45:
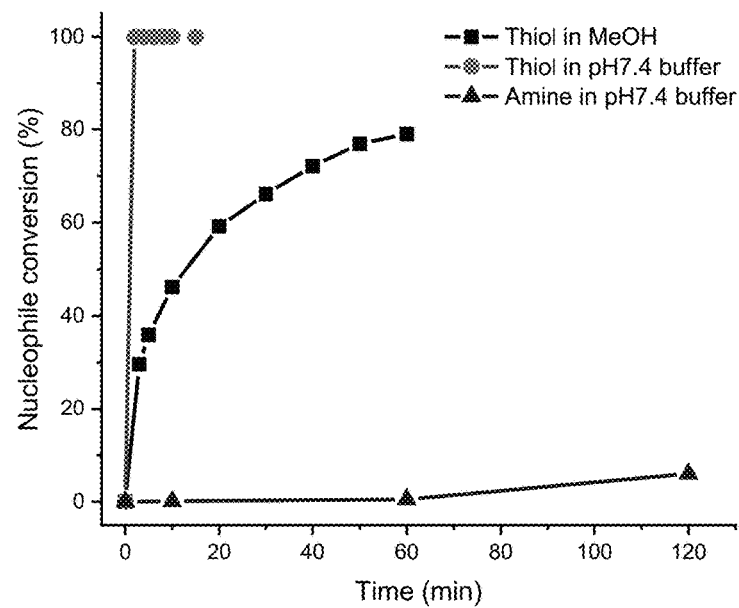
FIG. 45. Solvent dependent reactivity of compound 1 toward thiol and amine. Aqueous reaction media drastically accelerates the reaction and improves the selectivity among thiol and amine. [1]/[Nucleophile]=2:1.

Chemical modification of proteins was also investigated. Considering proteins' delicate nature, modification reactions must be free of organic solvents and fast. The ammonium version of A1 is both reactive and water soluble and therefore was investigated for the modification. Specifically, acrylamide 8 exhibited a clearly distinguishable reactivity between thiols and amines in aqueous medium (FIG. 45), and was less reactive than ester 1. Both of these molecules were tested for the modification of β-lactoglobulin B (βLGb), which has one cysteine and fifteen lysine residues.

Figure 5:
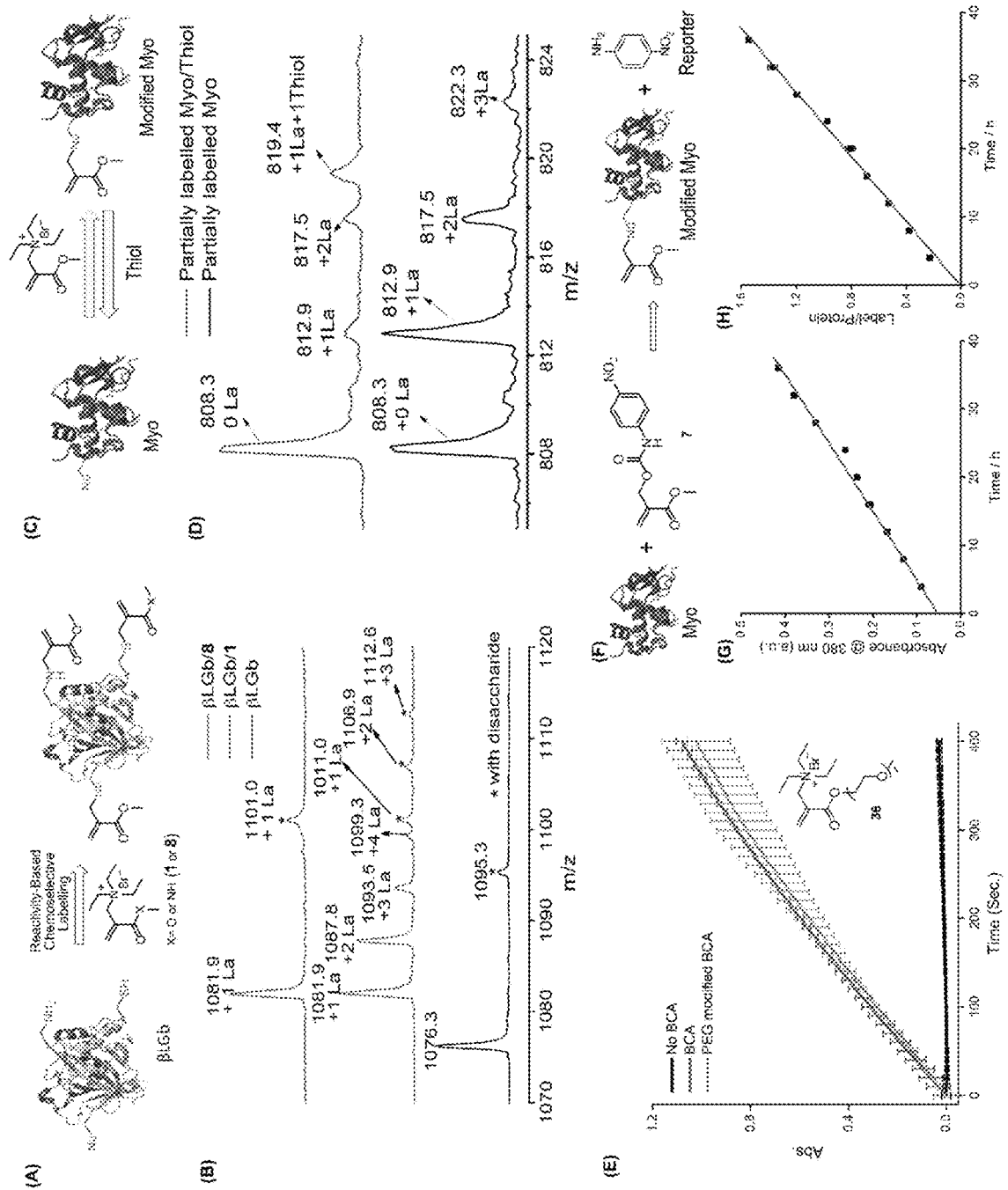
Figure 46:
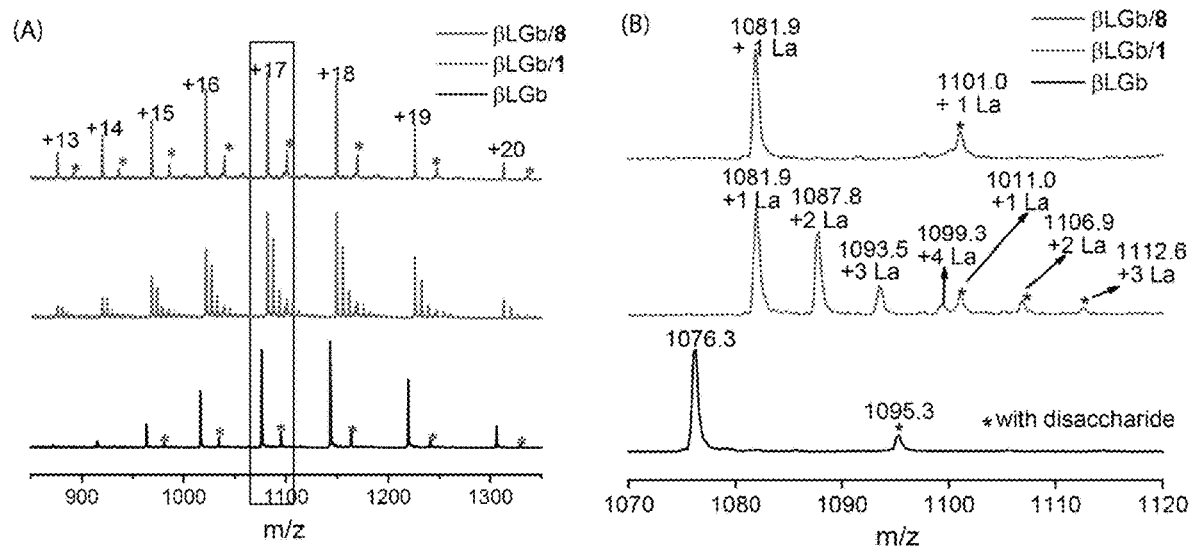
FIG. 46. Mass spectra of compound 1 & 8 modified βLGb. (A) Full mass spectra. Top: βLGb modified with 8. Middle: βLGb modified with 1. Bottom: unmodified βLGb. (B) Corresponding mass spectra of highlighted charge state (+17) in (A). 1 La stands for 1 modification.
Figure 47:
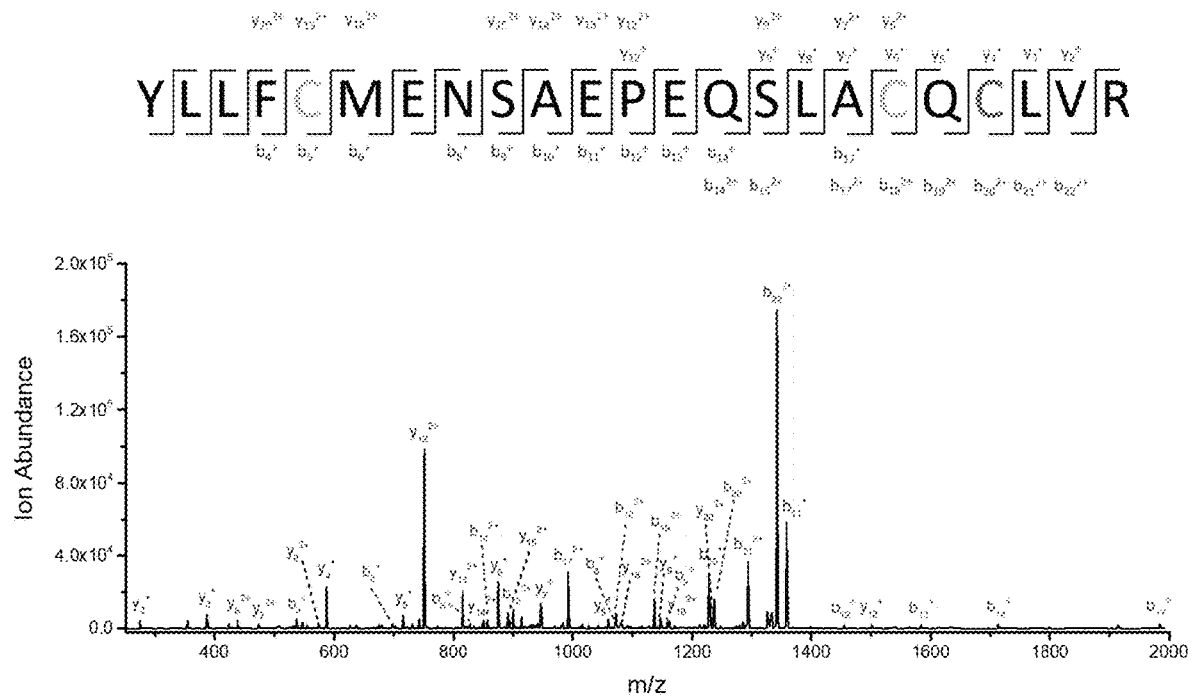
FIG. 47. MS/MS of digested βLGb modified with compound 8 shows selective modification on free cysteine, C121 while no modifications on cysteines involved in disulfide bond.
Figure 48:
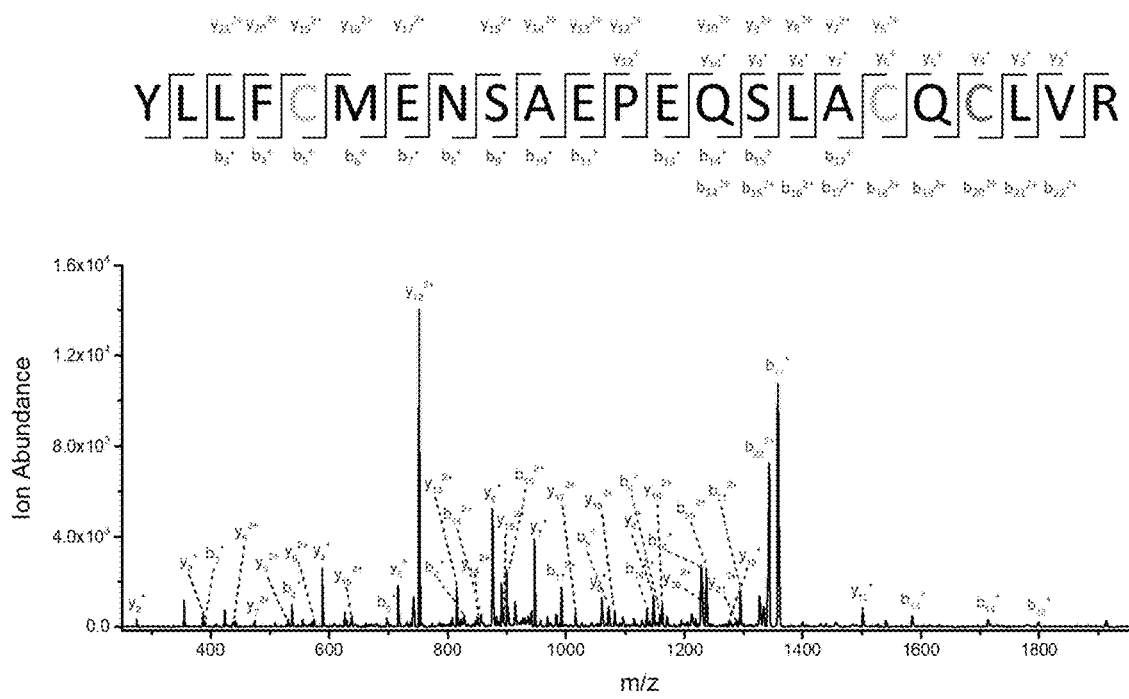
FIG. 48. MS/MS of digested βLGb modified with compound 1 shows modification on free cysteine, C121 while no modifications on cysteines involved in disulfide bond. Figure discloses SEQ ID NO: 3.
Figure 49:
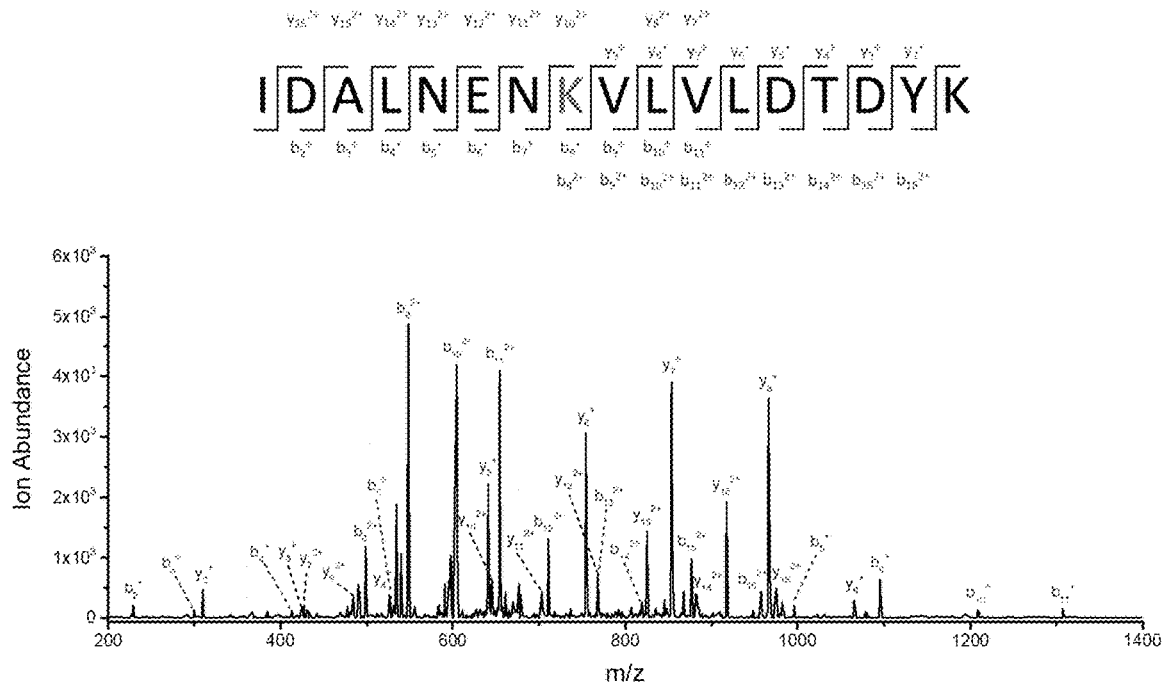
FIG. 49. MS/MS of digested βLGb modified with compound 1 shows unselective modification of lysine K91. Figure discloses SEQ ID NO: 4.
Figure 50:
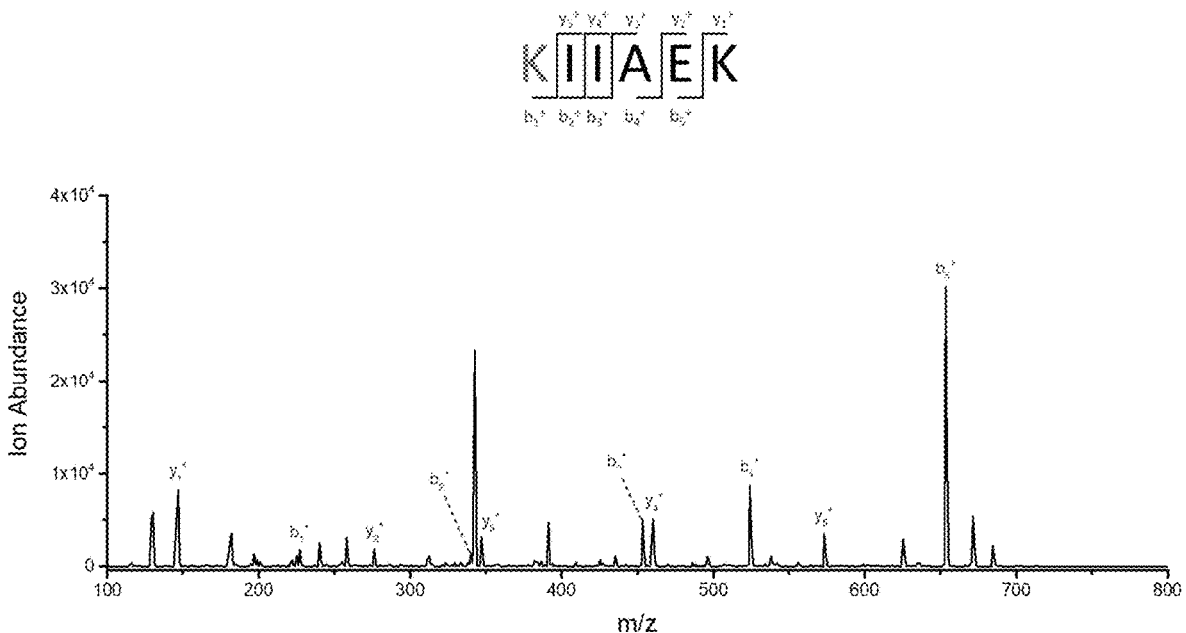
FIG. 50. MS/MS of digested βLGb modified with compound 1 shows unselective modification of lysine K70. Figure discloses SEQ ID NO: 5.
Figure 51:
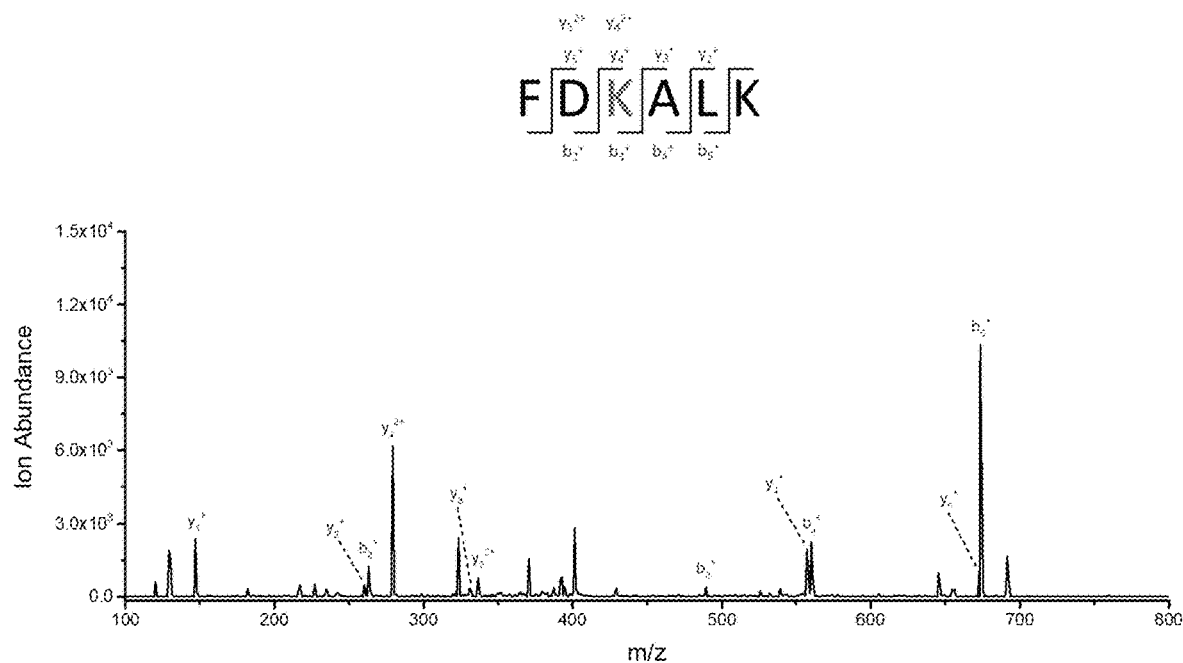
FIG. 51. MS/MS of digested βLGb modified with compound 1 shows unselective modification of lysine K138. Figure discloses SEQ ID NO: 6.
Figure 52:
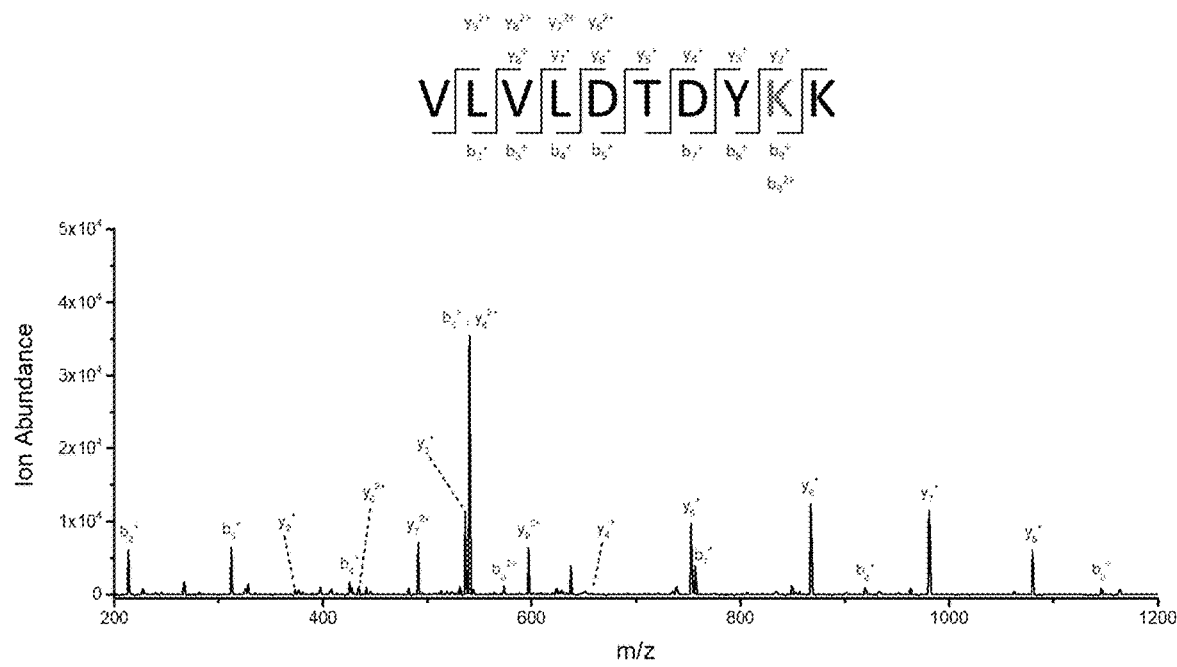
FIG. 52. MS/MS of digested βLGb modified with compound 1 shows unselective modification of lysine K100. Figure discloses SEQ ID NO: 7.
Figure 53:
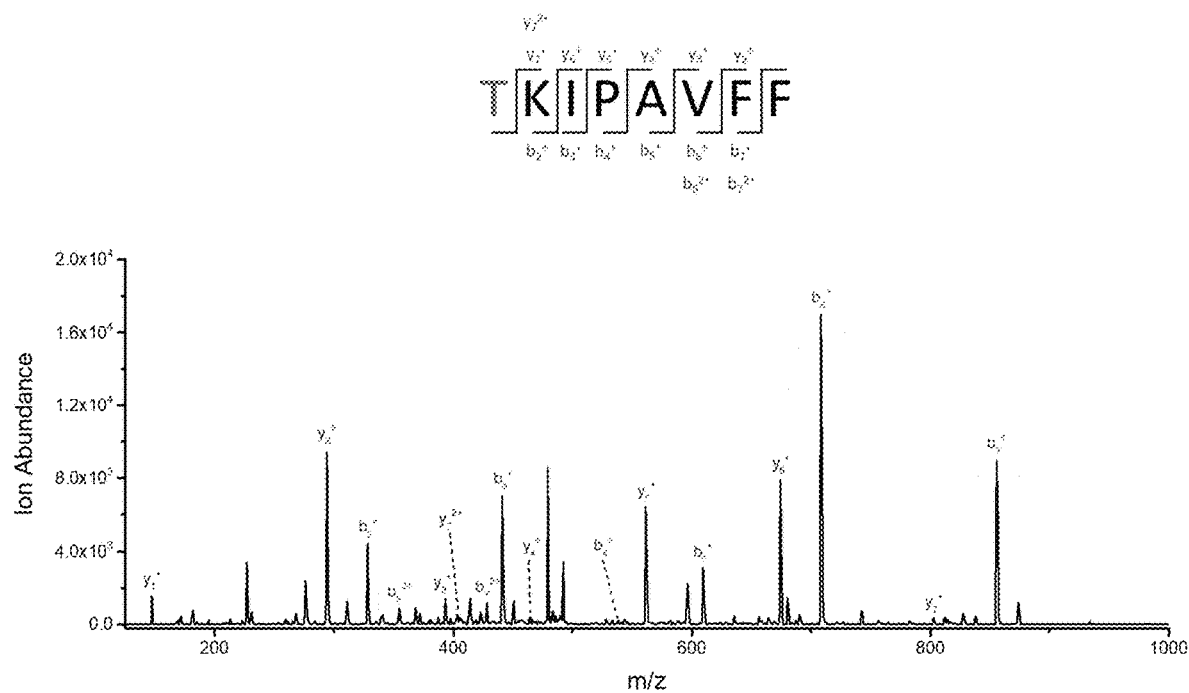
FIG. 53. MS/MS of digested βLGb modified with compound 1 shows unselective modification of lysine T76. Figure discloses SEQ ID NO: 8.
Figure 54:
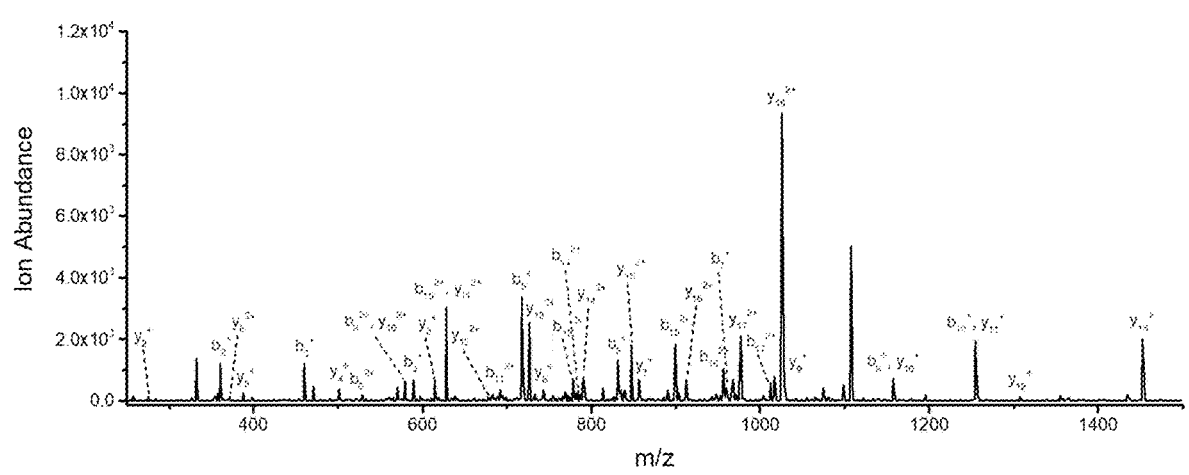
FIG. 54. MS/MS of digested βLGb modified with compound 1 shows unselective modification of lysine Y42. Figure discloses SEQ ID NO: 9.

As illustrated in FIG. 5A, it was envisaged that modifications on multiple nucleophilic residues would occur with the highly reactive 1, while 8 would selectively modify cysteine. βLGb was fully labelled within 5 and 40 minutes, when treated with excess of 1 and 8 respectively, as discerned from the disappearance of the unmodified protein peaks in ESI-MS (FIGS. 5B and 46).

| Sequence of βLGb: | | | |
|---|---|---|---|
| 1-10<br>LIVTQTMKGL | 11-20<br>DIQKVAGTWY | 21-30<br>SLAMAASDIS | 31-40<br>LLDAQSAPLR |
| 41-50<br>VYVEELKPTP | 51-60<br>EGDLEILLQK | 61-70<br>WENGECAQKK | 71-80<br>IIAEKTKIPA |
| 81-90<br>VFKIDALNEN | 91-100<br>KVLVLDTDYK | 101-110<br>KYLLFCMENS | 111-120<br>AEPEQSLACQ |
| 121-130<br>CLVRTPEADD | 131-140<br>EALEKFDKAL | 141-150<br>KALPMHIRLS | 151-160<br>FNPTQLEEQC |
| 161-162<br>HI | | | |

The mass shift in the concurrently appearing new peaks correspond to one to four modifications in βLGb, when treated with 1. Multiple modifications indicate that 1 is non-selective in labeling the protein. In contrast, only a single new peak corresponding to the protein with one modification was found in βLGb labelled with 8. To further pinpoint modification sites on βLGb, modified proteins were digested and subjected to MS/MS analysis. Indeed, only the free cysteine site was modified with 8 (FIGS. 47-54). With 1 however, modifications of other nucleophilic residues including lysine, tyrosine and threonine were found. Interestingly, the primary amine of lysine was not double-labeled, as seen with small molecule nucleophiles. This is likely due to the competition from other nucleophilic residues.

Figure 55:
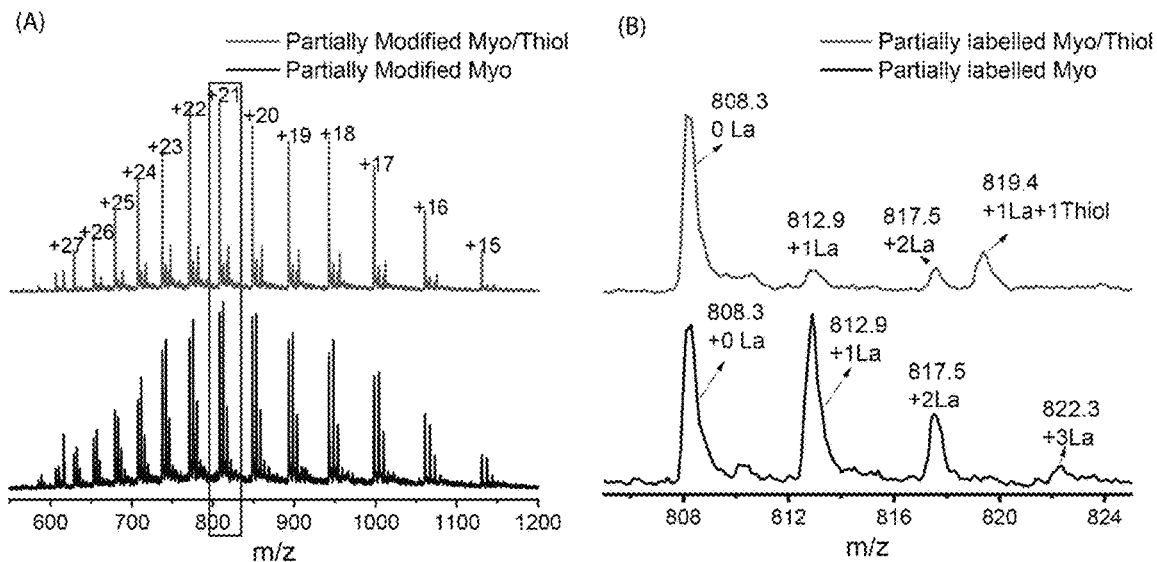
FIG. 55. Mass spectra of compound 1 treated myoglobin followed by incubation with and without thiol. (A) Full mass spectra with all charge states. (B) Corresponding mass spectra of highlighted charge state (+21) in (A). 1 La stands for 1 modification.

As with the small molecules above, the reversibility of the covalent modification of the proteins was also tested, as this possibility has implications in especially for protein delivery applications. Myoglobin (Myo) was modified with 1, followed by incubation with 10 equivalents of thiol for 2 hours (FIG. 5C). Multiple modifications were observed on myoglobin, when treated with 1 (FIGS. 5D and 55). Modified proteins were subsequently reversed to unmodified myoglobin after incubating with a thiol, as shown by the intensity reduction of modified protein peaks accompanied by an increase in that of the unmodified protein peak. The extent of recovery is consistent with that observed in the small molecule study above.

Figure 56:
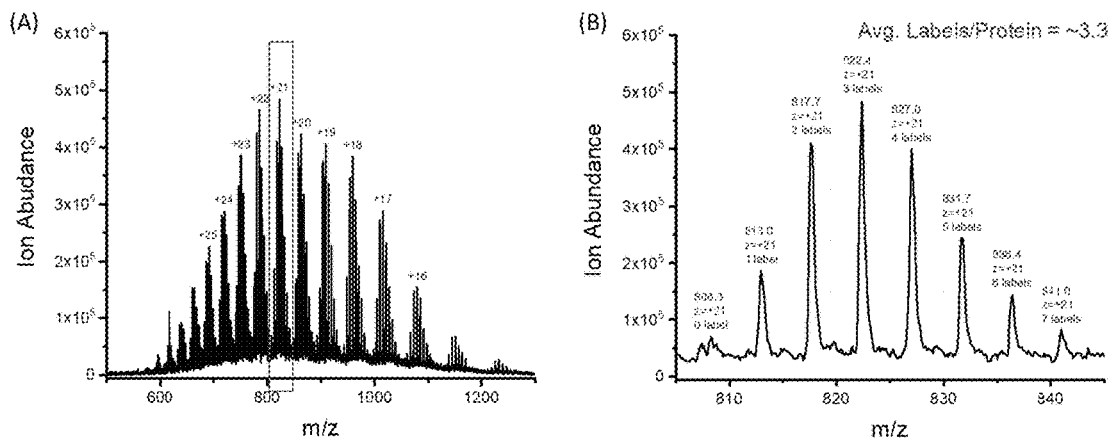
FIG. 56. Mass spectra of myoglobin modified with compound 1. Left: whole mass spectrum. Right: Mass spectrum on +21 charge state.
Figure 57:
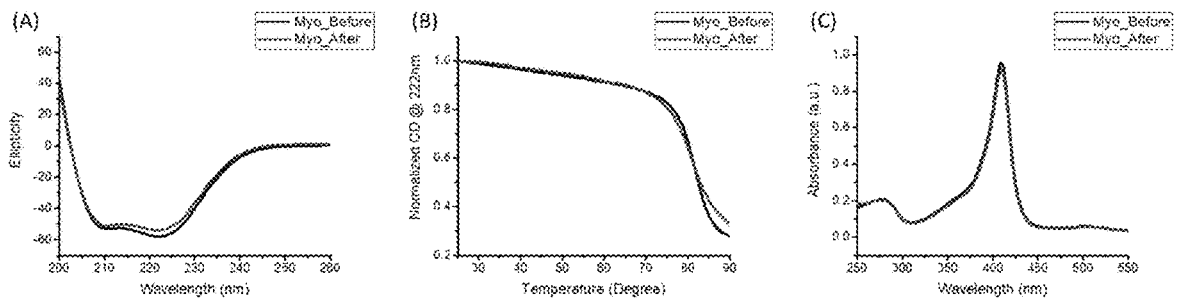
FIG. 57. Biophysical characterization of myoglobin before and after modification using 1. (A) CD, (B) Melting point; (C) UV-visible absorption spectrum of Heme FIG. 58. Mass spectrum of bovine carbonic anhydrase (BCA) treated with compound 36. (A) Full mass spectrum of BCA modified with 36. (B) Mass spectrum of highlighted m/z region as an example to analyze the modification. Charge states are color coded with the dots. The average modification for each protein is ~3.1.
Figure 58:
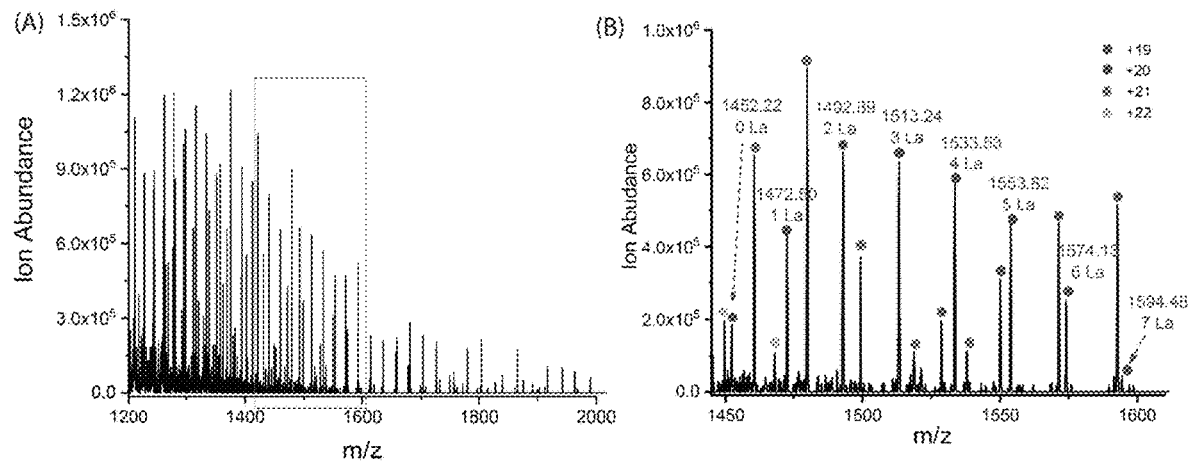

To assess the influence of the covalent modification on protein structures, Myo with ~3 modifications was investigated for changes CD spectroscopy, melting temperature and absorption spectrum of heme region (FIGS. 56 and 57). The lack of any significant change in Myo's physical properties shows that the modification has negligible effect on protein structures. Similarly, modified bovine carbonic anhydrase (BCA) (with ~3 modifications using 36) did not exhibit any effect on its enzymatic activity (FIGS. 5E and 58).

Additionally, with regard to the ability to simultaneously quantify protein labeling within this reaction format itself, modification of Myo with 7 was tested, where a nucleophile induced click-to-release reaction would form 4-nitroaniline, the absorbance of which can report on the extent of protein modification (FIG. 5F). The correlation between the molecular release and the extent of protein modification was indeed clear (FIG. 5G-5H).

Figure 6:
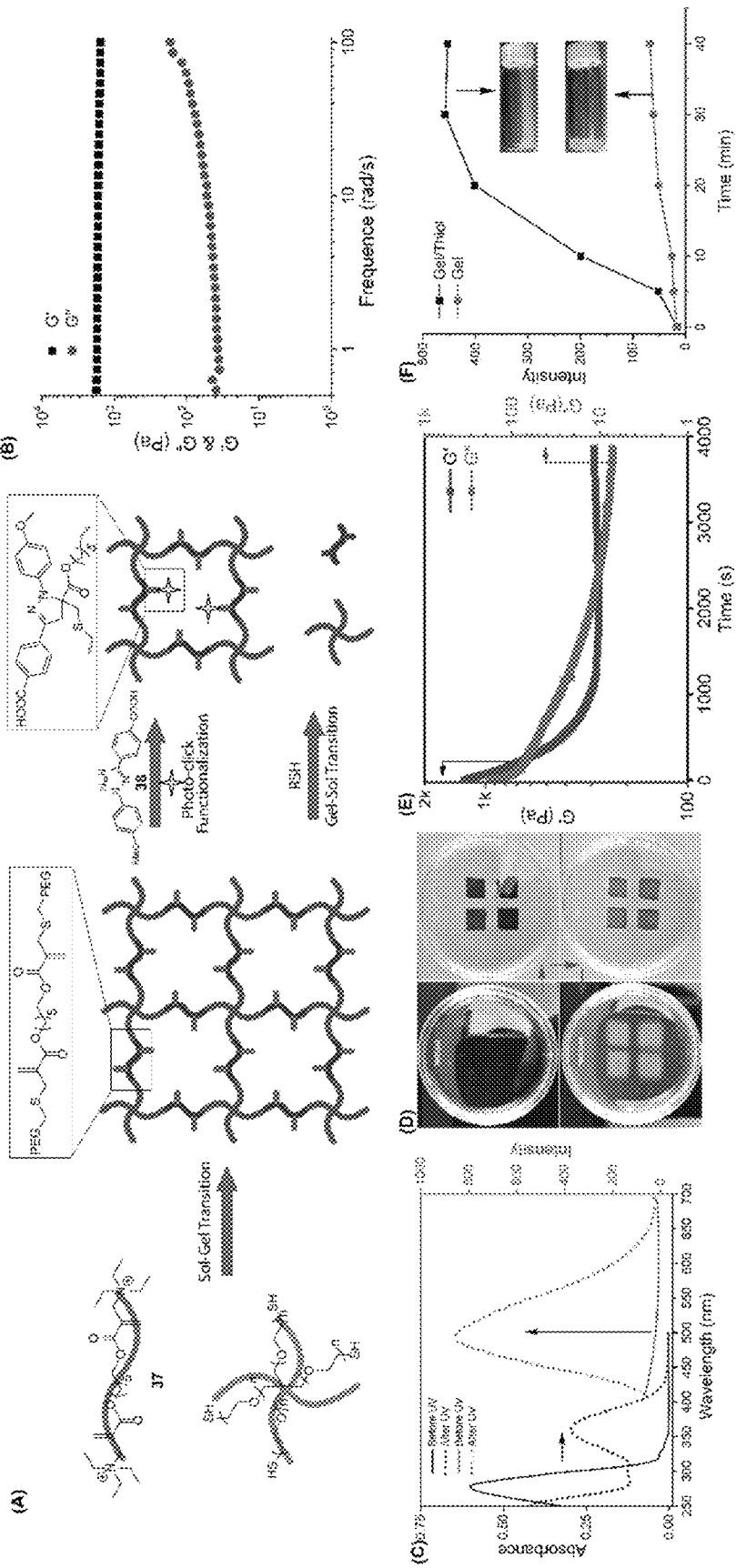
FIG. 6. Thiol-click for switchable hydrogel. (A) Illustration of hydrogel network formation and orthogonal manipulation on post-gelation properties. (B) Frequency sweep of storage modulus (G') and loss modulus (G") of pre-cured hydrogel. (C) Tetrazole photo-click with 9 followed by Uv-vis and fluorescent spectroscopy. (D) Images of photo-patterning hydrogel. Top left: Hydrogel before tetrazole addition; top right: Addition of tetrazole to hydrogel above pattern-masked UV lamp. Bottom right: Hydrogel with tetrazole exposed to UV irradiation for 2 minutes. Bottom left: Patterned hydrogel after removal of unreacted tetrazole. (E) In situ rheological measurement on thiol-triggered hydrogel dissolution. (F) Hydrogel for cargo encapsulation and thiol-triggered release measured by the evolution of fluorescence in the supernatant. Inset: corresponding photographs of hydrogel incubated with and without thiol.

Chemical orthogonality is often the key to achieving functional complexity in advanced functional materials. To demonstrate the potential impact of thiol-click chemistry on preparation of functional materials, the reaction was utilized to synthesize orthogonally functionalizable hydrogels (FIG. 6A). Hydrogels were prepared in under a minute by mixing two components, a thiol-functionalized 4-arm PEG and a bifunctional ammonium crosslinker, 37. Formation of hydrogel network was evidenced by the dominant storage modulus (G') over loss modulus (G") (FIG. 6B). Though the thiol-click crosslinking converted the activated Michael acceptor to a deactivated one, the population of alkene was always constant in hydrogel network. In coupling with tetrazole photo-click chemistry, these alkenes can be used as a handle for post-gelation functional engineering. Since the photo-click product offers a fluorescent chromophore, the reaction can be followed by absorption and fluorescence spectroscopy. (Yu, et al. 2013 *J. Am. Chem. Soc.* 135, 16766-16769.)

Indeed, occurrence of reaction was observed by photoirradiation-induced distinct red-shift and fluorescence generation (FIG. 6C). Further, photo-patterning on hydrogels was conveniently accessed by simply irradiating the pattern-masked hydrogel for 2 minutes (FIG. 6D). These results show that additional functionalities can be conveniently introduced into the hydrogel.

These click reactions were shown that they can be reversed and chemical reversal in the case of hydrogels caused them to uncrosslink and dissolve away the gel. Addition of hexaethyleneglycol-monomethyl-ether thiol triggered the dissolution of hydrogel, causing a significant loss in both storage and loss modulus (FIG. 6E).

Figure 59:
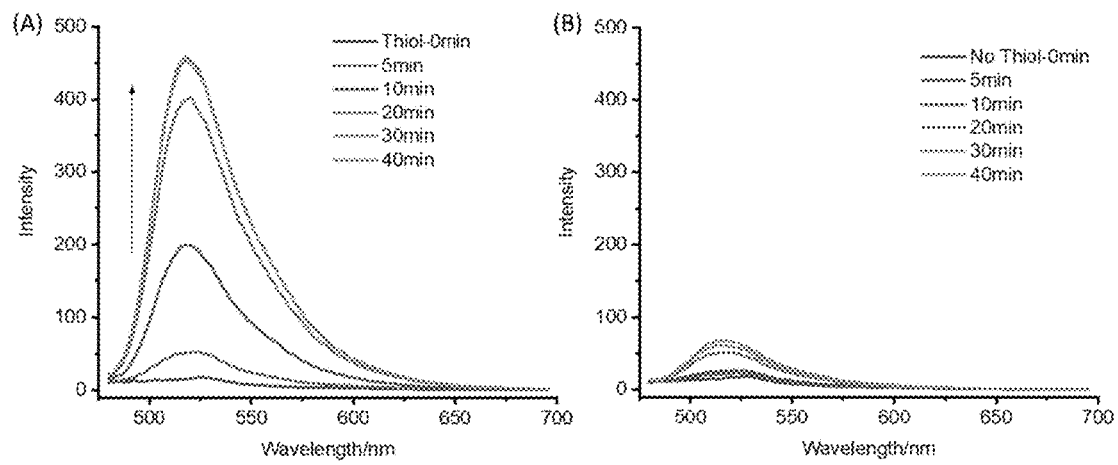
FIG. 59. BSA release followed by fluorescence in the presence(A) and absence(B) of thiol.

To further demonstrate the utility of such a process, bovine serum aOumin (BSA) was encapsulated within these hydrogels during the formation of the gel. Dissolution of hydrogel caused the release of fluorescently-tagged BSA from the hydrogel incubated with thiol containing phosphate buffer. Increasing fluorescence intensity in the liquid phase was observed indicating that entrapped BSA can rapidly diffuse from gel phase to the liquid phase in the presence of thiol due to gel dissolution. In contrast, the diffusion of BSA from hydrogel to liquid phase was much slower when the gel was intact in the absence of thiol (FIGS. 6F and 59).

EXPERIMENTAL

Materials and Instrumentation

All reagents were used as received from commercial sources unless otherwise mentioned. $^1$H NMR, $^{13}$C NMR spectra were recorded on a Brucker 400 MHz NMR spectrometer. UV-Vis spectra were recorded on PerkinElmer Lambda 35 UV/Vis spectrometer. Fluorescent spectra were obtained from PerkinElmer LS 55 fluorescence spectrometer. Protein labeling and quantification were carried out on Biodrop microvolume UV-Vis spectrophotometer. Mass spectra were recorded on a Bruker AmaZon quadrupole ion trap mass spectrometer coupled with electrospray ionization source or a Thermo Orbitrap Fusion tribrid (quadrupole, orbitrap, and ion trap) mass spectrometer coupled with Easy nLC 1000 nanoLC system. Rheological measurements were performed by a Malvern Kinexus Pro rheometer.

Synthesis

Synthesis of compound 1b: Briefly, compound 1a (2.0 g, 17.23 mmol) was dissolved in 20 mL of dry DCM and cooled to 0° C. in ice bath. PBr$_3$ (2.332 g, 8.615 mmol) was added slowly to the solution. Then the reaction mixture was stirred at room temperature. The completion of reaction was monitored by TLC. The reaction was then quenched by the addition of ice. The reaction solution was neutralized by sodium bicarbonate solution and then extracted with DCM three times. Organic layers were collected and dried over anhydrous sodium sulfate, then concentrated. Compound 1b was obtained by flash chromatography. Yield: 2.52 g, 82%. $^1$H-NMR (400 MHz, CDCl$_3$): δ 6.34 (s, 1H), 5.96 (s, 1H), 4.18 (s, 2H), 3.82 (s, 3H).

Synthesis of compound 1. Compound 1b (50 mg, 0.28 mmol) was dissolved in 200 μL of dry THF. To the solution, triethylamine (57 mg, 0.56 mmol) was added. The reaction was allowed to stirred at room temperature for 2 hours. Then mixture was concentrated and precipitated in dry diethyl ether for 3 times. The precipitate was collected and dried to afford compound 1. Yield: 65 mg, 83%. $^1$H-NMR (400 MHz, MeOH-d4): δ (ppm) 6.90 (s, H), 6.40 (s, H), 4.23 (s, 2H), 3.85 (s, 3H), 3.30 (q, J=7.2 Hz, 6H), 1.37 (t, J=7.2 Hz, 9H). $^{13}$C-NMR (100 MHz, MeOH-d4): δ (ppm) 167.42, 140.52, 130.66, 56.97, 54.30, 53.44, 8.08. MS (m/z): [M]$^+$ calcd. for C$_{11}$H$_{22}$BrNO$_2$, 279.08; found, 200.4 for [M−Br]$^+$

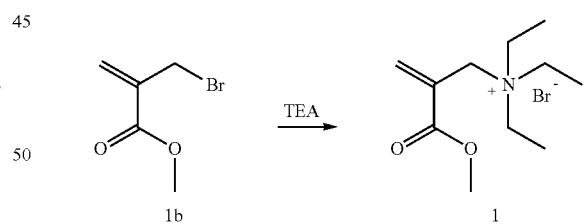

Synthesis of compound 2. Compound 1b (25 mg, 0.14 mmol) was weighed to glass vial. To the vial, tripropylamine (40 mg, 0.28 mmol) was added. The reaction was kept for 2 hours at room temperature. Then the white precipitate was washed with diethyl ether for three times. The precipitate was collected and dried to achieve compound 2. Yield: 32.1 mg, 71%. $^1$H-NMR (400 MHz, MeOH-d4): δ (ppm) 6.90 (s, 1H), 6.36 (s, 1H), 4.27 (s, 2H), 3.85 (s, 3H), 3.15 (p, J=6.2 Hz, 6H), 1.81 (m, 6H), 0.99 (t, J=9.1 Hz, 9H). $^{13}$C-NMR (100 MHz, MeOH-d4): δ (ppm) 166.04, 139.16, 129.44, 60.00, 57.31, 52.09, 15.27, 9.31. MS (m/z): [M]$^+$ calcd. for C14H$_{28}$BrNO$_2$, 321.13; found, 242.3 for [M−Br]$^+$.

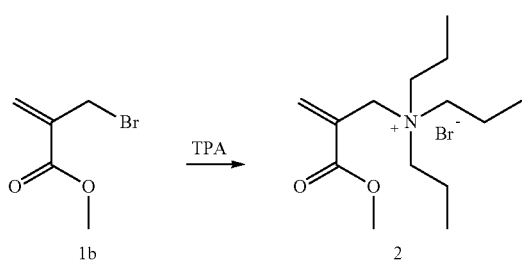

Synthesis of compound 3. Compound 1b (25 mg, 0.14 mmol) was weighed to glass vial. To the vial, N, N-diisopropylethylamine (36.2 mg, 0.28 mmol) was added. The reaction was kept for 2 hours at room temperature. Then the white precipitate was washed with diethyl ether for three times. The precipitate was collected and dried to achieve compound 3. Yield: 35.7, 83%. $^1$H-NMR (400 MHz, MeOH-d4): δ (ppm) 6.83 (s, 1H), 6.46 (s, 1H), 4.23 (s, 2H), 4.16 (m, 2H), 3.87 (s, 3H), 3.46 (q, J=7.30 Hz, 2H), 1.51 (q, J=3.0 Hz, 12H), 1.40 (t, J=7.75 Hz, 3H). $^{13}$C-NMR (100 MHz, MeOH-d4): δ (ppm) 166.48, 138.62, 131.19, 62.66, 57.00, 52.16, 17.65, 17.21, 8.76. MS (m/z): [M]$^+$ calcd. for $C_{13}H_{26}BrNO_2$, 307.11; found, 228.4 for [M−Br]$^+$.

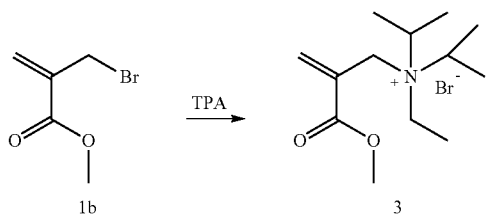

Synthesis of compound 4. Compound 1b (25 mg, 0.14 mmol) was weighed to glass vial. To the vial, pyridine (22.1 mg, 0.28 mmol) was added. The reaction was kept for 2 hours at room temperature. Then the white precipitate was washed with diethyl ether for three times. The precipitate was collected and dried to achieve compound 4. Yield: 30.1 mg, 83%. $^1$H-NMR (400 MHz, MeOH-d4): δ (ppm) 9.06 (d, J=5.6 Hz, 2H), 8.63 (t, J=7.8 Hz, 1H), 8.14 (t, J=7.1 Hz, 2H), 6.67 (s, 1H), 6.36 (s, 1H), 5.53 (s, 2H) 3.75 (s, 1H). $^{13}$C-NMR (100 MHz, MeOH-d4): δ (ppm) 166.29, 147.56, 146.52, 134.89, 134.83, 62.94, 53.03. MS (m/z): [M]$^+$ calcd. for $C_{10}H_{12}BrNO_2$, 257.01; found, 178.4 for [M−Br]$^+$.

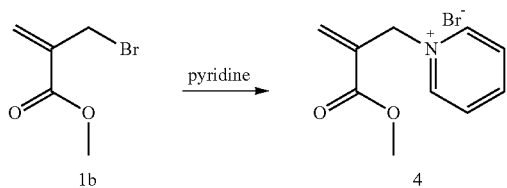

Synthesis of compound 5. 4-(dimethylamino) pyridine (24.4 mg, 0.2 mmol) was dissolved in 100 μL of dry THF. To the solution, compound 1b (50 mg, 0.28 mmol) was added. The reaction was kept for 2 hours at room temperature. Then the white precipitate was washed with diethyl ether for three times. The precipitate was collected and dried to achieve compound 5. Yield: 53.2 mg, 89%. $^1$H-NMR (400 MHz, MeOH-d4): δ 8.16 (d, J=7.79 Hz, 2H), 6.99 (d, J=7.79 Hz, 2H), 6.52 (s, 1H), 6.08 (s, 1H), 5.02 (s, 2H), 3.76 (s, 3H), 3.26 (s, 6H).13C-NMR (100 MHz, MeOH-d4): δ (ppm) 166.53, 158.10, 143.43, 136.17, 132.28, 108.76, 58.93, 52.87, 40.36. MS (m/z): [M]$^+$ calcd. for $C_{12}H_{17}BrNO_2$, 300.05; found, 221.3 for [M−Br]$^+$.

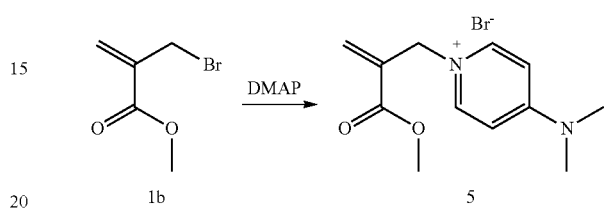

Synthesis of compound 6. Compound 1b (232 mg, 2 mmol) was dissolved in 5 mL of DCM with TEA (220 mg, 2 mmol) and cooled to 0° C. To the solution, acetyl chloride (157 mg, 2 mmol) was added dropwise. The reaction mixture was stirred at room temperature after addition. After reaction, the reaction solution was collected by filtration and extracted with water for three times. The organic layers were collected and dried over anhydrous sodium sulfate. The solution was further filtered and concentrated to afford crude product which was subjected to flash chromatography to obtain pure compound 6. Yield: 224.4 mg, 71%. $^1$H-NMR (400 MHz, CDCl$_3$): δ 6.36 (s, 1H), 5.85 (s, 2H), 4.81 (s, 2H), 3.79 (s, 3H), 2.10 (s, 3H). $^{13}$C-NMR (100 MHz, CDCl$_3$): δ (ppm) 170.41, 165.68, 135.21, 127.60, 62.47, 52.06, 20.88.

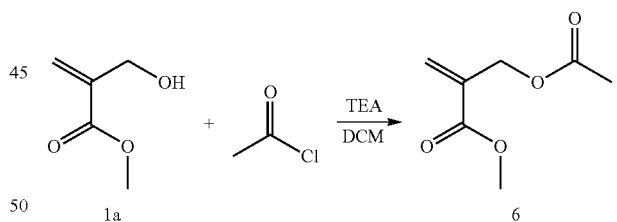

Synthesis of compound 7. Compound 1b (116 mg, 1 mmol) was dissolved in 5 mL of THF with 4-nitrophenyl isocyanate (164.1 mg, 1 mmol) and 2,6-Di-tert-butyl-4-methylphenol (2.2 mg, 0.01 mmol). The reaction mixture was heated at 60° C. under argon atmosphere. The completion of reaction was followed by TLC. Compound 7 was obtained by flash chromatography. Yield: 134 mg, 48%. $^1$H-NMR (400 MHz, MeOH-d4): δ (ppm) 8.19 (d, 2H), 7.67 (d, 2H), 6.37 (d, 1H), 5.98 (d, 1H), 4.91 (s, 2H), 3.79 (s, 3H). $^{13}$C-NMR (100 MHz, MeOH-d4): δ (ppm) 165.71, 153.21, 145.29, 142.54, 135.75, 126.75, 124.45, 117.50, 62.88, 51.13. MS (m/z): [M]$^+$ calcd. for $C_{12}H_{12}N_2O_6$, 280.07; found, 303.1 for [M+Na]$^+$.

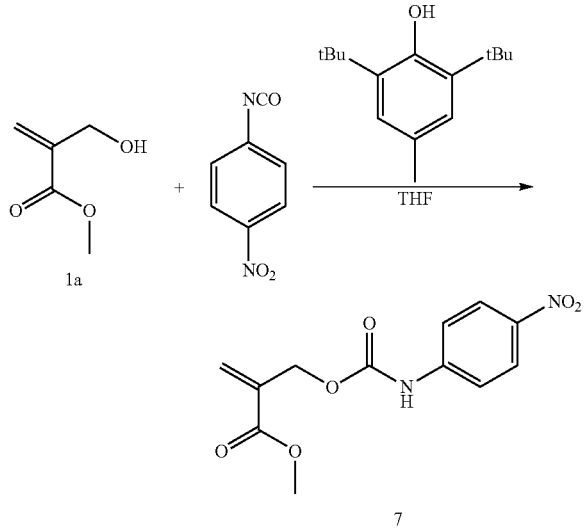

7

Synthesis of Compound 8, 9, 10

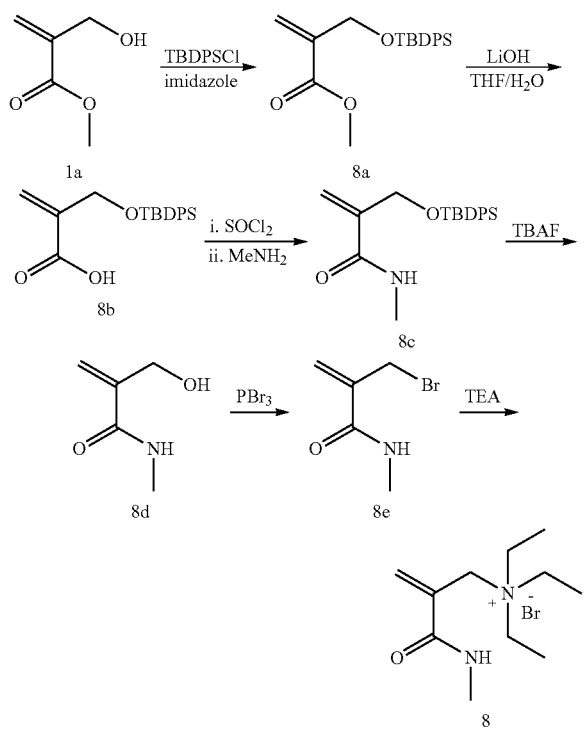

Synthesis of compound 8a. Compound 1a (3.48 g, 30 mmol) was dissolved in 50 mL of dry THF with imidazole (2.250 g, 33 mmol). TBDPSCl (9.070 g, 33 mmol) was added to the solution dropwise at 0° C. The reaction was stirred overnight at room temperature. Then, precipitate was removed by filtration to achieve clear solution which was further extracted with saturated sodium bicarbonate solution, water and brine. The organic layers were combined and dried over anhydrous sodium sulfate. The solution was collected, concentrated and subjected to flash chromatography to afford compound 8a. Yield, 6.99 g, 66%. $^1$H-NMR (400 MHz, CDCl$_3$): δ (ppm) 7.64-7.69 (m, 4H), 7.34-7.47 (m, 6H), 6.33(q, J=1.9 Hz, 1H), 6.11(q, J=1.9 Hz, 1H), 4.42 (t, J=2.1 Hz, 2H), 3.70 (s, 3H), 1.08 (s, 9H). $^{13}$C-NMR (100 MHz, CDCl$_3$): δ (ppm) 166.25, 139.33, 135.46, 133.24, 129.78, 127.77, 124.09, 62.21, 51.63, 26.82, 19.30. MS (m/z): [M]$^+$ calcd. for C$_{21}$H$_{26}$O$_3$Si, 354.17; found, 377.1 for [M+Na]$^+$.

Synthesis of compound 8b. Compound 8b (5 g, 14.15 mmol) was dissolved in 50 mL of THF/H$_2$O mixture (1:1). Lithium hydroxide (1.015 g, 42.45 mmol) in 2 mL of water was added to the solution. The reaction was stirred overnight. Then, the solution was acidified with 2M HCl solution to pH 3 and extracted with DCM. Organic layers were collected and dried over anhydrous sodium sulfate. The organic layer was further concentrated to obtain crude product, compound 8b which was subjected for reaction without further purification. Yield: 3.925 g, 82%. $^1$H-NMR (400 MHz, CDCl$_3$): δ (ppm) 7.62-7.68 (m, 4H), 7.34-7.46 (m, 6H), 6.43 (s, 1H) 6.18 (s, 1H), 4.40 (q, 0.92 Hz, 2H), 1.08 (s, 9H). $^{13}$C-NMR (100 MHz, CDCl$_3$): δ (ppm) 169.70, 138.42, 135.44, 133.00, 129.86, 127.80, 126.47, 62.06, 26.80.19.28. MS (m/z): [M]$^+$ calcd. for C$_{20}$H$_{24}$O$_3$Si, 340.15; found, 363.1 for [M+Na]$^+$.

Synthesis of compound 8c. To 50 mL of compound 8b (2.620 g, 8.13 mmol) solution in THF, thionyl chloride (19.4 g, 160.26 mmol) was added. The mixture was refluxed for 3 hours. Then volatiles were removed under vacuum. The residue was dissolved in 10 mL of dry DCM in a round bottom flask. To the flask, a solution of methylamine (4.13 mL 2M THF solution, 8.13 mmol) and TEA (0.828 g, 8.13 mmol) in 10 mL DCM was added dropwise at 0° C. The reaction was stirred overnight at room temperature. The white precipitate was removed by filtration. Solvent was removed and the residue was extracted with sodium bicarbonate, and water using ethyl acetate. The organic layers were combined and dried over anhydrous sodium sulfate. The solution was collected and dried for flash chromatography. Pure compound 8c was obtained after purification. Yield: 2.60 g, 95%. $^1$H-NMR (400 MHz, CDCl$_3$): 7.62-7.69 (m, 4H), 7.36-7.48 (m, 6H), 6.84 (bs, NH), 5.98 (s, 1H), 5.36 (d, J=1.28 Hz, 1H), 4.41 (s. 2H), 2.89 (d, J=4.88 Hz, 3H), 1.07 (s, 9H).

Synthesis of compound 8d. To 10 mL of compound 8c (2.50 g, 7.08 mmol) solution, 7.79 mL of TBAF solution (1M in THF) was added dropwise at 0° C. The reaction completed in 20 minutes. Compound 8d was obtained by flash chromatography. Yield: 513 mg, 63%. $^1$H-NMR (400 MHz, MeOH-d4): 5.80 (d, J=0.74 Hz, 1H), 5.58 (d, J=1.05 Hz, 1H), 4.27 (s, 2H), 2.79 (s, 3H). $^{13}$C-NMR (100 MHz, MeOH-d4): 169.06, 143.76, 118.13, 61.22, 24.94.

Synthesis of compound 8e. To the solution of compound 8d (230 mg, 2 mmol) in 5 mL of dry DCM, PBr$_3$ (270 mg, 1 mmol) was added slowly at 0° C. The reaction was stirred at room temperature after addition. The completion of reaction was followed by TLC. Then reaction was quenched by addition of 2 M sodium bicarbonate solution. The solution was further extracted with DCM and water for two more times, and organic layers were combined and dried over anhydrous sodium sulfate. The solution was collected and dried to afford compound 8e for further reaction.

Synthesis of compound 8. Compound 8e (35.6 mg, 0.2 mmol) was weighed into a small glass vial. To the vial, triethylamine (44.48 mg, 0.44 mmol) was added. The reaction was kept for 2 hours at room temperature. Then the white precipitate was washed with diethyl ether for three times. The precipitate was collected and dried to achieve compound 8. Yield: 42 mg, 75%. $^1$H-NMR (400 MHz, MeOH-d4): 6.24 (s, 1H), 6.07 (s, 1H), 4.19 (s, 2H), 3.26 (q, J=7.20 Hz, 6H), 2.83 (s, 3H), 1.34 (t, J=7.20 Hz, 9H). $^{13}$C-NMR (100 MHz, MeOH-d4): 168.41, 134.17, 131.35, 56.41, 52.78, 25.18, 6.65. MS (m/z): [M]$^+$ calcd. for $C_{11}H_{23}BrN_2O$, 278.10; found, 199.4 for [M−Br]$^+$.

Synthesis of compound 9. Compound 8d (115 mg, 1 mmol) was dissolved in 1 mL of dry DCM with triethyl amine (101 mg, 1 mmol). The reaction mixture was cooled to 0° C. followed by slow addition of acetyl chloride (78 mg, 1 mmol). Then reaction was stirred at room temperature for 6 hours. The mixture was dried and subjected to flash chromatography to afford pure compound 8d. Yield: 120 mg, 76%. $^1$H-NMR (400 MHz, CDCl$_3$): δ (ppm) 6.12 (bs, NH), 5.94 (s, 1H), 5.61 (s, 1H), 4.82 (d, J=0.76 Hz, 2H), 2.88 (d, J=4.84 Hz, 3H), 2.10 (s, 3H). $^{13}$C-NMR (100 MHz, MeOH-d4): δ (ppm) 170.80, 166.88, 139.39, 122.97, 63.59, 26.61, 21.07. MS (m/z): [M]$^+$ calcd. for $C_7H_{11}NO_3$, 157.07; found, 180.4 for [M+Na]$^+$.

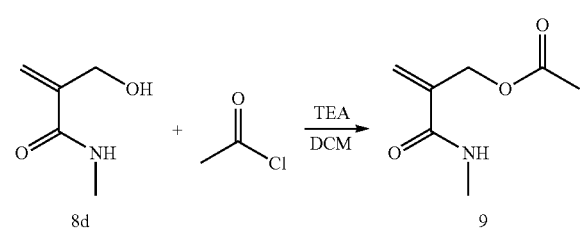

Synthesis of compound 10. Compound 8d (115 mg, 1 mmol) was dissolved in 5 mL of THF with 4-nitrophenyl isocyanate (164.1 mg, 1 mmol) and 2,6-Di-tert-butyl-4-methylphenol (2.2 mg, 0.01 mmol). The reaction mixture was heated at 60° C. under argon atmosphere. The completion of reaction was followed by TLC. Compound 7 was obtained by flash chromatography. Yield: 166 mg, 59%. $^1$H-NMR (400 MHz, MeOH-d4): δ (ppm) 8.18 (m, 2H), 7.67 (m, 2H), 5.91 (s, 1H), 5.72 (t, J=1.91 Hz, 1H), 4.91 (dd, J=0.48 Hz, J=1.91 Hz, 2H), 2.80 (s, 3H). $^{13}$C-NMR (100 MHz, MeOH-d4): δ (ppm) 168.09, 153.23, 145.32, 142.52, 139.66, 124.46, 120.84, 117.49, 63.78, 25.09. MS (m/z): [M]$^+$ calcd. for $C_{12}H_{13}N_3O_5$, 279.09; found, 302.1 for [M+Na]$^+$.

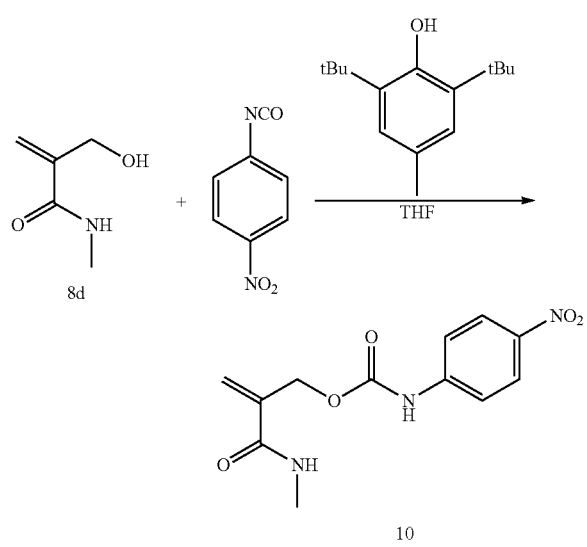

Synthesis of compound 11. 2-(Hydroxy-phenyl-methyl)-acrylic acid methyl ester (403.4 mg, 2.1 mmol) was dissolved in 5 mL dry DCM and cooled to 0° C. To the solution, PBr$_3$ (285 mg, 1.05 mmol) was added slowly. The solution was quenched by addition of 2 M sodium bicarbonate solution. The mixture was extracted using DCM, then washed with water for 2 more times. The organic layer was collected and dried over anhydrous sodium sulfate. The product was obtained after filtration and concentration followed by drying over vacuum. The product was used for next step without purification. Then compound 11a (25.5 mg, 0.1 mmol) was weighed into a small vial followed by addition of triethylamine (20.2 mg, 0.2 mmol). The reaction was kept for 2 hours. The white precipitate was washed with diethyl ether for 3 times and dried to afford compound 11. Yield: 29 mg, 79%. $^1$H-NMR (400 MHz, MeOH-d4): δ (ppm) 8.44 (s, 1H), 7.41-7.58 (m, 4H), 4.47 (s, 2H), 3.92 (s, 3H), 3.11 (q, J=7.16 Hz, 6H), 1.06 (t, J=7.16 Hz, 3H). $^{13}$C-NMR (100 MHz, MeOH-d4): δ (ppm) 168.65, 153.25, 135.49, 130.99, 130.62, 129.66, 123.61, 54.32, 53.61, 51.88, 7.91. MS (m/z): [M]$^+$ calcd. for $C_{11}H_{26}BrO_2$, 355.11; found, 276.2 for [M−Br]$^+$.

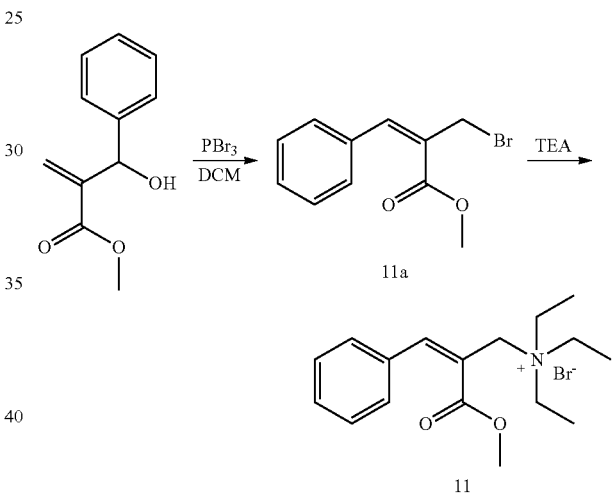

Synthesis of compound 12. Methyl 2-[hydroxy(4-methoxyphenyl) methyl]acrylate (222.2 mg, 1.0 mmol) was dissolved in 5 mL dry DCM and cooled to 0° C. To the solution, PBr$_3$ (142 mg, 0.5 mmol) was added slowly. The solution was quenched by addition of 2 M sodium bicarbonate solution. The mixture was extracted using DCM, then washed with water for 2 more times. The organic layer was collected and dried over anhydrous sodium sulfate. The product was obtained after filtration and concentration followed by drying over vacuum. The product was used for next step without purification. Then compound 12a (28.5 mg, 0.1 mmol) was weighed into a small vial followed by addition of triethylamine (20.2 mg, 0.2 mmol). The reaction was kept for 2 hours. The white precipitate was washed with diethyl ether for 3 times and dried to afford compound 12. Yield: 29 mg, 75%. $^1$H-NMR (400 MHz, MeOH-d4): δ (ppm) 8.35 (s, 1H), 7.45 (m, 2H), 7.08 (m, 2H), 4.52 (s, 2H), 3.90 (s, 3H), 3.86 (s, 3H), 3.14 (q, J=7.17 Hz, 6H), 1.12 (t, J=7.17 Hz, 3H). $^{13}$C-NMR (100 MHz, MeOH-d4): δ (ppm) 168.96, 162.72, 153.01, 131.88, 127.39, 121.51, 116.01, 55.99, 54.31, 53.47, 52.20, 8.05. MS (m/z): [M]$^+$ calcd. for $C_{18}H_{28}BrO_3$, 385.13; found, 306.1 for [M−Br]$^+$.

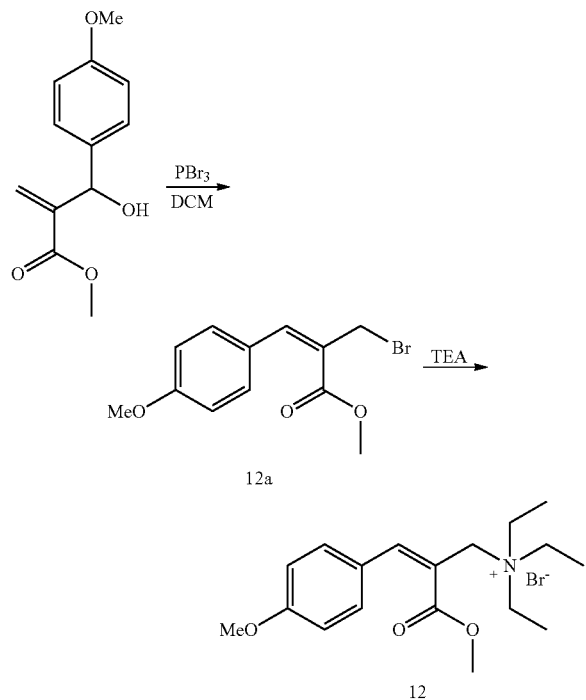

12a

12

Synthesis of compound 13. Methyl 2-[hydroxy (4-bromophenyl) methyl]acrylate (271.1 mg, 1.0 mmol) was dissolved in 5 mL dry DCM and cooled to 0° C. To the solution, PBr$_3$ (142 mg, 0.5 mmol) was added slowly. The solution was quenched by addition of 2 M sodium bicarbonate solution. The mixture was extracted using DCM, then washed with water for 2 more times. The organic layer was collected and dried over anhydrous sodium sulfate. The product was obtained after filtration and concentration followed by drying over vacuum. The product was used for next step without purification. Then compound 13a (33.4 mg, 0.1 mmol) was weighed into a small vial followed by addition of triethylamine (20.2 mg, 0.2 mmol). The reaction was kept for 2 hours. The white precipitate was washed with diethyl ether for 3 times and dried to afford compound 11. Yield: 38 mg, 88%. $^1$H-NMR (400 MHz, MeOH-d4): δ 8.34 (s, 1H), 7.71 (m, 2H), 7.39 (m, 2H), 4.45 (s, 2H), 3.92 (s, 3.92), 3.13 (q, J=7.20 Hz, 6H), 1.09 (t, J=7.20 Hz, 9H). $^{13}$C-NMR (100 MHz, MeOH-d4): 168.48, 151.88, 134.42, 133.81, 131.61, 125.19, 124.13, 54.39, 53.68, 51.93, 7.97. MS (m/z): [M]$^+$ calcd. for C$_{17}$H$_{25}$Br$_2$NO$_2$, 331.90; found, 354.8 for [M+Na]$^+$.

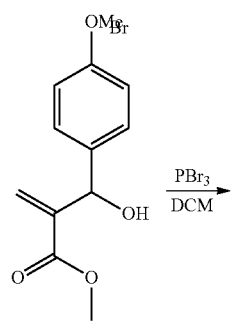

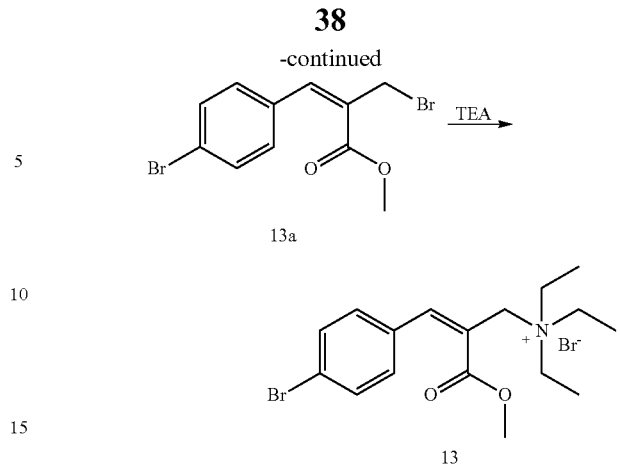

13a

13

Synthesis of compound 14. 2-(Hydroxy-phenyl-methyl)-acrylic acid methyl ester (192 mg, 1.0 mmol) was dissolved in 1 mL of DCM with triethylamine (101.2 mg, 1.0 mmol) and cooled to 0° C. Acetyl chloride (78.5 mg, 1.0 mmol) was added to the solution slowly. Completion of reaction was monitored by TLC. The reaction mixture was extracted using DCM and water. The organic layer was collected and dried over anhydrous sodium sulfate followed by filtration. The solution was then concentrated and subjected to flash chromatography to afford compound 14. Yield: 162 mg, 69%. $^1$H-NMR (400 MHz, CDCl$_3$): δ (ppm) 7.27-7.41 (m, 5H), 6.68 (s, 1H), 6.40 (s, 1H), 5.86 (s, 1H), 3.71 (s, 3H), 2.11 (s, 3H). $^{13}$C-NMR (100 MHz, CDCl$_3$): δ (ppm) 169.57, 165.57, 139.80, 137.93, 128.61, 128.54, 127.82, 125.93, 73.26, 52.15, 21.25.

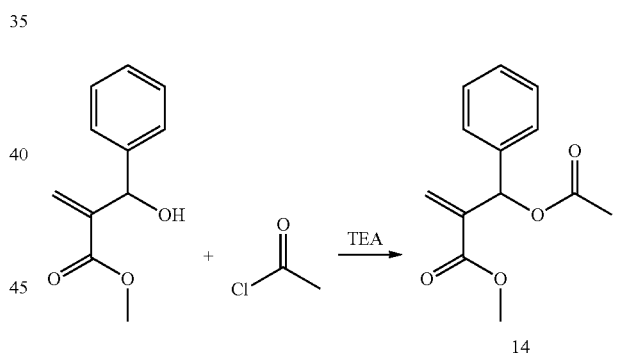

14

Synthesis of compound 15. Methyl 2-[hydroxy (4-methoxyphenyl) methyl]acrylate (444.4 mg, 2.0 mmol) was dissolved in 4 mL of DCM with triethylamine (202.4 mg, 2.0 mmol) and cooled to 0° C. Acetyl chloride (157 mg, 2.0 mmol) was added to the solution slowly. Completion of reaction was monitored by TLC. The reaction mixture was extracted using DCM and water. The organic layer was collected and dried over anhydrous sodium sulfate followed by filtration. The solution was then concentrated and subjected to flash chromatography to afford compound 15. Yield: 196 mg, 74%. $^1$H-NMR (400 MHz, CDCl$_3$): δ (ppm) 7.30 (d, J=4.85 Hz, 2H), 6.86 (d, J=4.85 Hz, 2H), 6.63 (s, 1H), 6.34 (s, 1H), 5.87 (t, J=1.12, 1H), 3.79 (s, 1H), 3.70 (s, 1H). $^{13}$C-NMR (100 MHz, CDCl$_3$): δ (ppm) 169.62, 165.62, 159.78, 139.89, 129.98, 129.32, 125.27, 114.00, 73.00, 55.41, 52.13, 21.30. MS (m/z): [M]$^+$ calcd. for C$_{14}$H$_{16}$O$_5$, 264.1; found, 287.1 for [M+Na]$^+$.

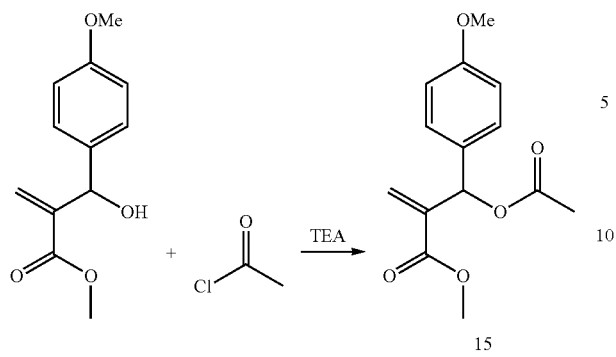

Synthesis of compound 16. Methyl 2-[hydroxy (4-bromophenyl) methyl]acrylate (542 mg, 2.0 mmol) was dissolved in 4 mL of DCM with triethylamine (202.4 mg, 2.0 mmol) and cooled to 0° C. Acetyl chloride (157 mg, 2.0 mmol) was added to the solution slowly. Completion of reaction was monitored by TLC. The reaction mixture was extracted using DCM and water. The organic layer was collected and dried over anhydrous sodium sulfate followed by filtration. The solution was then concentrated and subjected to flash chromatography to afford compound 16. Yield: 197 mg, 63%. $^1$H-NMR (400 MHz, CDCl$_3$): 7.30 (m, 2H), 6.86 (m, 2H), 6.63 (s, 1H), 6.40 (t, J=0.80 Hz, 1H), 5.87 (dd, J=0.80 Hz, J=1.44 Hz, 1H), 3.79 (s, 1H), 3.70 (s, 1H). $^{13}$C-NMR (100 MHz, CDCl$_3$): δ (ppm) 169.45, 165.35, 139.34, 137.08, 131.80, 129.57, 126.06, 122.66, 72.65, 52.22, 21.20. MS (m/z): [M]$^+$ calcd. for C$_{13}$H$_{13}$BrO$_4$, 312.00; found, 335.0 for [M+Na]$^+$.

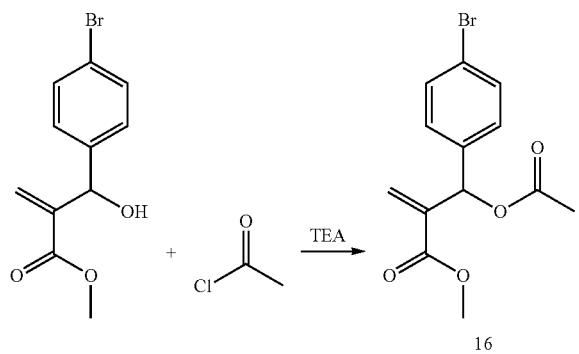

Synthesis of compound 17. Compound 7 (56 mg, 0.2 mmol) was dissolved in 1 mL of MeOH. To the solution, 2-(2-methoxyethoxy) ethanethiol (26 mg, 0.19 mmol) in 0.5 mL water was slowly added. Solvent was removed after reaction. The residue was extracted with DCM for three times. Organic layers were combined and dried over anhydrous sodium sulfate. The solution was dried after filtration and then subjected to flash chromatography afford compound 17. Yield: 40 mg, 90%. $^1$H-NMR (400 MHz, MeOH-d4): δ (ppm) 7.98 (m, 2H), 6.62 (m, 2H), 6.15 (d, J=1.24 Hz, 1H), 5.72 (d, J=1.12 Hz, 1H), 3.76 (s, 3H), 3.63 (t, J=6.58 Hz, 2H), 3.57-3.61 (m, 2H), 3.51-3.56 (m, 2H), 3.44 (d, J=0.88 Hz, 2H), 3.36 (s, 3H), 2.63 (t, J=6.58 Hz 3H). $^{13}$C-NMR (100 MHz, CDCl$_3$): δ (ppm) 166.46, 136.78, 126.32, 71.94, 70.95, 70.28, 59.09, 52.09, 33.06, 30.66. MS (m/z): [M]$^+$ calcd. for C$_{10}$H$_{18}$O$_4$S, 234.09; found, 257.1 for [M+Na]$^+$.

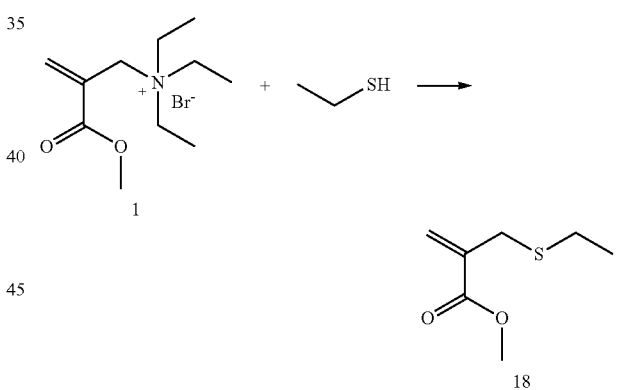

Synthesis of compound 18. Compound 1 (140 mg, 0.5 mmol) was dissolved in 2 mL of water. To the solution, ethanethiol (28.2 mg, 0.45 mmol) was slowly added. Completion of reaction was monitored by TLC. Then the reaction mixture was extracted with DCM for three times. Organic layers were combined and dried over anhydrous sodium sulfate. The solution was dried after filtration and then subjected to flash chromatography afford compound 18. Yield: 72 mg, 50%. $^1$H-NMR (400 MHz, CDCl$_3$): δ (ppm) 6.20 (d, J=1.08 Hz, 1H), 5.65 (q, J=1.08 Hz, 1H), 3.79 (s, 3H), 3.40 (s, 2H), 2.48 (q, J=7.40 Hz, 2H), 1.24 (t, J=7.40 3H). $^{13}$C-NMR (100 MHz, CDCl$_3$): δ (ppm) 166.71, 136.90, 125.80, 52.08, 32.34, 25.41, 14.28.

Synthesis of compound 19. Compound 8e (53.4 mg, 0.3 mmol) and 2-(2-methoxyethoxy) ethanethiol (39.0 mg, 0.29 mmol) was dissolved in 1 mL of DCM. To the solution, triethylamine (30.5 mg, 0.3 mmol) was added. Completion of reaction was monitored by TLC. Then the reaction mixture was extracted using DCM and water for three times. Organic layers were combined Organic layers were combined and dried over anhydrous sodium sulfate. The solution was dried after filtration and then subjected to flash chromatography afford compound 19. Yield: 58 mg, 85%. $^1$H-NMR (400 MHz, D$_2$O): δ(ppm) 5.74 (s, 1H), 5.54 (s, 1H), 3.58-3.72 (m, 6H), 3.48 (s, 2H), 3.39 (s, 3H), 2.82 (s, 3H), 2.71 (t, J=6.37 Hz, 2H)$^{13}$H-NMR (100 MHz, CDCl$_3$): δ (ppm) 167.40, 142.14, 121.63, 70.66, 70.62, 70.59, 70.49, 70.46, 70.38, 70.03, 69.55, 63.70, 50.67, 39.18. MS (m/z): [M]$^+$ calcd. for C$_{10}$H$_{19}$NO$_3$S, 233.11; found, 256.1 for [M+Na]$^+$.

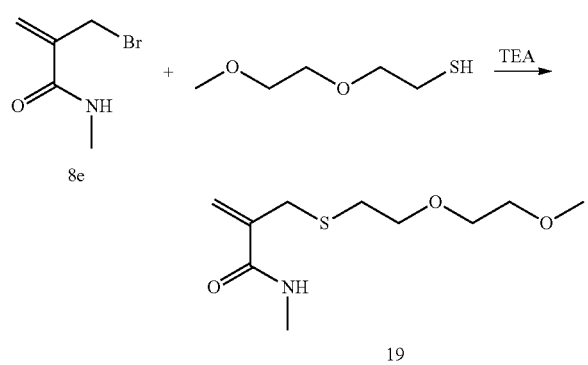

Synthesis of compound 20. Compound 13a (70 mg, 0.21 mmol) and triethylamine (21.2 mg, 0.21 mmol) was mixed in a glass vial and kept for 30 minutes. Then ethanethiol (6.8 mg, 0.11 mmol) in 1 mL of MeOH was added to the vial. Completion of reaction was monitored by TLC. Then the reaction mixture was extracted using DCM and water for three times. Organic layers were combined and dried over anhydrous sodium sulfate. The solution was dried after filtration and then subjected to flash chromatography to afford compound 20. Yield: 30 mg, 87%. $^1$H-NMR (400 MHz, CDCl$_3$): δ (ppm) 7.43 (m, 2H), 7.25 (m, 2H), 6.45 (s, 1H), 6.04 (s, 1H), 5.03 (s, 1H), 3.72 (s, 3H), 2.42 (q, J=7.40 Hz, 2H), 1.21 (t, J=7.40 Hz, 3H). $^{13}$C-NMR (100 MHz, CDCl$_3$): δ (ppm) 166.36, 140.05, 139.15, 131.60, 130.05, 127.22, 121.21, 62.20, 48.19, 26.43, 14.19. MS (m/z): [M]$^+$ calcd. for C$_{13}$H$_{15}$BrO$_2$S, 314.0; found, 336.9 for [M+Na]$^+$.

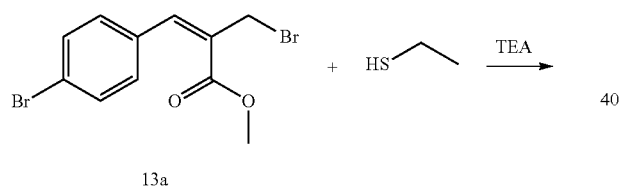

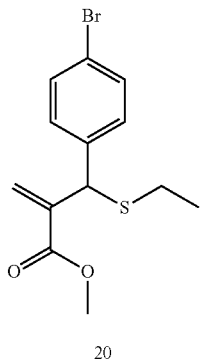

Synthesis of compound 21. MeOH solution (1 mL) of compound 16 (100 mg, 0.32 mmol) was added with 1 mL of saturate NaHCO$_3$ aqueous solution. To the mixture ethanthiol (19.8 mg, 0.32 mmol) was added. The was stirred at room temperature until reaction completed. MeOH was then removed. The residue was extracted using DCM and water for 3 times. Organic layers were combined and dried over anhydrous sodium sulfate. The solution was dried after filtration and then subjected to flash chromatography to afford compound 21. Yield: 85 mg, 84%. The product contains 13% cis and 87% trans isomers. $^1$H-NMR (400 MHz, CDCl$_3$): δ(ppm) trans isomer: 7.65 (s, 1H), 7.54 (m, 2H), 7.39 (m, 2H), 3.85 (s, 3H), 3.61 (s, 2H), 2.58 (q, J=7.40 Hz, 2H), 1.22 (t, J=7.40 Hz, 3H). cis isomer: 7.44 (m, 2H), 7.14 (m, 2H), 6.67 (s, 1H), 3.70 (s, 3H), 3.51 (d, J=1.00 Hz, 2H), 2.54 (q, J=7.40 Hz, 2H), 1.27 (t, J=7.40 Hz, 3H). $^{13}$C-NMR (100 MHz, CDCl$_3$): δ(ppm) trans isomer: 167.85, 139.30, 134.01, 131.99, 131.27, 130.36, 123.38, 52.51, 28.43, 27.21, 14.78. MS (m/z): [M]$^+$ calcd. for C$_{13}$H$_{15}$BrO$_2$S, 314.0; found, 336.9 for [M+Na]$^+$.

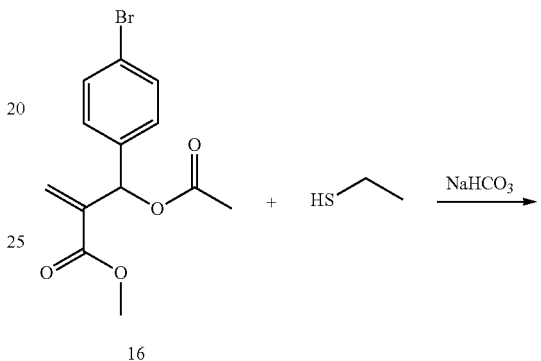

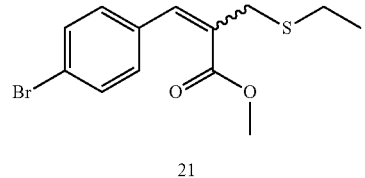

Synthesis of compound 22. MeOH solution (1 mL) of compound 15 (132 mg, 0.50 mmol) was added with 1 mL of saturate NaHCO$_3$ aqueous solution. To the mixture ethanthiol (31 mg, 0.50 mmol) was added. The was stirred at room temperature until reaction completed. MeOH was then removed. The residue was extracted using DCM and water for 3 times. Organic layers were combined and dried over anhydrous sodium sulfate. The solution was dried after filtration and then subjected to flash chromatography to afford compound 22. Yield: 85 mg, 84%. The product contains 7% cis and 93% trans isomers. $^1$H-NMR (400 MHz, CDCl$_3$): δ(ppm) trans isomer: 7.70 (s, 1H), 7.51 (m, 2H), 6.94 (m, 2H), 3.85 (s, 3H), 3.84 (s, 3H), 3.69 (s, 2H), 2.62 (q, J=7.37 Hz, 2H), 1.25 (t, J=7.37 Hz, 3H). cis isomer: 7.25 (m, 2H), 6.85 (m, 2H), 6.67 (s, 1H), 3.81 (s, 3H), 3.72 (s, 3H), 3.52 (d, J=1.01 Hz, 2H), 2.55 (q, J=7.37 Hz, 2H), 1.26 (t, J=7.37 Hz, 3H). $^{13}$C-NMR (100 MHz, CDCl$_3$): δ(ppm) trans isomer: 168.39, 160.39, 140.61, 131.75, 127.66, 127.37, 114.26, 55.47, 52.32, 28.68, 27.15, 14.85. MS (m/z): [M]$^+$ calcd. for C$_{13}$H$_{15}$BrO$_2$S, 266.1; found, 289.1 for [M+Na]$^+$.

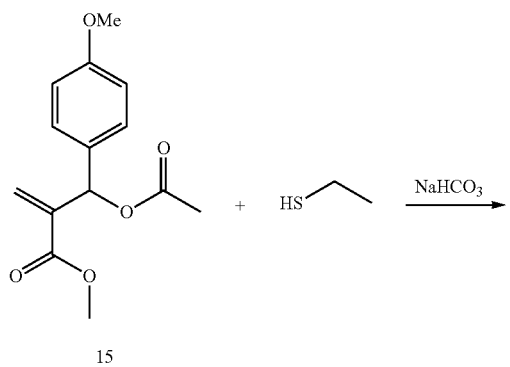

Synthesis of compound 23. Triethylamine (55.7 mg, 0.55 mmol) was added to compound 1b (89 mg, 0.50 mmol) at room temperature. Then, benzylamine (48.2 mg, 0.45 mmol) in 0.5 mL of THF was added to the reaction mixture followed by the addition of 0.5 mL of water. The reaction mixture was extracted with ethyl acetate for 3 times after reaction completed. Organic layers was collected and dried over anhydrous sodium sulfate. Product, compound 23 was obtained after flash chromatography. Yield: 100.6 mg, 84%. $^1$H-NMR (400 MHz, MeOH-d4/D$_2$O(1:1)): δ(ppm): 7.21-7.37 (m, 5H), 6.20 (s, 1H), 5.86 (d, J=1.32 Hz, 1H), 3.71 (s, 6H), 3.55 (s, 2H), 3.25 (s, 4H). $^{13}$C-NMR (100 MHz, CDCl$_3$): δ (ppm) 167.31, 139.08, 137.99, 128.54, 128.37, 128.25, 126.99, 126.11, 58.34, 54.26, 51.73. MS (m/z): [M]$^+$ calcd. for C$_{14}$H$_{18}$BrO$_3$S, 266.1; found, 289.1 for [M+Na]$^+$.

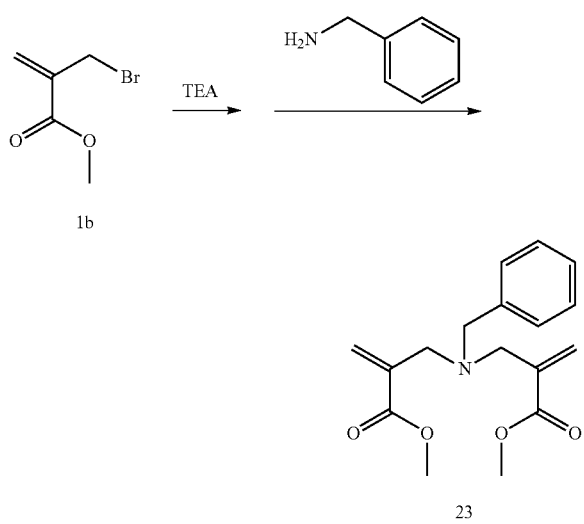

Synthesis of compound 24. Compound 15 (52.8 mg, 0.20 mmol) was dissolved in 400 uL of MeOH and 200 uL mixture. Benzyl amine (10.7 mg, 0.10 mmol) was added to the mixture. The reaction was kept overnight. MeOH was then removed. The residue was extracted using DCM and water for 3 times. Organic layers were combined and dried over anhydrous sodium sulfate. The solution was dried after filtration and then subjected to flash chromatography to afford compound 24. Yield: 27 mg, 52%. The product contains 87% trans isomer. $^1$H-NMR (400 MHz, CDCl$_3$): δ (ppm) 7.78 (s, 2H), 7.56 (m, 4H), 7.19-7.35 (m, 5H), 6.63 (m, 4H), 3.73 (s, 3H), 3.72 (s, 3H), 3.57 (s, 4H), 3.52 (s, 2H). $^{13}$C-NMR (100 MHz, CDCl$_3$): δ(ppm) 169. 69, 160.38, 143.09, 138.99, 132.90, 130.24, 128.01, 127.63, 127.04, 126.79, 113.76, 59.45, 55.18, 52.00, 50.63. MS (m/z): [M]$^+$ calcd. for C$_{31}$H$_{33}$NO$_6$, 515.2; found, 538.2 for [M+Na]$^+$.

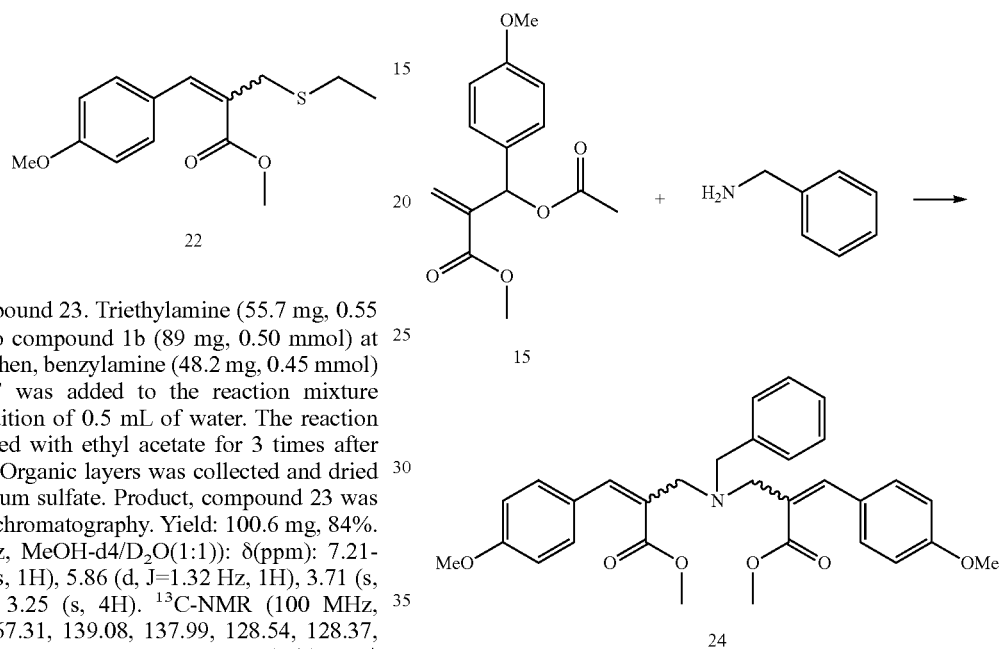

Synthesis of compound 25. MeOH solution (2 mL) of compound 12 (77.2 mg, 0.20 mmol) was added 1 mL of sodium bicarbonate saturated solution followed by the addition of benzyl amine (10.7 mg, 0.10 mmol). The reaction was kept overnight. MeOH was then removed. The residue was extracted using DCM and water for 3 times. Organic layers were combined and dried over anhydrous sodium sulfate. The solution was dried after filtration and then subjected to flash chromatography to afford compound 25. Yield: 23 mg, 73%. $^1$H-NMR (400 MHz, CDCl$_3$): 7.28-7.34 (m, 6H), 7.20-7.26 (m, 1H), 6.85 (m, 2H), 6.34 (d, J=0.96 Hz, 1H), 6.00 (t, J=1.34, 1H), 4.67 (s, 1H), 3.79 (s, 3H), 3.70 (q, J=5.40 Hz, 2H), 3.68 (s, 3H). $^{13}$C-NMR (100 MHz, CDCl$_3$): 167.09, 158.96, 142.34, 140.47, 133.72, 128.93, 128.52, 128.28, 127.09, 125.22, 113.90 61.66, 55.38, 51.90, 51.87. MS (m/z): [M]$^+$ calcd. for C$_{19}$H$_{21}$NO$_3$, 311.15; found, 334.1 for [M+Na]$^+$.

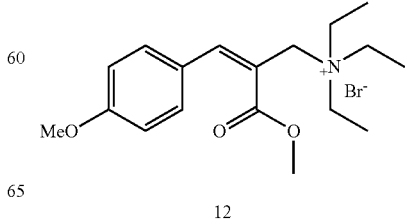

12

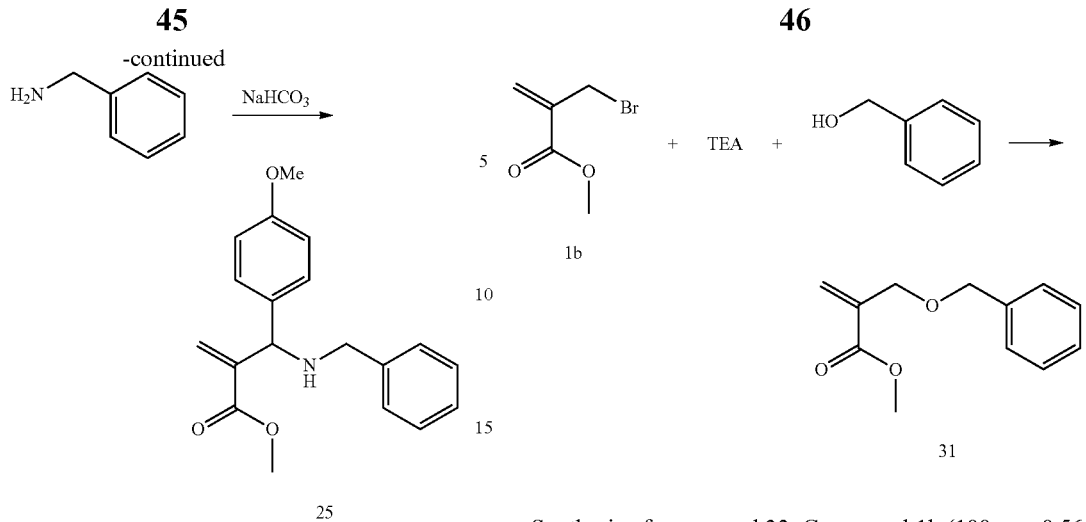

Synthesis of compound 30. Solution of compound 1a (116.1 mg, 1 mmol) in 2 mL of dry DCM was cooled to 0° C. p-Toluenesulfonyl isocyanate (205 mg, 1.05 mmol) was added to the solution. Completion of reaction was monitored by TLC. The residue was subjected to flash chromatography after removing the solvent to afford compound 30. Yield, 285 mg, 91%. $^1$H-NMR (400 MHz, MeOH-d4): δ (ppm) 7.85 (m, 2H), 7.39 (m, 2H), 6.28 (s, 1H), 5.81 (s, 1H), 4.75 (s, 2H), 3.71 (s, 3H), 2.44 (s, 3H). $^{13}$C-NMR (100 MHz, CDCl$_3$): δ (ppm) 165.38, 144.71, 136.50, 135.00, 129.19, 127.67, 127.34, 125.76, 63.62, 51.10, 20.13. MS (m/z): [M]$^+$ calcd. for C$_{13}$H$_{15}$NO$_6$S, 313.06; found, 336.0 for [M+Na]$^+$.

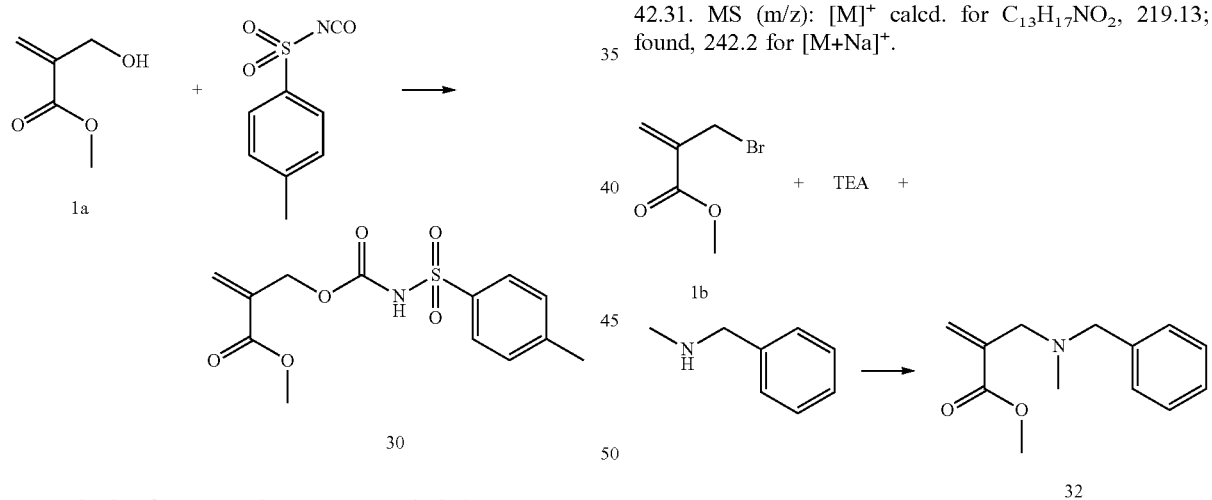

Synthesis of compound 31. Compound 1b (44 mg, 0.25 mmol) was weighed into a glass vial and was added with triethylamine (50 mg, 0.50 mmol). Benzyl alcohol (265 mg, 2.5 mmol) with 100 uL of water was added to the mixture. The reaction was kept for 6 hours. DCM and water were used to extract the reaction mixture. Organic layers were combined and dried over anhydrous sodium sulfate. The solution was dried after filtration and then subjected to flash chromatography to afford compound 31. Yield: 41 mg, 80% $^1$H-NMR (400 MHz, CDCl$_3$): δ (ppm) 7.33-7.38 (m, 4H), 7.30 (m, 1H), 6.33 (q, J=1.30 Hz, 1H), 5.94 (J=1.65 Hz, 1H), 4.59 (s, 2H), 4.24 (t, J=1.37 Hz, 2H), 3.77 (s, 3H). $^{13}$C-NMR (100 MHz, CDCl$_3$): δ (ppm) 166.47, 138.16, 137.25, 128.56, 127.84, 127.79, 126.16, 72.87, 68.45, 51.98. MS (m/z): [M]$^+$ calcd. for C$_{12}$H$_{14}$O$_3$, 206.09; found, 229.2 for [M+Na]$^+$.

Synthesis of compound 32. Compound 1b (100 mg, 0.56 mmol) was weighed into a glass vial and was added with triethylamine (62 mg, 0.62 mmol). N-methyOenzylamine (68 mg, 0.56 mmol) in 100 μL of THF/H$_2$O (1:1) mixed solution was added to the vial. The mixture was extracted using DCM and water for 3 times. Organic layers were combined and dried over anhydrous sodium sulfate. The solution was dried after filtration and then subjected to flash chromatography to afford compound 32. Yield: 91 mg, 74%. $^1$H-NMR (400 MHz, CDCl$_3$): δ (ppm) 7.28-7.35 (m, 4H), 7.20-7.27 (m, 1H), 6.27 (s, 1H), 5.85(q, J=1.56 Hz, 1H), 3.75 (s, 3H), 3.55 (s, 2H), 3.23 (s, 2H), 2.20 (s, 3H). $^{13}$C-NMR (100 MHz, CDCl$_3$): δ (ppm) 167.63, 139.22, 138.06, 128.95, 128.33, 127.10, 126.63, 62.21, 57.71, 51.93, 42.31. MS (m/z): [M]$^+$ calcd. for C$_{13}$H$_{17}$NO$_2$, 219.13; found, 242.2 for [M+Na]$^+$.

Synthesis of Compound 33

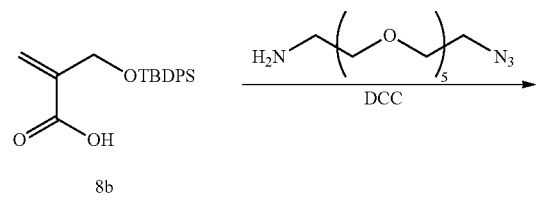

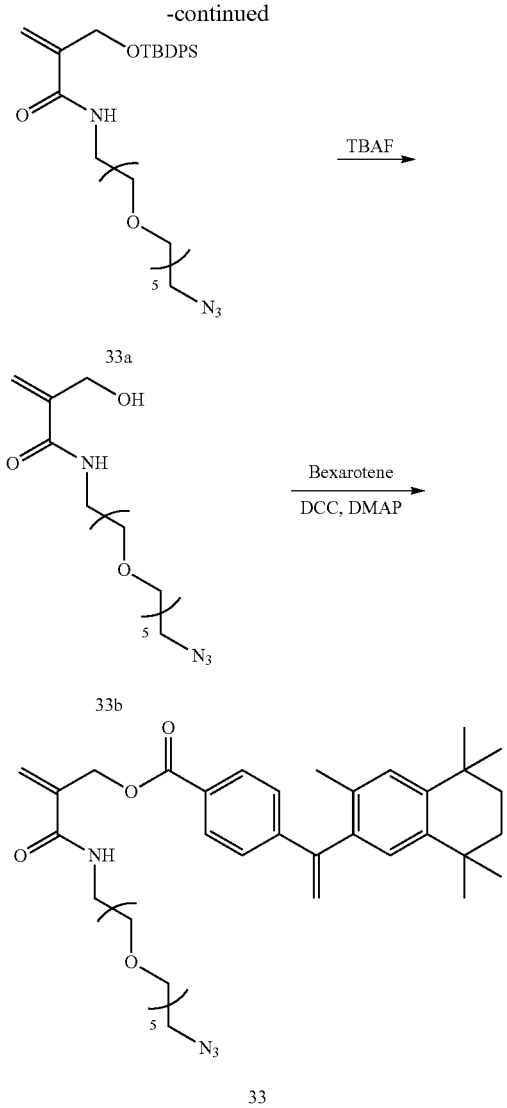

Synthesis of compound 33a. To solution of compound 8b (630 mg, 1.96 mmol) in 10 ml dry DCM, DCC (404 mg, 1.96 mmol) was added. PEG amine (500 mg, 1.63 mmol) was added to the solution after 10 minutes. The reaction was stirred overnight at room temperature. Then the white precipitate was filtered, and the clear solution was subjected to flash chromatography to afford compound 33a. Yield, 635 mg, 62%. $^1$H-NMR (400 MHz, CDCl$_3$): δ (ppm) 7.67 (d, J=7.36 Hz, 4H), 7.35-7.47 (m, 6H), 7.08 (t, NH), 5.93 (s, 1H), 5.46 (s, 1H), 4.42 (s, 2H), 3.57-3.72 (m, 20H), 3.54 (q, J=5.10 Hz, 2H), 3.38 (t, J=5.10 Hz, 2H), 1.07 (s, 9H). $^{13}$C-NMR (100 MHz, CDCl$_3$): 167.05, 142.10, 135.68, 132.99, 130.06, 127.94, 120.80, 70.85, 70.82, 70.77, 70.74, 70.72, 70.71, 70.64, 70.42, 70.18, 69.99, 64.30, 50.82, 39.42, 26.94, 19.34. MS (m/z): [M]$^+$ calcd. for C$_{32}$H$_{48}$N$_4$O$_7$Si, 628.33; found, 651.3 for [M+Na]$^+$.

Synthesis of compound 33b To solution of compound 33a (630 mg, 1.0 mmol) in 2 mL dry THF, 1.15 mL of TBAF solution (1M in THF) was added dropwise at 0° C. The reaction mixture was stirred at room temperature until the reaction completed. Reaction mixture was then dried and subjected to flash chromatography to afford compound 33b. Yield: 296 mg, 76%. $^1$H-NMR (400 MHz, CDCl$_3$): δ (ppm) 7.36 (bs, NH), 5.95 (s, 1H), 5.53(dd, J=0.74 Hz, J=3.67 Hz, 1H), 4.34 (d, J=0.74 Hz, 2H), 3.56-3.73 (m, 20H), 3.53 (s, 2H), 3.38 (t, J=10.04 Hz, 2H), 2.62 (bs, OH). $^{13}$C-NMR (100 MHz, CDCl$_3$): δ (ppm) 167.51, 142.27, 121.76, 70.80, 70.76, 70.73, 70.70, 70.63, 70.60, 70.53, 70.17, 69.68, 63.90, 50.81, 39.31. MS (m/z): [M]$^+$ calcd. for C$_{16}$H$_{30}$N$_4$O$_7$, 390.21; found, 413.10 for [M+Na]$^+$.

Synthesis of compound 33 Bexarotene (34.8 mg, 0.1 mmol) was dissolved in 0.5 mL of DCM. To the solution, DCC (20.6 mg, 0.1 mmol) was added followed by the addition of 1 mL of DCM solution of Compound 33b (39 mg, 0.1 mmol) and DMAP (12.2 mg, 0.1 mmol) after 10 minutes. The reaction as stirred overnight. The mixture was dried and subjected to flash chromatography to afford compound 33. Yield: 31 mg, 43%. $^1$H-NMR (400 MHz, CDCl$_3$): δ (ppm) 7.96 (d, J=8.44 Hz, 2H), 7.34 (d, J=8.44 Hz, 2H), 7.12 (s, 1H), 7.07 (s, 1H), 6.74 (t, NH), 5.98 (s), 5.80 (d, J=1.16 Hz, 1H), 5.69 (s, 1H), 5.33 (d, J=1.16 Hz, 1H), 5.09 (s, 2H), 3.57-3.68 (m, 20H), 3.55(q, J=5.01 Hz, 2H). 3.37 (t, J=5.06 Hz, 2H), 1.93 (s, 3H), 1.70 (s, 4H), 1.30 (s, 6H), 1.27 (s, 6H). $^{13}$C-NMR (100 MHz, CDCl$_3$): δ (ppm) 166.36, 166.02, 149.24, 146.04, 144.55, 142.50, 139.58, 138.07, 132.81, 129.93, 128.71, 128.19, 126.77, 121.83, 117.12, 70.83, 70.80, 70.75, 70.70, 70.68, 70.64, 70.41, 70.17, 69.85, 63.83, 50.81, 39.60, 35.32, 34.14, 34.04, 32.07, 32.02, 20.07. MS (m/z): [M]$^+$ calcd. for C$_{40}$H$_{56}$N$_4$O$_8$, 720.41; found, 743.4 for [M+Na]$^+$.

Synthesis of compound 34 Compound 33b (39 mg, 0.1 mmol) was dissolved in 1 mL of dry THF. To the solution, 135 μL of phosgene (20% in toluene) was added. The reaction was stirred under argon atmosphere for 3 hours. Then, solvent and remaining phosgene was removed by rotovapping (The receiving flask in evaporator was filled with saturated sodium hydroxide solution and the outlet of the pump was connected to saturated sodium hydroxide to quench the phosgene. The operation was carried in a high hazardous fume hood.) The residue was added with THF solution (1 mL) of desmethyl tamoxifen (35.7 mg, 0.1 mmol) followed by the addition of aqueous solution (1 mL) of sodium bicarbonate (25.3 mg, 0.3 mmol). Completion of reaction was followed by TLC. The reaction mixture was extracted using DCM and water for 3 times. Organic layers were combined and dried over anhydrous sodium sulfate. The solution was dried after filtration and then subjected to flash chromatography to afford compound 34. Yield: 24 mg, 33%. $^1$H-NMR (400 MHz, MeOH-d4): δ (ppm) 7.31-7.40 (m, 2H), 7.07-7.30 (m, 8H), 6.78 (d, J=8.68 Hz, 2H), 6.60 (d, J=8.68 Hz, 2H), 6.07 (s, 1H), 5.49 (s, 1H), 4.00 (t, J=5.36 Hz, 2H), 3.33-3.67 (m, 24H), 2.76 (t, J=5.36 Hz, 2H), 2.45(q, J=7.40 Hz, 2H), 2.28 (s, 3H), 0.91(t, J=7.40 Hz, 3H). $^{13}$C-NMR (100 MHz, MeOH-d4): δ (ppm) 168.05, 156.84, 143.69, 142.37, 141.33, 139.05, 138.46, 135.66, 131.58, 129.49, 129.03, 127.83, 127.58, 126.32, 125.81, 124.28, 113.19, 70.24, 70.21, 70.20, 70.18, 70.16, 69.94, 69.74, 69.02, 65.34, 60.40, 55.31, 50.37, 40.66, 38.72, 28.45, 12.43. MS (m/z): [M]$^+$ calcd. for C$_{41}$H$_{54}$N$_4$O$_8$, 730.39; found, 753.2 for [M+Na]$^+$.

Synthesis of Compound 36

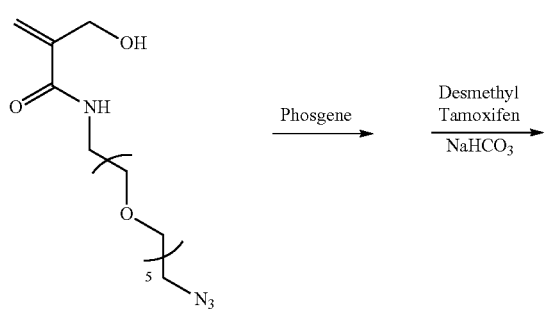

33b

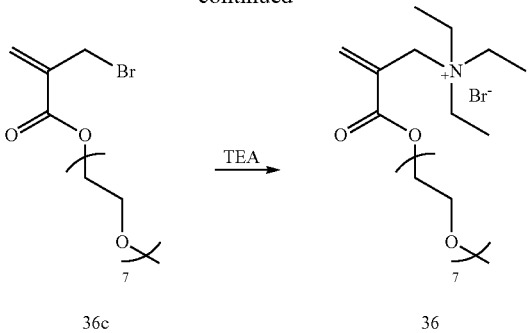

36c → 36

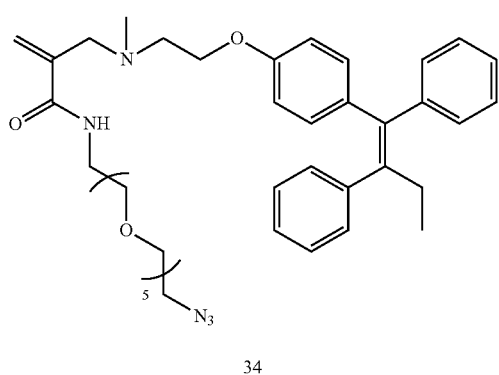

34

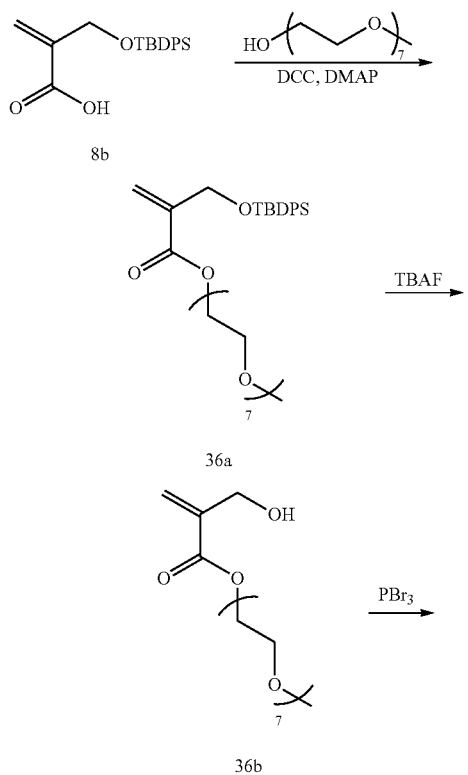

8b → 36a → 36b

Synthesis of compound 36a. Solution of compound 8b (400 mg, 1.24 mmol) in 2 mL DCM was added with DCC (256 mg, 1.24 mmol). After 10 minutes, the reaction mixture was added with PEG alcohol (352 mg, 1.0 mmol) and DMAP (152 mg, 1.24 mmol). The reaction was stirred overnight at room temperature. The solution was collected after removal of white precipitate using filtration. Then, the solution was dried and subjected to then subjected to flash chromatography to afford compound 36a. Yield: 298 mg, 45%. $^1$H-NMR (400 MHz, CDCl$_3$): δ (ppm) 7.63-7.71 (d, J=6.40 Hz, 4H), 7.33-7.47 (m, 6H), 6.35(q, J=1.92 Hz, 1H), 6.12(q, J=1.92 Hz, 1H), 4.42 (t, J=1.90 Hz, 2H), 4.26 (t, J=4.96 Hz, 2H), 3.69 (t, J=4.76 Hz, 2H), 3.58-3.67 (m, 22H), 3.54 (m, 2H), 3.38 (s, 3H), 1.08 (s, 9H). $^{13}$C-NMR (100 MHz, CDCl$_3$): δ (ppm) 165.81, 139.38, 135.58, 133.36, 129.92, 127.90, 124.42, 72.08, 70.76, 70.72, 70.67, 69.16, 63.86, 62.32, 59.18, 26.95, 19.43. MS (m/z): [M]$^+$ calcd. for C$_{35}$H$_{54}$O$_{10}$Si, 662.35; found, 685.3 for [M+Na]$^+$.

Synthesis of compound 36b. Solution of compound 36a (200 mg, 0.31 mmol) in 1 mL of dry THF was added with 340 µL of TBAF solution (1 M in THF) at 0° C. After reaction completion, the solution was dried and subjected to flash chromatography to afford compound 36b. Yield: 125 mg, 94%. $^1$H-NMR (400 MHz, CDCl$_3$): δ (ppm) 6.29 (s, 1H), 5.84 (q, J=1.32 Hz, 1H), 4.30-4.38 (m, 4H), 3.75 (m, 2H), 3.61-3.70 (m, 22H), 3.55 (m, 2H), 3.38 (s, 3H), 2.64 (bs, OH). $^{13}$C-NMR (100 MHz, CDCl$_3$): δ (ppm) 166.34, 139.69, 126.28, 72.08, 70.82, 70.78, 70.72, 70.66, 69.07, 64.01, 62.56, 59.18. MS (m/z): [M]$^+$ calcd. for C$_{19}$H$_{36}$O$_{10}$, 424.23; found, 447.1 for [M+Na]$^+$.

Synthesis of compound 36c. Compound 36b (120 mg, 0.28 mmol) was dissolved in 1 mL of dry DCM and cooled to 0° C. PBr$_3$ (38 mg, 0.14 mmol) was slowly added to the solution. The reaction completed in 30 minutes. The reaction was quenched by adding saturated sodium bicarbonate solution. The reaction mixture was further extracted using DCM and water for 3 times. Organic layers were combined and dried over anhydrous sodium sulfate. The solution was dried after filtration to afford compound 36c which was directly used for next reaction.

Synthesis of compound 36. Compound 36c (24 mg, 0.2 mmol) was weighed to a glass vial. To the vial triethylamine (81 mg, 0.8 mmol) was added. After 4 hours, 3 mL of diethyl ether was added and sonicated for 1 minutes. Then, supernatant was removed. The operation was repeated for 4 times and the viscous solid was collected and dried to afford compound 36. Yield: 94 mg, 68%. $^1$H-NMR (400 MHz, MeOH-d4): δ (ppm) 6.93 (s, 1H), 6.40 (s, 1H), 4.40 (m, 2H), 4.24 (s, 2H), 3.79 (m, 2H), 3.60-3.69 (m, 22H), 3.54 (m, 2H), 3.36 (s, 3H), 3.28-3.35 (q, 6H), 1.37 (t, J=7.19 Hz, 9H). $^{13}$C-NMR (100 MHz, MeOH-d4): δ(ppm) 166.86, 140.63, 130.82, 72.98, 71.57, 71.55, 71.36, 69.85, 66.18, 59.09, 57.01, 54.35, 8.12. MS (m/z): [M]+ calcd. for $C_{25}H_{50}BrNO_9$, 587.27; found, 508.3 for [M−Br]+.

Synthesis of Compound 37

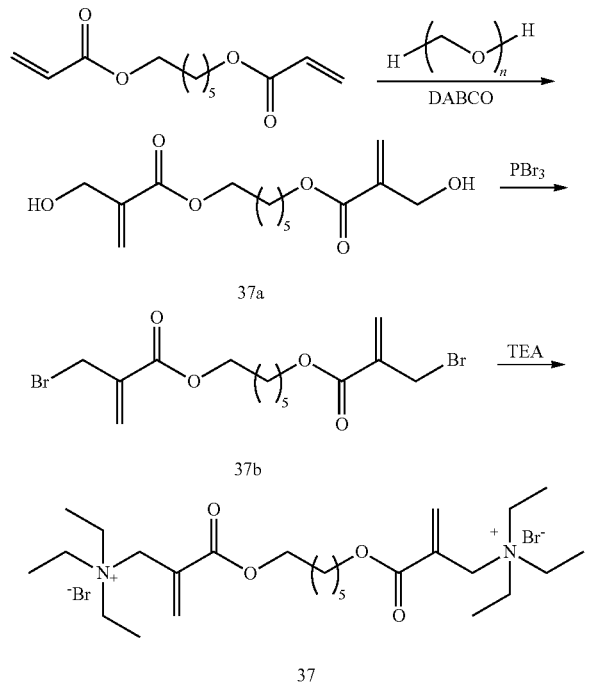

Synthesis of compound 37a DABCO (4.9 g, 44 mmol) were dispersed in 10 mL water followed by the addition of paraformaldehyde (1.98 g, 52 mmol) at 0° C. Acetonitrile (17.5 mL) and 1,6-hexanediol diacrylate (5 g, 22 mmol) was sequentially added to the reaction after 15 minutes. Then the reaction mixture was heated at 45° C. for 3 hours. The reaction mixture was then cooled and volatiles were removed. The crude was extracted using ethyl acetate and water for 3 times. Organic layers were combined and dried over anhydrous sodium sulfate. The solution was dried after filtration and then subjected to flash chromatography to afford compound 37a. Yield: 3.2 g, 51%. 1H-NMR (400 MHz, CDCl3): δ (ppm) 6.23 (s, 2H), 5.82 (s, 2H), 4.31 (s, 4H), 4.17 (t, 4H), 2.51(bs, 2H), 1.69 (m, 4H), 1.42 (m, 4H). 13C-NMR (100 MHz, CDCl3): 166.38, 139.49, 125.72, 64.75, 62.62, 28.44, 25.61. MS (m/z): [M]+ calcd. for $C_{14}H_{22}O_6$, 286.14; found, 309.1 for [M+Na]+.

Synthesis of compound 37b To solution of compound 37a (500 mg, 1.75 mmol) in 10 mL drug DCM, PBr3 (473 mg, 165 μL) was added at 0° C. The reaction was stirred at room temperature and completed in 30 minutes. The reaction was quenched by addition of 2 mL of saturated sodium bicarbonate solution. The crude was extracted using ethyl acetate and water for 3 times. Organic layers were combined and dried over anhydrous sodium sulfate. The solution was dried after filtration and further subjected chromatography to afford compound 36c. Yield: 360 mg, 50%. 1H-NMR (400 MHz, CDCl3): δ (ppm) 6.33 (s, 2H), 5.94 (s, 2H), 4.22 (t, J=6.57 Hz, 4H), 4.18 (s, 4H), 1.73 (m, 4H), 1.46 (m, 4H). 13C-NMR (100 MHz, CDCl3): δ (ppm) 164.90, 137.55, 129.05, 65.20, 28.46, 28.4639, 25.6. MS (m/z): [M]+ calcd. for $C_{14}H_{20}Br_2O_4$, 409.97; found, 433.0 for [M+Na]+.

Synthesis of compound 37 Compound 37b (100 mg, 0.244 mmol) was dissolved in 3 mL of dry DCM. Then triethylamine (247 mg, 345 μL) was added to the solution. The reaction was stirred for 24 hours. Then volatiles were removed, and the residue was added with 5 mL of diethyl ether to precipitate the product. Then the precipitate was re-dissolved in 100 μL of MeOH and precipitated in 5 mL of diethyl ether. The procedure was repeated for two more times. The precipitate was collected and dried to afford compound 37. Yield: 98 mg, 64%. 1H-NMR (400 MHz, MeOH-d4): δ (ppm) 6.89 (s, 2H), 6.40 (s, 2H), 4.27 (t, J=6.72 Hz, 4H), 4.23 (s, 4H), 3.25-3.36 (q, 12H), 1.76 (m, 4H), 1.48 (m, 4H), 1.31-1.42 (t, J=7.12 Hz, 18H). 13C-NMR (100 MHz, MeOH-d4): δ (ppm) 165.94, 138.90, 129.46, 65.73, 53.01, 28.13, 28.10, 25.25, 7.98.

Synthesis of compound 38 Compound 38 was synthesized following the reported procedures. (Fan, et al. 2013 *Biomacromolecules* 148, 2814-2821.)

Kinetics Study

10 μmol (2 eq.) of A1 molecules was dissolved in single or mixed deuterated solvents (the volume of solvent depends on the solubility of A1). Then, 5 μmol (1 eq.) of 2-(2-Methoxyethoxy) ethanethiol or benzylamine was added to the solution. The reaction was immediately followed by NMR. The final concentration of A1 for each molecule is shown at the end of supplementary information case by case. The conversion of thiol or amine was calculated from the integration of corresponding peaks by NMR and plotted against reaction time.

Thiol-Click Condition:

Compound 1, 2, 3, 4, 5, 8, 11, 12, 13: 10 μmol (2 eq.) of molecule 1, 2, 3, 4, 5, 8, 11, 12, 13 was dissolved in 1000 μL of MeOH-d4. Then, 5 μmol (1 eq.) of thiol was added to the solution. The reaction was immediately followed by NMR.

Compound 6, 7, 9: 10 μmol (2 eq.) of molecule 6, 7, 9 was dissolved in 500 μL of MeOH-d4 and 500 μL of 50 mM pH 7.4 phosphate buffer. Then, 5 μmol (1 eq.) of thiol or amine was added to the solution. The reaction was immediately followed by NMR.

Compound 10: 10 μmol (2 eq.) of molecule 10 was dissolved in 1000 μL of DMSO-d6 and 500 μL of 50 mM pH 7.4 phosphate buffer. Then, 5 μmol (1 eq.) of thiol or amine was added to the solution. The reaction was immediately followed by NMR.

Compound 14, 15, 16: 10 μmol (2 eq.) of molecule 14, 15, 16 was dissolved in dissolved in 500 μL of MeOH-d4 and 500 μL of 50 mM pH 6.2 phosphate buffer. Then, 5 μmol (1 eq.) of thiol or amine was added to the solution. The reaction was immediately followed by NMR.

Amine-Click Condition:

Compound 1, 2, 3, 4, 5, 6, 7, 8, 9, 11, 12, 13: 10 μmol (2 eq.) of molecule 1, 2, 3, 4, 5, 6, 7, 8, 9, 11, 12, 13 was dissolved in 500 μL of MeOH-d4 and 500 μL of 50 mM pH 7.4 phosphate buffer. Then, 5 μmol (1 eq.) of benzylamine was added to the solution. The reaction was immediately followed by NMR.

Compound 10: 10 μmol (2 eq.) of molecule 10 was dissolved in 1000 μL of DMSO-d6 and 500 μL of 50 mM pH 7.4 phosphate buffer. Then, 5 μmol (1 eq.) of benzylamine was added to the solution. The reaction was immediately followed by NMR.

Compound 14, 15, 16: 10 μmol (2 eq.) of molecule 14, 15, 16 was dissolved in 800 μL of MeOH-d4 and 200 μL of 50 mM pH 7.4 phosphate buffer. Then, 5 μmol (1 eq.) of benzylamine was added to the solution. The reaction was immediately followed by NMR.

Declick Reaction

Typically, product of thiol-A1 or amine-A1 click product was dissolved in single or mixed deuterated solvents (the volume of solvent depends on the solubility of A1 The volume of solvent depends on the solubility of click product). Then, thiol was added to the solution. The reaction was immediately followed by NMR.

Compound 17: 10 µmol (1 eq.) of 17 was dissolved in 500 µL of MeOH-d4 and 500 µL of 50 mM pH6.8 phosphate buffer. Then, 80 µmol (8 eq.) of thiol was added to the solution. Final concentration of 17 is 10 mM.

Compound 18: 10 µmol (1 eq.) of 18 was dissolved in 500 µL of MeOH-d4 and 500 µL of 50 mM pH7.4 phosphate buffer. Then, 80 µmol (8 eq.) of thiol was added to the solution. Final concentration of 18 is 10 mM.

Compound 19: 10 µmol (1 eq.) of 19 was dissolved in 500 µL of MeOH-d4 and 500 µL of 50 mM pH7.4 phosphate buffer. Then, 10 µmol (0.5 eq.) of thiol was added to the solution. Final concentration of 19 is 10 mM.

Compound 20: 10 µmol (1 eq.) of 20 was dissolved in 1000 µL of MeOH-d4 and 500 µL of 50 mM pH7.4 phosphate buffer. Then, 10 µmol (0.5 eq.) of thiol was added to the solution. Final concentration of 20 is 6.67 mM.

Compound 21: 10 µmol (1 eq.) of 21 was dissolved in 500 µL of MeOH-d4 and 500 µL of 50 mM pH7.4 phosphate buffer. Then, 10 µmol (0.5 eq.) of thiol was added to the solution. Final concentration of 21 is 10 mM.

Compound 22: 10 µmol (1 eq.) of 22 was dissolved in 500 µL of MeOH-d4 and 500 µL of 50 mM pH7.4 phosphate buffer. Then, 10 µmol (0.5 eq.) of thiol was added to the solution. Final concentration of 22 is 10 mM.

Compound 23: 10 µmol (1 eq.) of 23 was dissolved in 1000 µL of MeOH-d4 and 500 µL of 50 mM pH7.4 phosphate buffer. Then, 10 µmol (1 eq.) of thiol was added to the solution. Final concentration of 23 is 6.67 mM.

Compound 24: 10 µmol (1 eq.) of 24 was dissolved in 2000 µL of MeOH-d4 Then, 5 µmol (0.5 eq.) of thiol or amine was added to the solution. Final concentration of 24 is 5 mM.

Compound 25: 10 µmol (1 eq.) of 25 was dissolved in 1000 µL of MeOH-d4 and 500 µL of 50 mM pH7.4 phosphate buffer. Then, 5 µmol (0.5 eq.) of thiol was added to the solution. Final concentration of 25 is 6.67 mM.

Thiol Triggered Functionality Recovery

Functionality Recovery from Small Molecules: 1, 4, 6, 7, 17, 30, 31, 32

Triethylamine recovery: 10 µmol (1 eq.) of 1 was dissolved in 1000 µL of MeOH-d4. Then, 10 µmol (10 eq.) of thiol was added to the solution. The release of triethylamine was followed by NMR.

Pyridine recovery: 10 µmol (1 eq.) of 4 was dissolved in 500 µL of MeOH-d4 and 500 µL of 50 mM pH7.4 phosphate buffer. Then, 10 µmol (1 eq.) of thiol was added to the solution. The release of pyridine was followed by NMR.

Acetic acid recovery: 10 µmol (1 eq.) of 6 was dissolved in 500 µL of MeOH-d4 and 500 µL of 50 mM pH7.4 phosphate buffer. Then, 10 µmol (1 eq.) of thiol was added to the solution. The release of acetic acid was followed by NMR.

4-nitroaniline recovery: 10 µmol (1 eq.) of 7 was dissolved in 500 µL of MeOH-d4 and 500 µL of 50 mM pH7.4 phosphate buffer. Then, 10 µmol (1 eq.) of thiol was added to the solution. The release of 4-nitroaniline was followed by NMR.

2-(2-Methoxyethoxy) ethanethiol recovery: 10 µmol (1 eq.) of 17 was dissolved in 500 µL of MeOH-d4 and 500 µL of 50 mM pH6.8 phosphate buffer. Then, 10 µmol (8 eq.) of thiol was added to the solution. The release of 2-(2-Methoxyethoxy) ethanethiol was followed by NMR.

Sulfonamide recovery: 10 µmol (1 eq.) of 30 was dissolved in 500 µL of MeOH-d4 and 500 µL of 50 mM pH7.4 phosphate buffer. Then, 10 µmol (1 eq.) of thiol was added to the solution. The release of sulfonamide was followed by NMR.

Benzyl alcohol recovery: 10 µmol (1 eq.) of 31 was dissolved in 500 µL of MeOH-d4 and 500 µL of 50 mM pH7.4 phosphate buffer. Then, 10 µmol (1 eq.) of thiol was added to the solution. The release of benzyl alcohol was followed by NMR.

N-methyOenzylamine recovery: 10 µmol (1 eq.) of 32 was dissolved in 500 µL of MeOH-d4 and 500 µL of 50 mM pH7.4 phosphate buffer. Then, 10 µmol (1 eq.) of thiol was added to the solution. The release of N-methyOenzylamine was followed by NMR.

Functionality Recovery from Small Molecules: 33 & 34:

Compound 33:

Procedure A: 5 µmol (1 eq.) of 33 was dissolved in 500 µL of MeOH-d4 followed by addition of 10 mg of $Na_2CO_3$. 10 µmol (2 eq.) of 2-(2-Methoxyethoxy) ethanethiol was added to solution. The release of Bexarotene was followed by NMR.

Procedure B: To 250 µL of stock solution of compound 33 (1 mM solution in MeOH), 250 µL of 10 mM Glutathione (GSH) solution in 50 mM pH7.4 sodium phosphate buffer was added. The reaction solution was subjected to mass spectral analyses after 6 hours.

Compound 34: 5 µmol (1 eq.) of 34 was dissolved in 500 µL of MeOH-d4 and 500 µL of 50 mM pH7.4 phosphate buffer. 10 µmol (2 eq.) of 2-(2-Methoxyethoxy) ethanethiol was added to solution. The release of Desmethyltamoxifen was followed by NMR.

Aptamer Drug Conjugation and Thiol Triggered of Desmethyltamoxifen

Stock solution of 34 was first prepared in DMSO. 100 µM DNA aptamer (AS1411: 5'-GGT GGT GGT GGT TGT GGT GGT GGT GGT/3DBCO/-3' (SEQ ID NO: 2), ordered from Integrated DNA Technologies) solution was incubated with 20 equivalents of 34 in a solvent mixture of $H_2O$ and DMSO (V/V=80:20) for 1 h at room temperature. After reaction, the aptamer was purified using GE PD SpinTrap G-25 column (GE Healthcare Bio-Sciences, Pittsburgh, PA) to remove the excess of 34. The collected aptamer was characterized by ESI-MS before further experiments. Drug release was performed by incubating 50 µM conjugated aptamer with 10 mM of 2-(2-Methoxyethoxy) ethanethiol at room temperature for 12 h. After reaction, the mixture was injected in a LC-MS system to separate and detect the released drug molecules.

To separate and detect the released small-molecule drug from the Aptamer solution, a Thermo Scientific Ultimate 3000 HPLC system (Thermo Scientific, Tewksbury, MA) with a Thermo Acclaim PepMap RSLC C18 reverse phase column (300 µM×15 cm, 2 µm particle size) was used. The small-molecule drug was eluted using an acetonitrile gradient that increases from 5 to 95% over 50 min at a flow rate of 4 µL/min.

Mass spectral analyses of intact DNA aptamers were performed on a Bruker AmaZon (Billerica, MA) quadrupole ion trap mass spectrometer equipped with an electrospray ionization source. Negative mode was used for detection, the capillary voltage was kept at 3.5 kV, and the capillary temperature was set to 300° C. The intact aptamer was prepared in a $H_2O$/ACN (V/V=1:1) buffer containing 25 mM triethylamine and 25 mM imidazole. The solutions were kept at 90° C. for 10 min to denature the DNA aptamers before MS detection.

LC-MS detection of the released small-molecule drug from the aptamer drug conjugates was acquired on a Bruker AmaZon (Billerica, MA) quadrupole ion trap mass spectrometer equipped with an electrospray ionization source. The electrospray needle voltage was kept at 4 kV, and the capillary temperature was set to 250° C.

PEG Drug Conjugation and Thiol Triggered Release of Bexarotene

Methoxyethoxy) ethanethiol was added to solution. The release of Bexarotene was followed by NMR.

Protein Modification and Analysis
Protein Modification Procedures:

For βLGb labeling reaction, βLGb was first denatured by 8 M of urea to expose the free cysteine. The denatured protein was then diluted with 50 mM pH 8.0 phosphate buffer, which results in a protein solution concentration of 100 μM. This protein solution was incubated with 20 equivalents of 1 for 5 min or with 20 equivalents of 8 for 40 min at room temperature to obtain the fully modified proteins

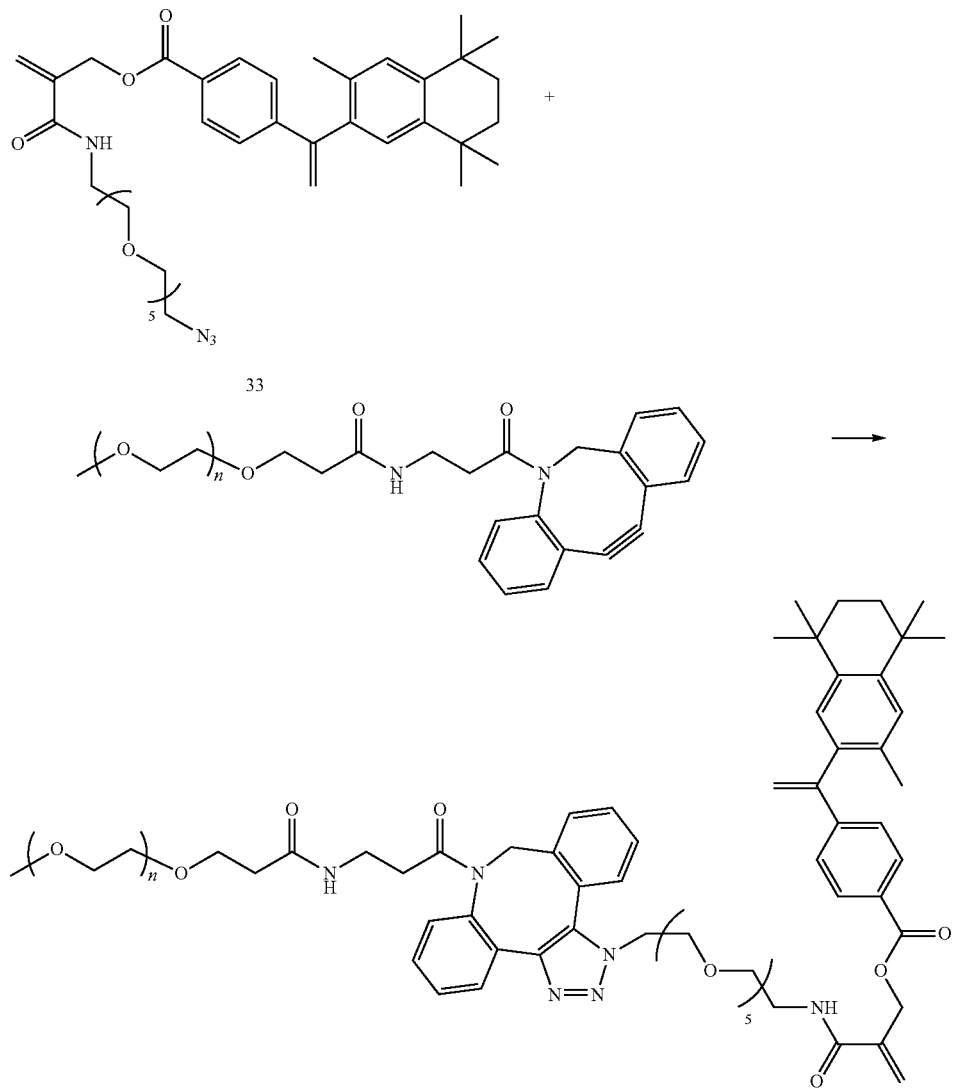

Conjugation: mPEG(5000)-DBCO (50 mg, 0.01 mmol) was dissolved in 1 mL DCM. To the solution, compound 33 (15 mg, 0.02 mmol) in 500 μL of DCM was added. The reaction was stirred at room temperature for 2 hours. The reaction mixture was then concentrated and precipitated in diethyl ether for 4 times. The precipitate was collected and dried to afford compound 35. Yield: 51 mg, 89%. The successful conjugation was monitored by NMR.

Bexarotene release: PEG-33 conjugate (5.74 mg, 1 μmol) was dissolved in 500 μL of MeOH-d4 and 500 μL of 50 mM pH7.4 phosphate buffer. Then 4 μmol (2 eq.) of 2-(2- respectively. After labeling, the reaction mixtures were injected immediately into an HPLC to remove excess labeling reagents and phosphate salts and then later analyzed by ESI-MS.

For BCA labeling reaction, BCA was dissolved in 50 mM pH 8.0 phosphate buffer to acquire a 100 μM protein solution. This protein solution was incubated with 20 equivalents of 36 for 1 h at room temperature to obtain the modified proteins (>95% of the protein was modified). After labeling, the reaction mixtures were injected immediately into LC-MS for intact protein analyses.

For Myoglobin (Myo) reversible modification reactions, the modified protein solution was prepared by reacting 100 µM of the Myo with 20 equivalents of 1 for 5 min in 50 mM pH 8.0 phosphate buffer at room temperature. The proteins were collected from HPLC purification from previous modification reactions, and the excess labeling reagents were removed from the reaction mixtures. The collected protein solution was characterized by ESI-MS or other biophysical characterizations such as Circular Dichroism (CD) and Ultraviolet-Visible Spectroscopy (UV-Vis). The same protein solution was also buffer-exchanged using 10K NMWL Amicon Ultra centrifugal filters (Millipore, Burlington, MA) with 50 mM pH 7.4 phosphate buffer to yield a 100 µM solution for further reverse reaction. The proteins from previous step were incubated with 10 equivalents of 2-(2-Methoxyethoxy) ethanethiol for 2.5 h at room temperature. After reverse modification reaction, the reaction mixture was injected to a LC-MS system for intact protein analyses.

Figure 20:
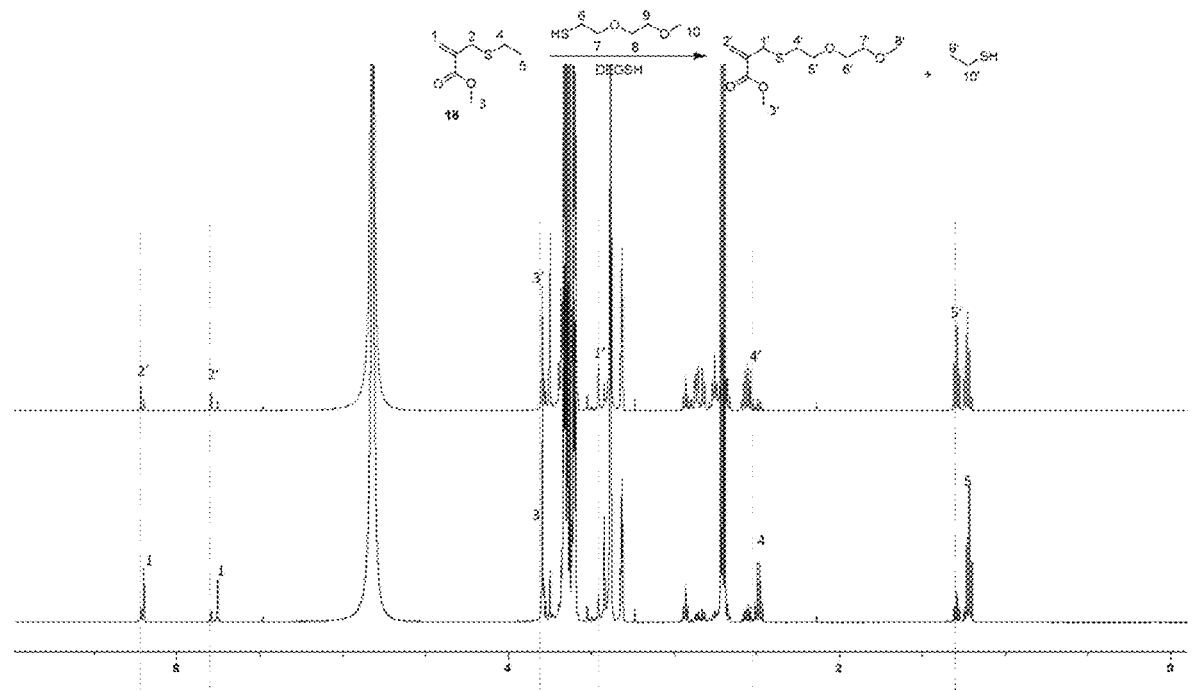
FIG. 20. Declick of thiol click product, 18 is triggerable by thiol suggested by NMR The reaction was carried out at MeOH-d4 and 50 mM pH 7.4 phosphate buffer (1:1). [18]/[DEGSH]=1:8. [18]: 10 mM.
Figure 21:
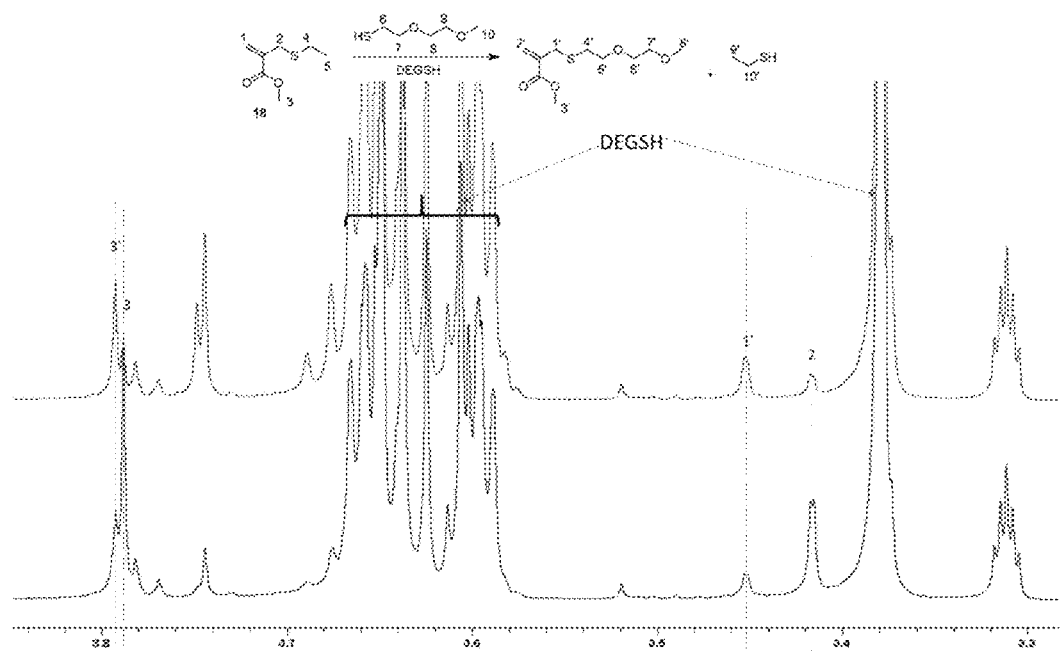
FIG. 21. Declick of thiol click product, 18 is triggerable by thiol suggested by NMR. Zoom-in spectra of FIG. 20.
Figure 22:
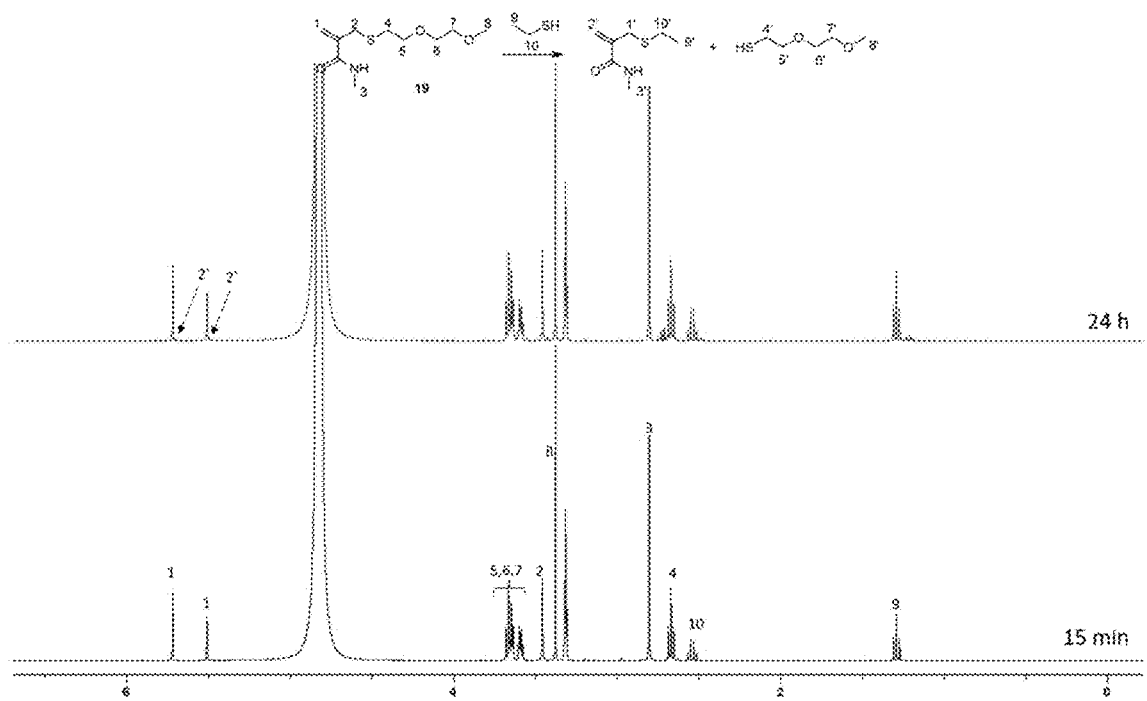
FIG. 22. Declick of thiol click product, 19 is triggerable by thiol suggested by NMR. The reaction was carried out at MeOH-d4 and 50 mM pH 7.4 phosphate buffer (1:1). [19]/[ethanethiol]=2. [19]: 10 mM.
Figure 23:
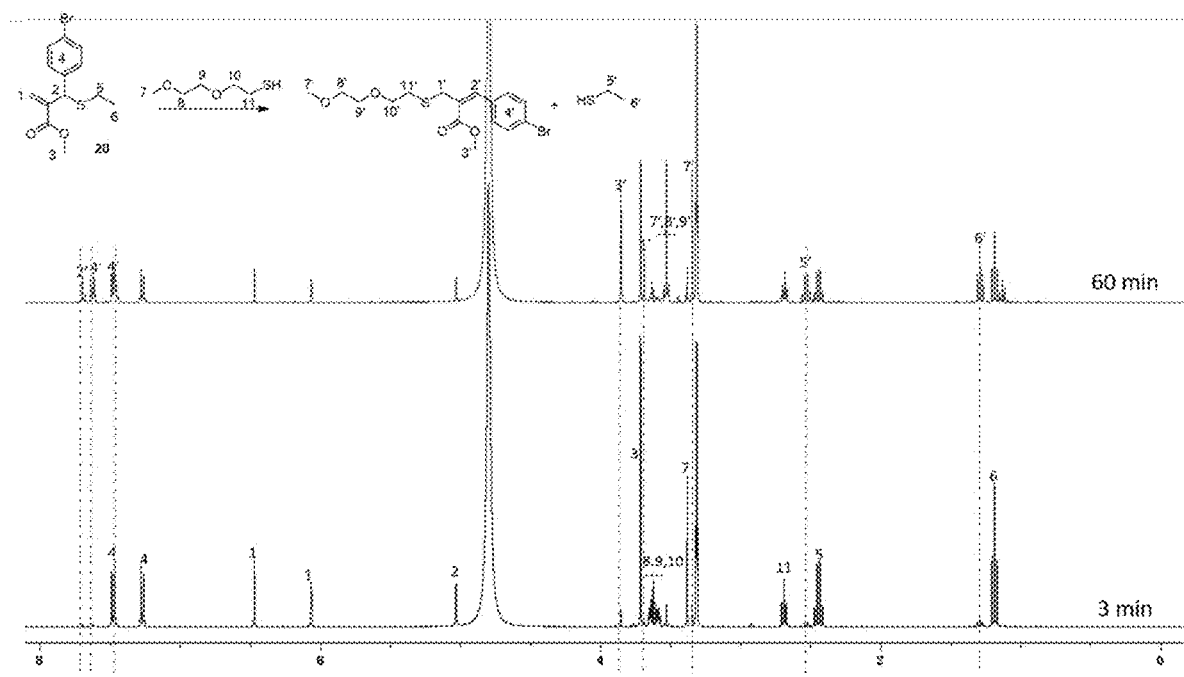
FIG. 23. Declick of thiol click product, 20 is triggerable by thiol suggested by NMR. The reaction was carried out at MeOH-d4 and 50 mM pH 7.4 phosphate buffer (2:1). [20]/[DEGSH]=2. [20]:6.67 mM.
Figure 24:
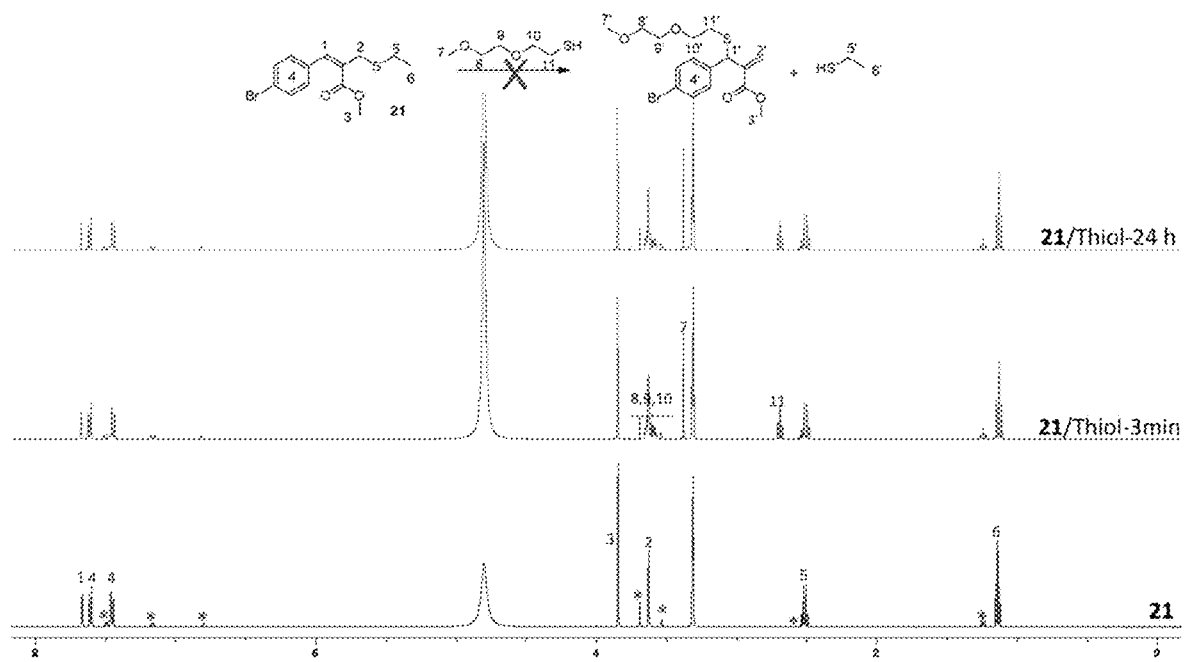
FIG. 24. Thiol click product, 21 is irreversible in the presence of thiol suggested by NMR. The reaction was carried out at MeOH-d4 and 50 mM pH 7.4 phosphate buffer (2:1). [21]/[DEGSH]=2. [21]:10 mM.
Figure 25:
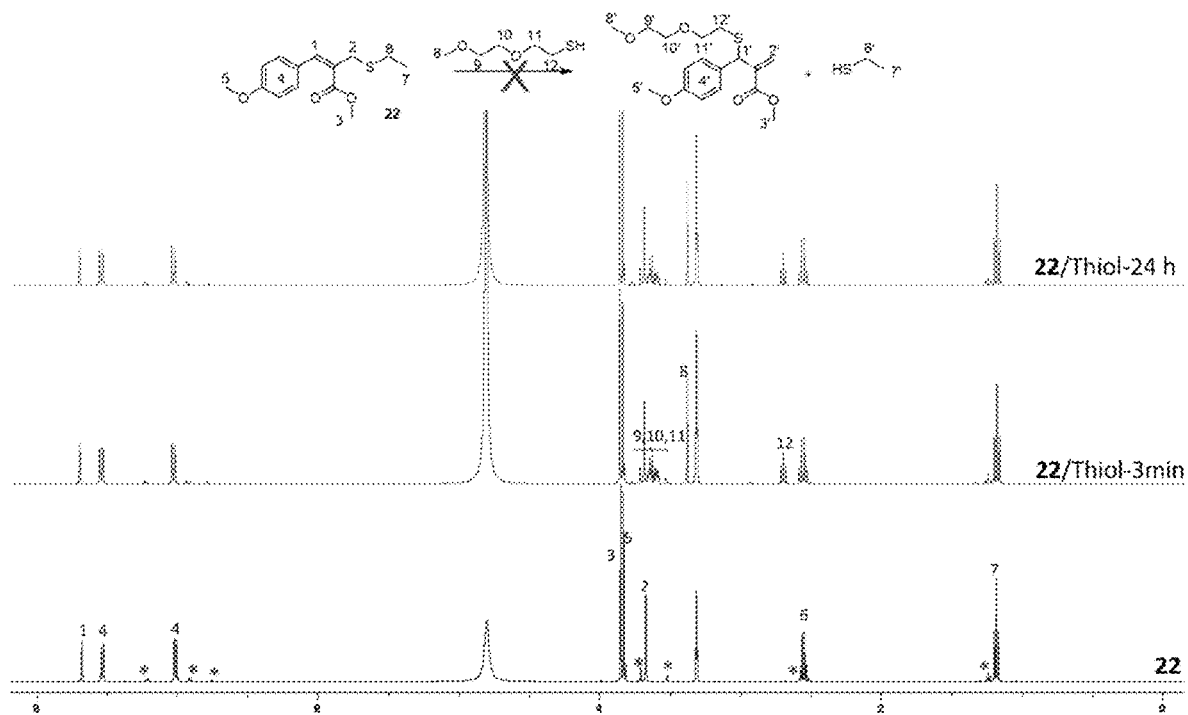
FIG. 25. Thiol click product, 22 is irreversible in the presence of thiol suggested by NMR. The reaction was carried out at MeOH-d4 and 50 mM pH 7.4 phosphate buffer (2:1). [22]/[DEGSH]=2. [22]: 6.67 mM.
Figure 26:
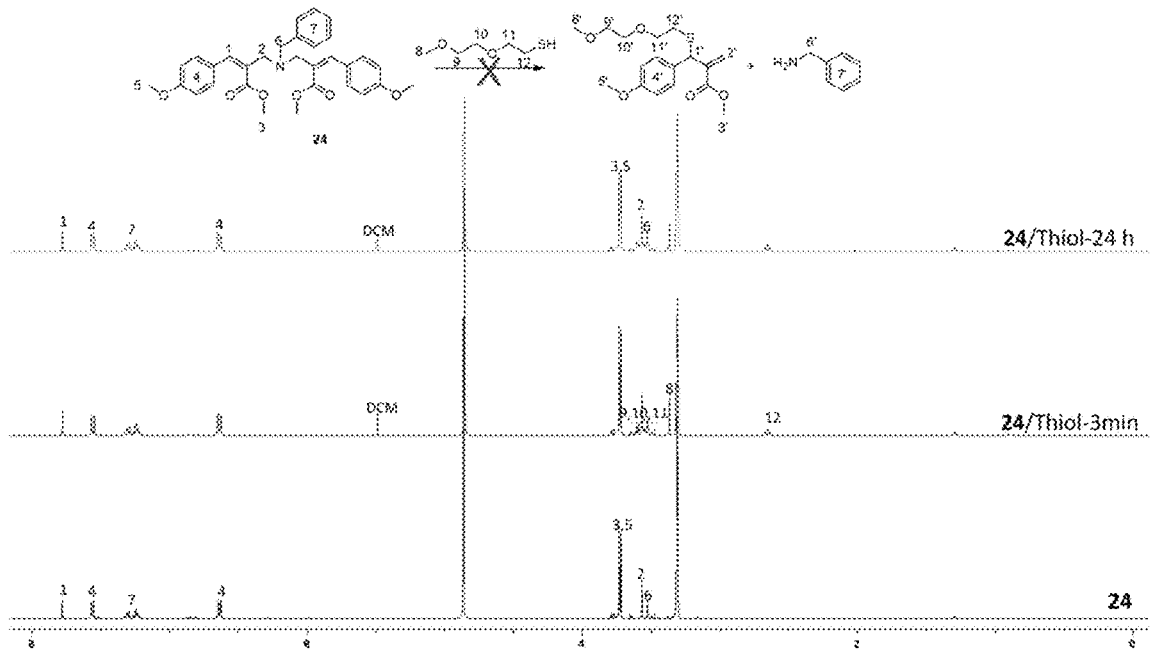
FIG. 26. Amine click product, 24 is irreversible in the presence of thiol suggested by NMR. The reaction was carried out at MeOH-d4. [22]/[DEGSH]=2. [22]: 5 mM.
Figure 27:
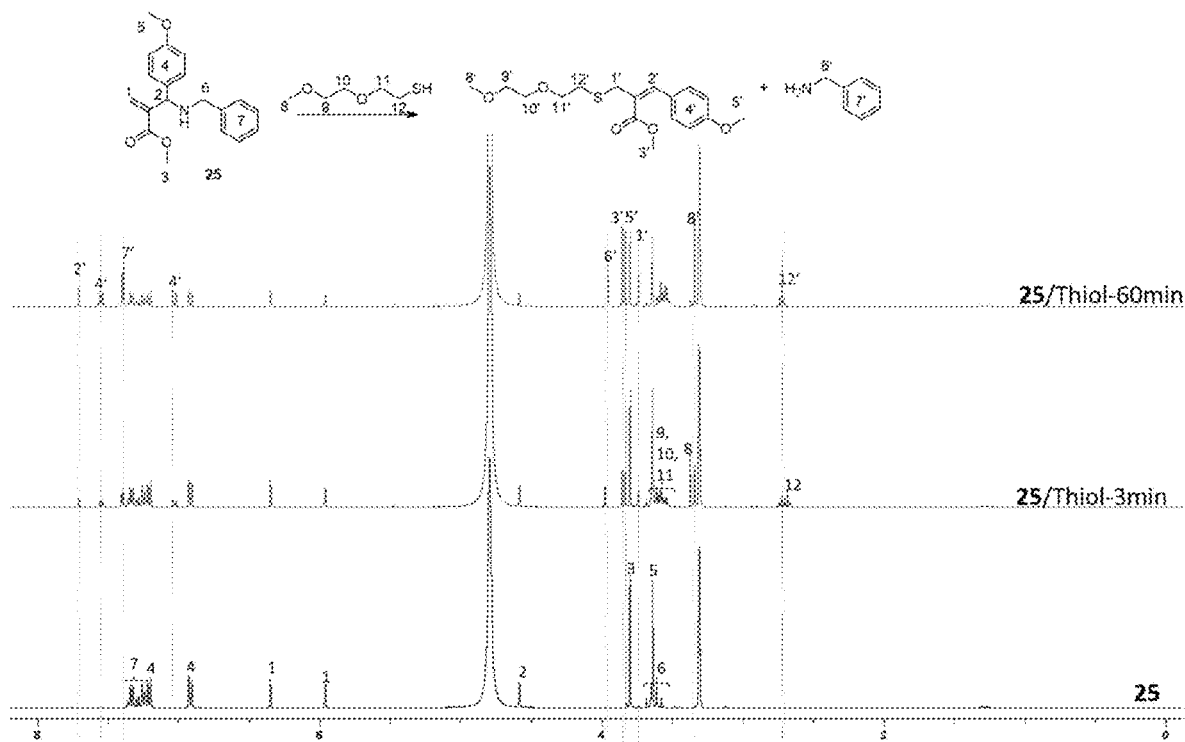
FIG. 27. Declick of amine click product, 25 is triggerable by thiol suggested by NMR. The reaction was carried out at MeOH-d4 and 50 mM pH 7.4 phosphate buffer (2:1). [25]/[DEGSH]=2. [22]: 6.67 mM.
Figure 28:
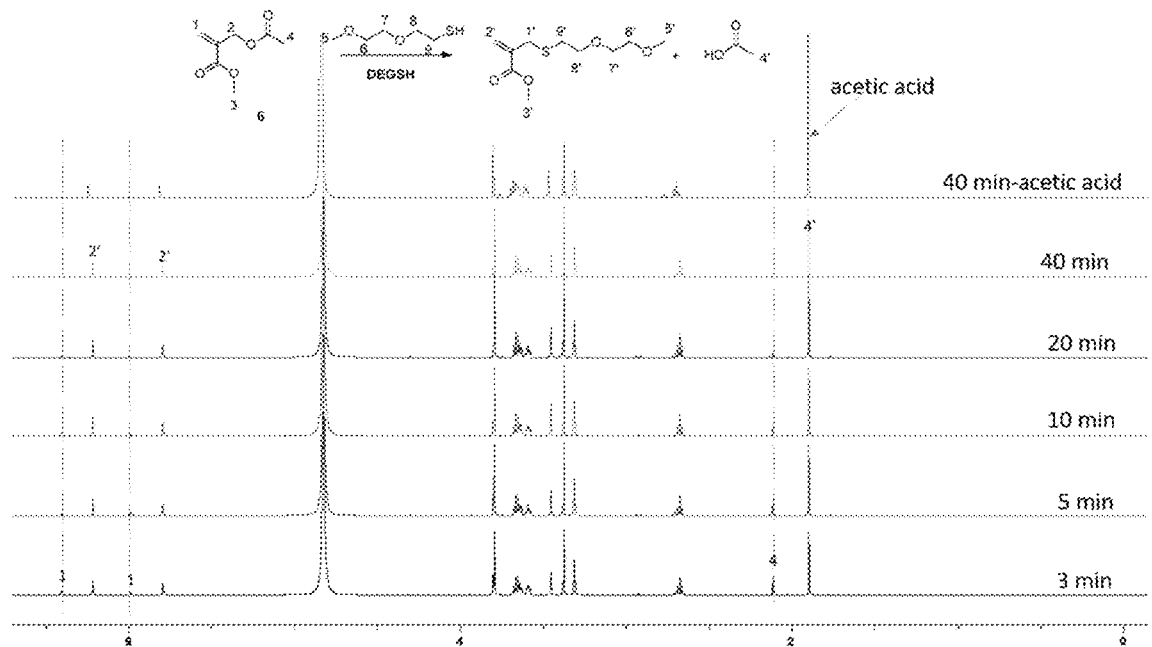
FIG. 28. Time-dependent acetic acid recovered from 6 in the presence of thiol monitored by NMR. After 40 minutes, acetic acid was added to the mixture to confirm the identity of released functionality. The reaction was carried out at MeOH-d4 and 50 mM pH 7.4 phosphate buffer (1:1). [6]/[DEGSH]=1. [6]: 10 mM. Slight shift on peaks were observed due to decreasing pH caused by addition of acetic acid. However, chemical shift of acetic acid is identical to that of released molecule confirming recovery of acetic acid.
Figure 29:
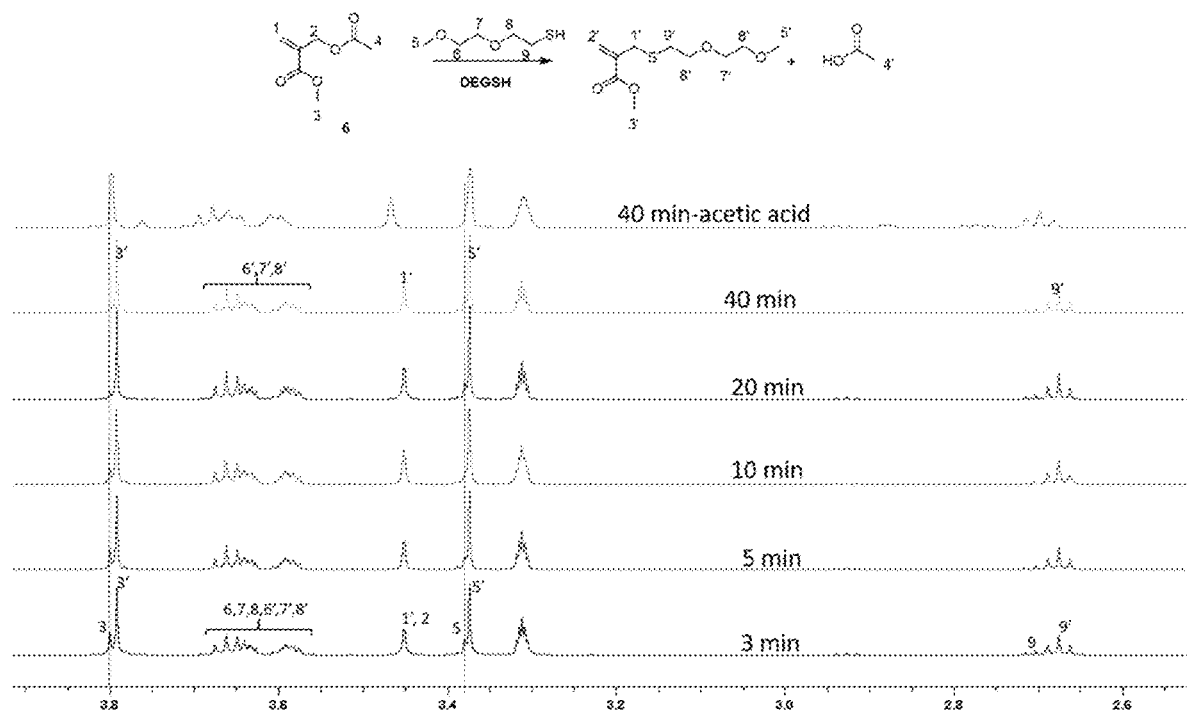
FIG. 29. Zoom-in NMR spectra of FIG. 30.
Figure 30:
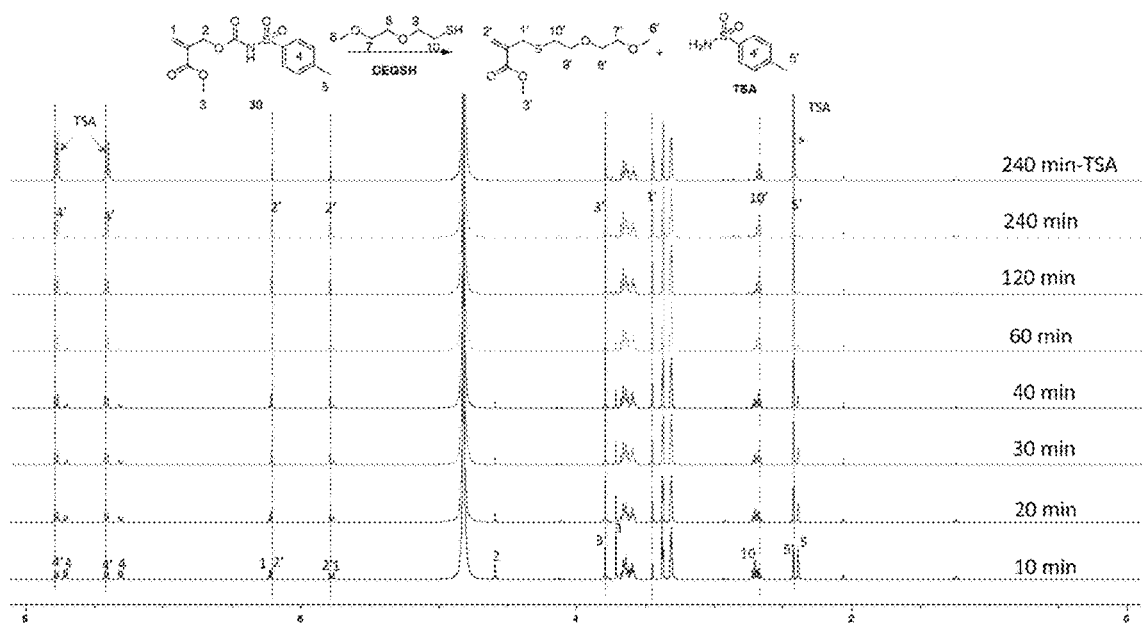
FIG. 30. Time-dependent sulfonamide recovered from 30 in the presence of thiol monitored by NMR. After 240 minutes, p-toluene sulfonamide (TSA) was added to the mixture to confirm the identity of released functionality. The reaction was carried out at MeOH-d4 and 50 mM pH 7.4 phosphate buffer (1:1). [30]/[DEGSH]=1. [30]: 10 mM.
Figure 31:
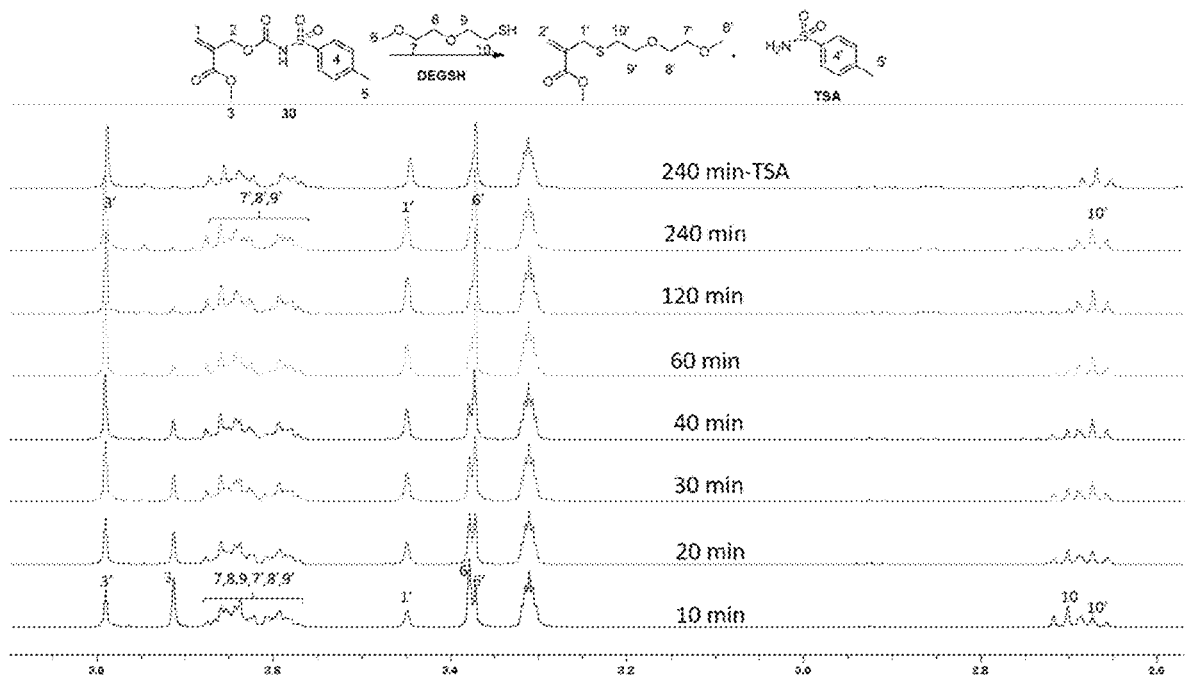
FIG. 31. Zoom-in NMR spectra of FIG. 30.
Figure 32:
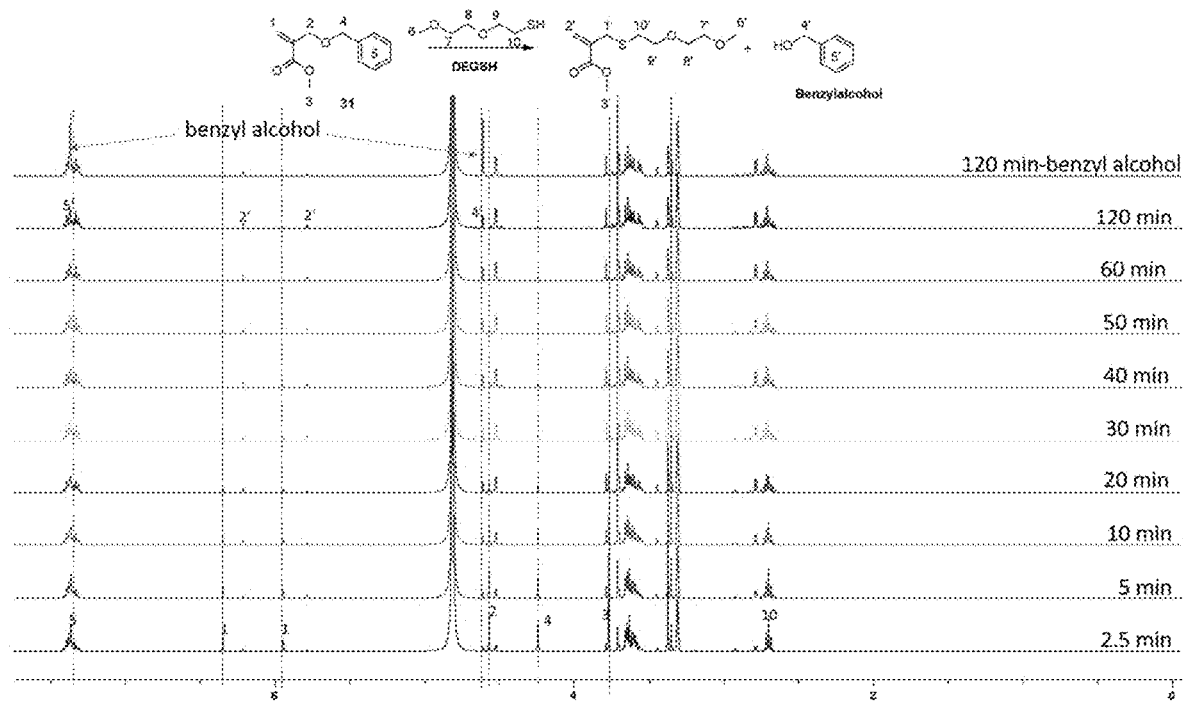
FIG. 32. Time-dependent benzyl alcohol recovered from 31 in the presence of thiol monitored by NMR. After 120 minutes, benzyl alcohol was added to the mixture to confirm the identity of released functionality. The reaction was carried out at MeOH-d4 and 50 mM pH 7.4 phosphate buffer (1:1). [31]/[DEGSH]=1. [31]: 10 mM.
Figure 33:
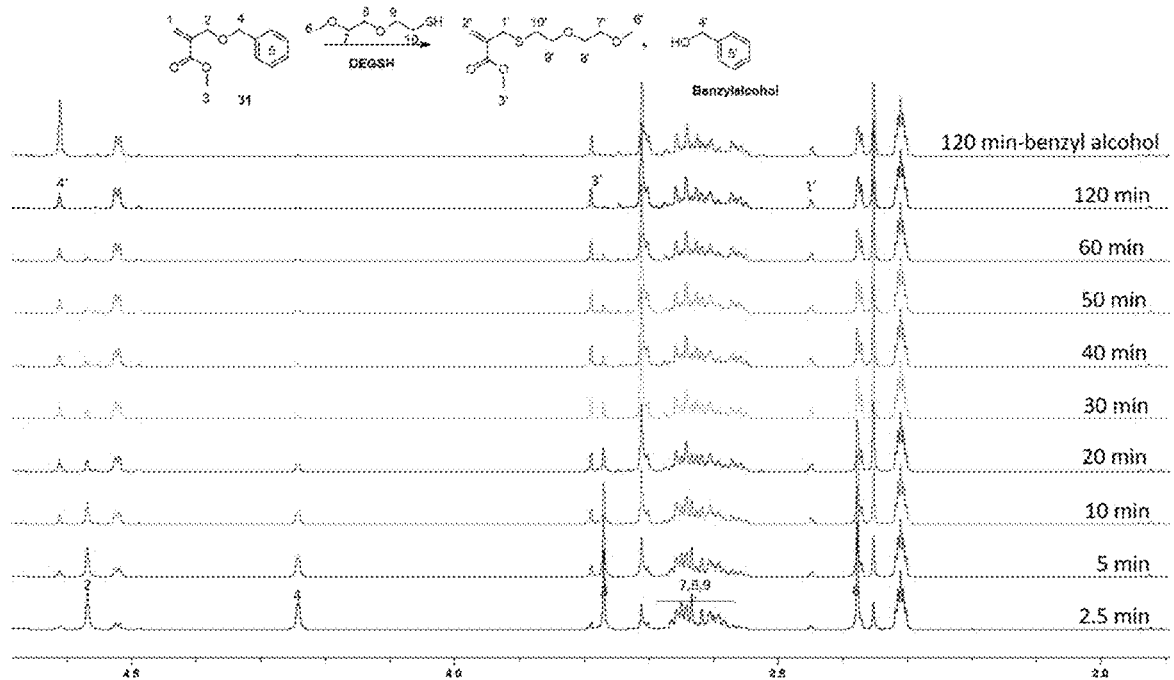
FIG. 33. Zoom-in NMR spectra of FIG. 32.
Figure 34:
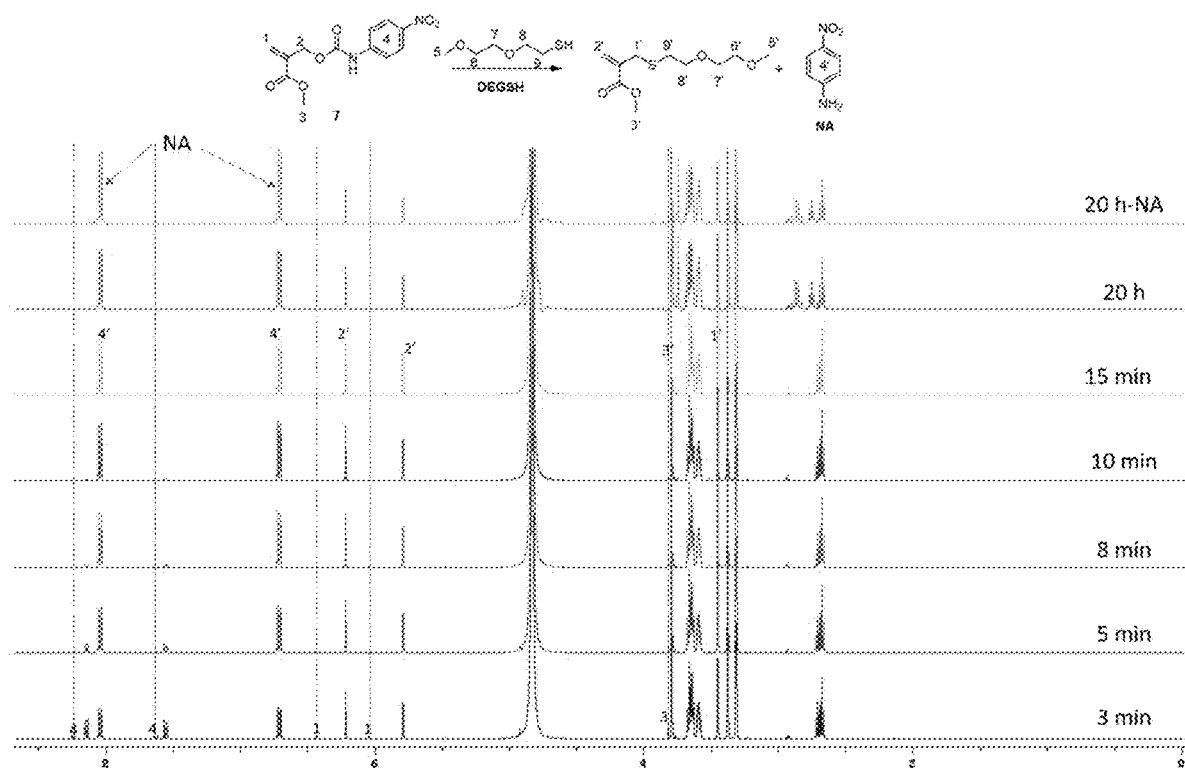
FIG. 34. Time-dependent nitroaniline (NA) recovered from 7 in the presence of thiol monitored by NMR. After reaction complete, nitroaniline was added to the mixture to confirm the identity of released functionality. The reaction was carried out at MeOH-d4 and 50 mM pH 7.4 phosphate buffer (1:1). [7]/[DEGSH]=1. [7]: 10 mM.
Figure 35:
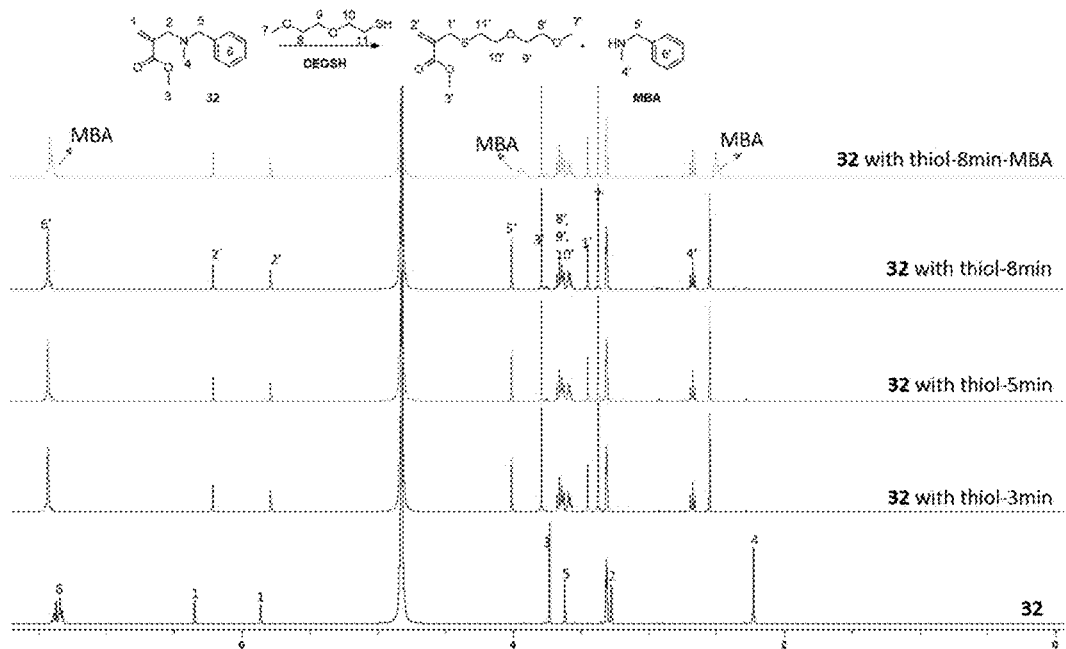
FIG. 35. Time-dependent nitroaniline N-methylbenzylamine (MBA) recovered from 32 in the presence of thiol monitored by NMR. After reaction complete, MBA was added to the mixture to confirm the identity of released functionality. The reaction was carried out at MeOH-d4 and 50 mM pH 7.4 phosphate buffer (1:1). [32]/[DEGSH]=1. [32]: 10 mM.
Figure 36:
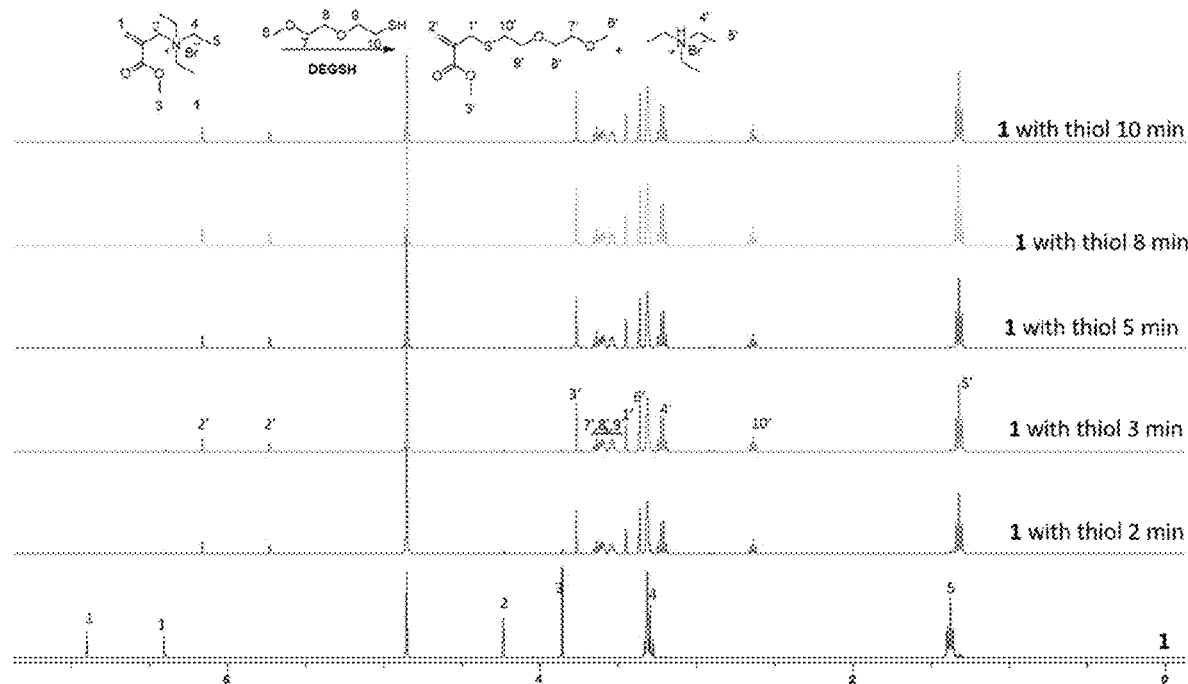
FIG. 36. Time-dependent TEA recovered from 1 in the presence of thiol monitored by NMR. The reaction was carried out at MeOH-d4 and 50 mM pH 7.4 phosphate buffer (1:1). [1]/[DEGSH]=1. [1]: 10 mM.
Figure 37:
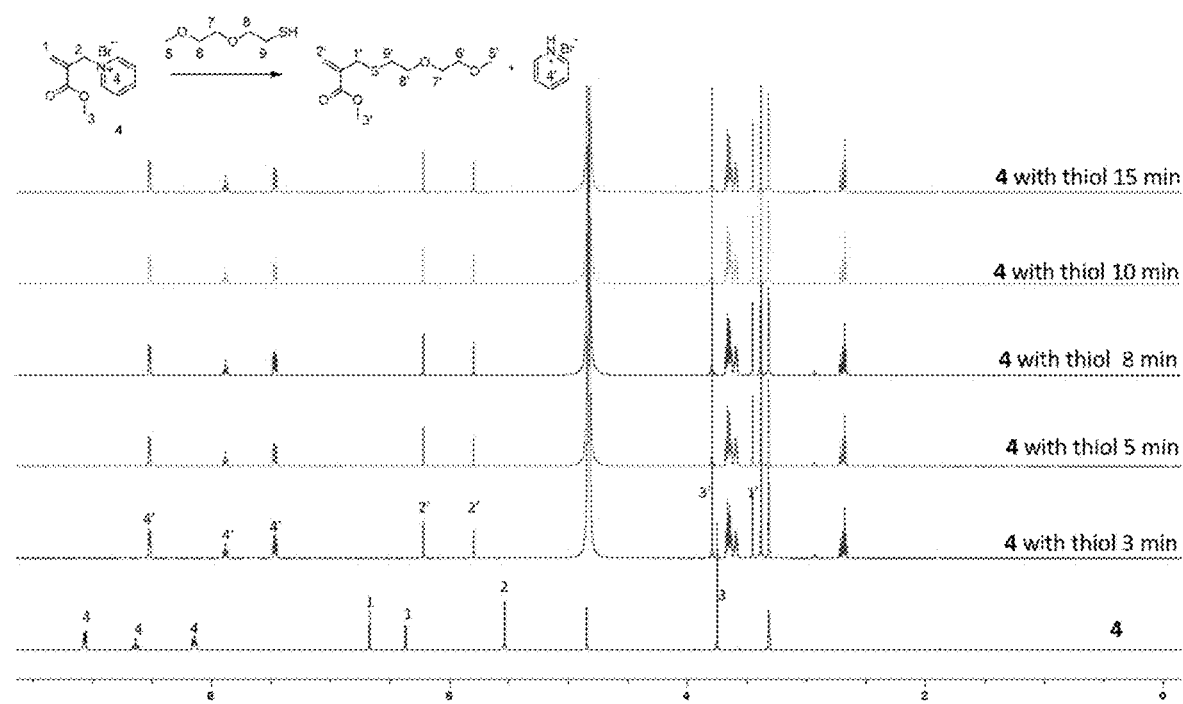
FIG. 37. Time-dependent pyridine recovered from 4 in the presence of thiol monitored by NMR. The reaction was carried out at MeOH-d4 and 50 mM pH 7.4 phosphate buffer (1:1). [4]/[DEGSH]=1. [4]: 10 mM.
Figure 38:
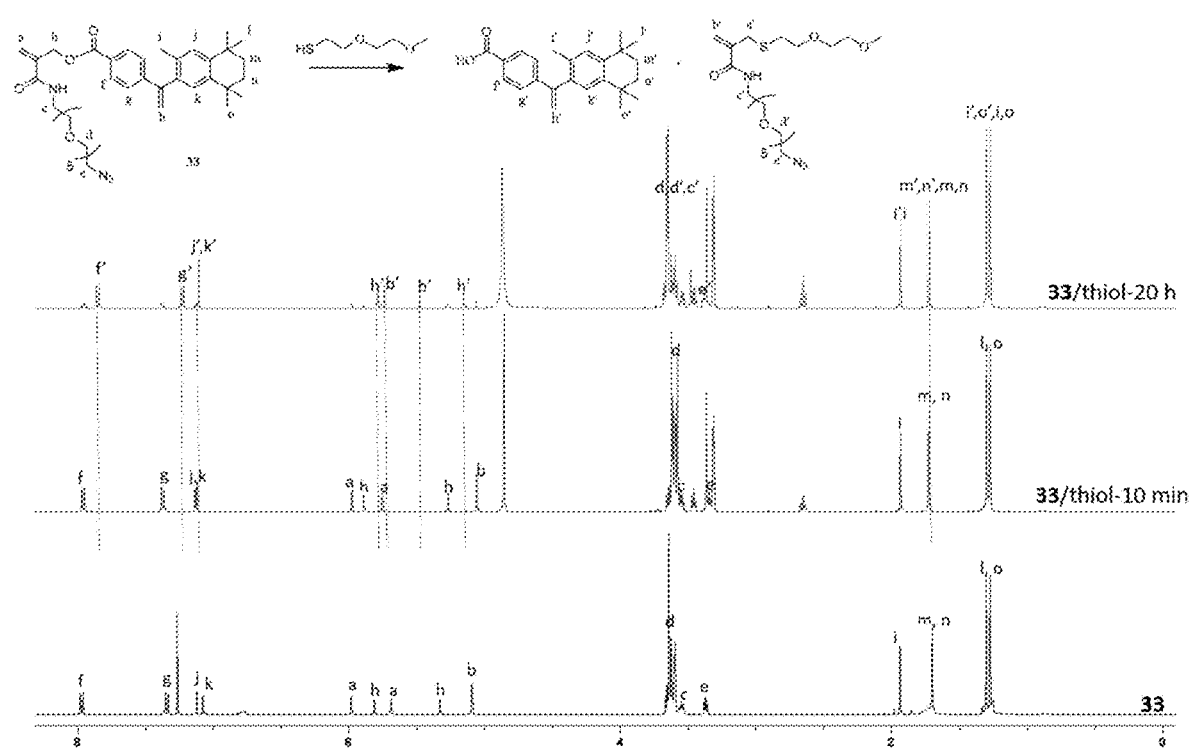
FIG. 38. Time-dependent bexarotene released from 33 triggered by thiol and monitored by NMR. The reaction was carried out at MeOH-d4 in the presence of 10 mg of solid $Na_2CO_3$. [33]/[DEGSH]=½. [4]: 10 mM.
Figure 39:
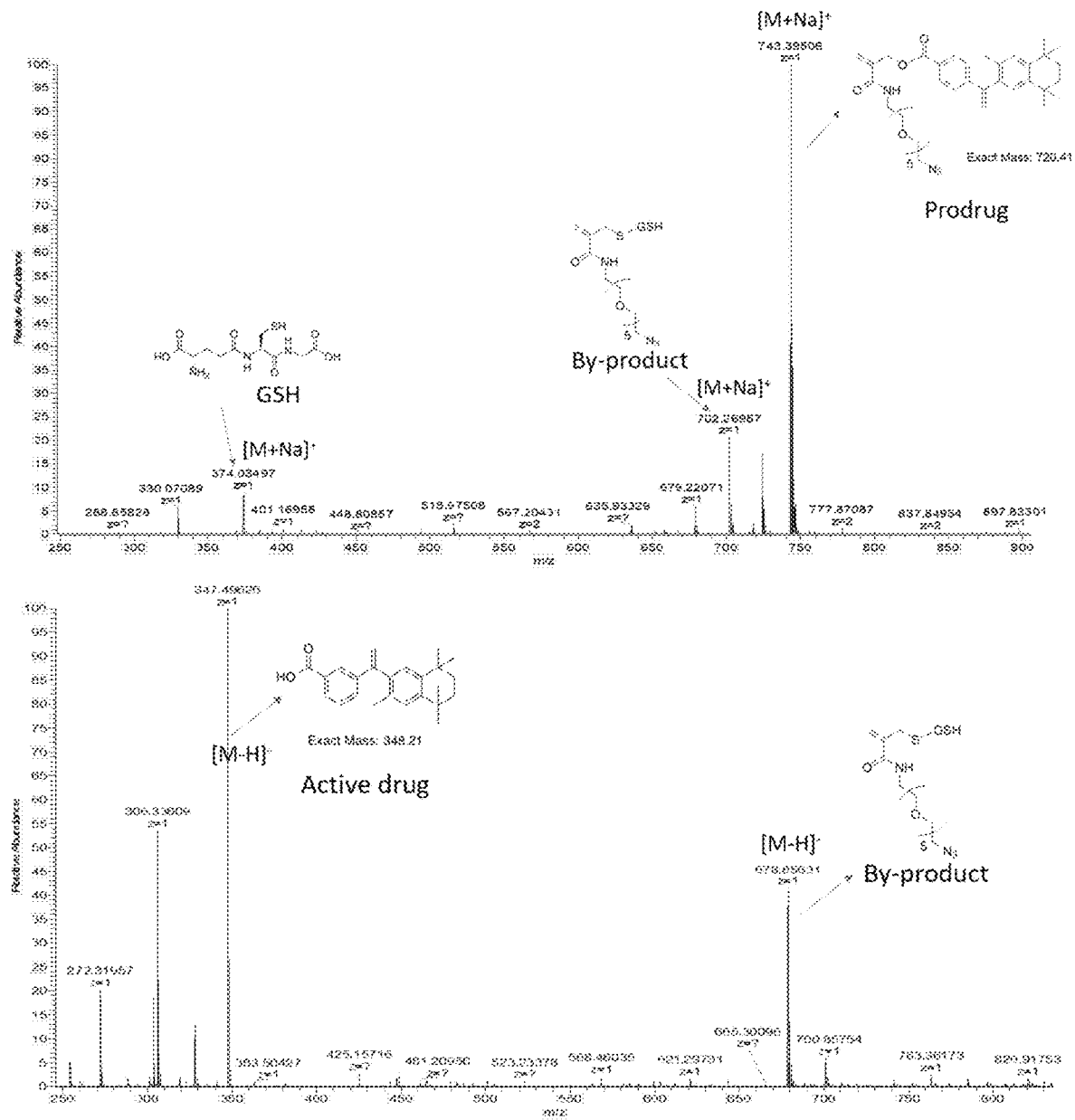
FIG. 39. Release of active drug from compound 33 triggered by Glutathione (GSH) followed by mass spectrometry. TOP: Positive mode mass spectrometry analysis; Bottom: negative mode mass spectrometry analysis. Observation of active drug signature suggests the release of drug from the prodrug. The reaction was carried out at MeOH and 50 mM pH 7.4 phosphate buffer mixture (1:1). [33]=0.5 mM, [GSH]=5 mM. The sample was analyzed by mass spec after 6-hours incubation.
Figure 40:
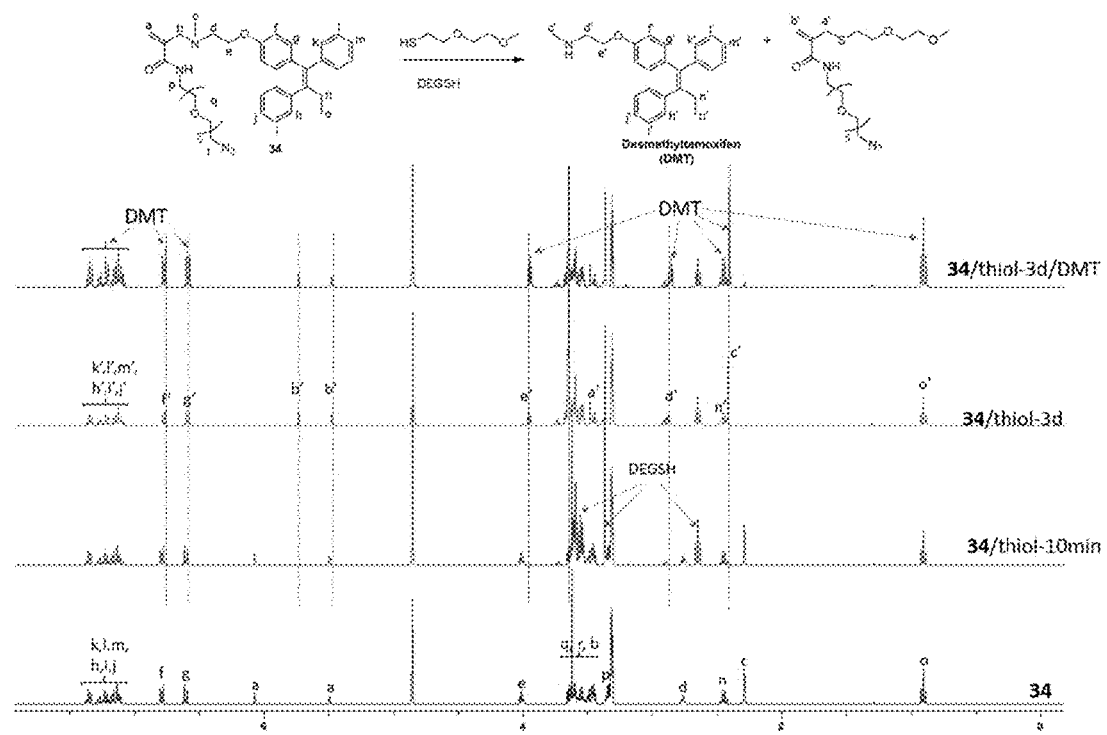
FIG. 40. Time dependent desmethyltamoxifen released from 34 in the presence of thiol monitored by NMR. After 3 days, commercial desmethyltamoxifen(DMT) was added to the reaction mixture to validate the identity of released molecule. Observation of identical chemical shifts of both desmethyltamoxifen and released molecules indicates the release of desmethyltamoxifen from 34. The reaction was carried out at MeOH-d4 and 50 mM pH 7.4 phosphate buffer (1:1). [34]/[DEGSH]=½. [4]: 5 mM.
Figure 41:
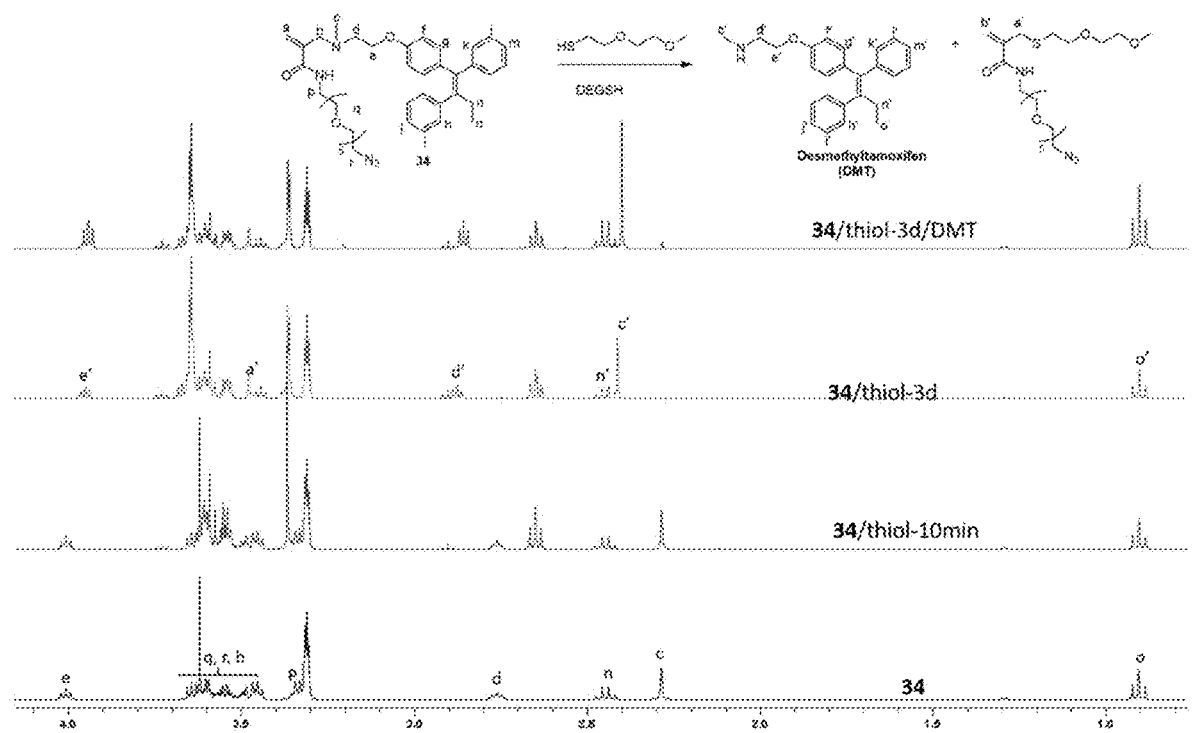
FIG. 41. Zoom-in NMR spectra of FIG. 40.

For kinetic experiments in FIG. 5G-5H, 20 equivalents of 7 were used to react with 100 µM Myo for different time periods. After labeling, the reaction mixtures were injected immediately into an LC-MS for intact protein analyses. The corresponding absorbance spectra of the reaction mixtures were also recorded on a Thermo Scientific NanoDrop 2000c Spectrophotometers (Thermo Scientific, Tewksbury, MA).

Proteolytic Digestion:

The labeled βLGb protein samples were first buffer-exchanged using 10K NMWL Amicon Ultra centrifugal filters (Millipore, Burlington, MA) with 100 mM triethylamine acetate (pH 8.0), and reconstituted with 1 M urea before enzymatic digestion. To reduce the disulfide bonds in βLGb, TCEP in water was added at a protein:TCEP molar ratio of 1:20, and the sample was incubated at room temperature for 10 min. To alkylate the reduced cysteines, iodoacetamide in water was added at a protein:iodoacetamide molar ratio of 1:80, and the sample was incubated in the dark at room temperature for 30 min. The denatured, reduced, and alkylated protein samples were then digested with trypsin at an enzyme: substrate ratio of 1:10. After 4 h of digestion at 37° C., the enzyme was separated from the mixture by centrifugation using a 10K NMWL Microcon filter (Millipore, Burlington, MA). The filtrate was then analyzed by LC-MS and LC-MS/MS.

HPLC Separation:

To quench the labeling reaction and to remove excess labeling reagents and buffer salts, a Thermo Scientific Ultimate 3000 HPLC system (Thermo Scientific, Tewksbury, MA) with an OPTI-TRAP C4 reverse phase column (1×8 mm) was used. The protein was eluted using an acetonitrile gradient that increases from 1 to 99% over 12 min at a flow rate of 0.2 mL/min. The labeled protein was collected for proteolytic digestion or intact protein MS characterization.

To analyze the Myo digests from the labeling experiments, a Thermo Scientific EASY-nLC 1000 liquid chromatography system (Thermo Scientific, Tewksbury, MA) with an Acclaim PepMap RSLC C18 reverse phase column (75 µm×15 cm, 2 µm particle size) from Thermo Scientific (Tewksbury, MA) was used. To achieve efficient separation of the proteolytic peptides, a shallow gradient was used where % B (0.1% formic acid in acetonitrile) was increased from 0% to 40% over 45 min. The column was then flushed by increasing to 95% B over 15 min. The column was then cleaned at 95% B for another 20 min. A flow rate of 300 nL/min was used throughout the run.

Mass Spectrometry:

Mass spectral analyses of the HPLC separated intact protein samples (Myo and βLGb) from the covalent labeling experiments were acquired on a Bruker AmaZon (Billerica, MA) quadrupole ion trap mass spectrometer equipped with an electrospray ionization source. The electrospray needle voltage was kept at 4 kV, and the capillary temperature was set to 250° C. Mass spectra of intact BCA protein samples were acquired on a Thermo Orbitrap Fusion Tribrid (Tewksbury, MA) mass spectrometer. The electrospray ionization source was typically operated at a needle voltage of 3800 V, and the ion transfer tube temperature was set to 325° C.

LC-MS and LC-MS/MS analyses of protein proteolytic fragments were conducted on a Thermo Orbitrap Fusion Tribrid (Tewksbury, MA) mass spectrometer. The electrospray ionization source was typically operated at a needle voltage of 2100 V, and the ion transfer tube temperature was set to 300° C. Tandem mass spectra were collected using CID with a normalized collision energy of 35%. Due to the large number of detectable peaks, an exclusion limit of 60 s was applied after five spectra had been collected for any given peak. The resolution of the Orbitrap was set to 60000.

Peptide and Modification Identification:

Raw mass spectral data files were analyzed by Thermo Proteome Discoverer 2.2 software. Spectra were searched against the corresponding protein sequence. Variable modification by certain labeling reagents of the residues and the protein N-terminus was added as a dynamic modification. Other dynamic modifications such as oxidation of methionine and carboxyamidomethylation of cysteine were also used in the searches. Trypsin enzyme cleavage was selected, and a precursor mass tolerance of 10 ppm was used. Identifications of peptides and modifications at high confidence levels were used and were manually checked in all cases.

Circular Dichroism:

Far-UV CD analyses were performed on a Jasco J-1500 spectropolarimeter. CD spectra were recorded at room temperature over a scan range of 260 to 200 nm. Protein samples were diluted to 0.1 mg/mL in 50 mM pH 7.4 phosphate buffer prior to analysis. The CD spectrometric parameters were set as follows: a scan resolution (data pitch) of 0.5 nm, a scan rate of 20 nm/min, a band width of 2 nm, and a digital integration time of 1 sec. Triplicate measurements were performed for each sample at room temperature.

Temperature dependent CD measurements were also performed for the protein samples to evaluate the thermal stability (melting temperature) of Myo before and after labeling. Ellipticity at 222 nm was recorded every 1° C. from 25° C. to 90° C. Prior to individual scans, samples were equilibrated at the new temperature for 1 min. Samples were measured in triplicates and the results were shown in average values.

Orthogonal Hydrogel Manipulation

Hydrogel formation: Compound 37 (24.48 mg, 40 µmol) was dissolved in 2 mL 50 mM sodium phosphate buffer to make stock solution with desired pH. 4 arm PEG10000-thiol (100 mg, 20 µmol) was dissolved in 2 mL 50 mM sodium phosphate buffer with desired pH to make stock solution. Then, 0.75 mL of compound 37 solution was mixed with 0.75 mL of PEG solution.

Hydrogel post-functionalization using small molecule model: Compound 38 (0.4 mg, 2.5 µmol) and compound 18 (0.665 mg, 2.5 µmol) was respectively dissolved in 2 mL of MeOH to prepare the stock solutions. Then, 1 mL of compound 38 and compound 18 solutions was mixed to form reaction solution. 50 µL of the mixed solution was then diluted with 950 µL of MeOH to form final reaction solution, the absorption and emission spectra was measured before and after UV irradiation at λ300 nm for 30 seconds.

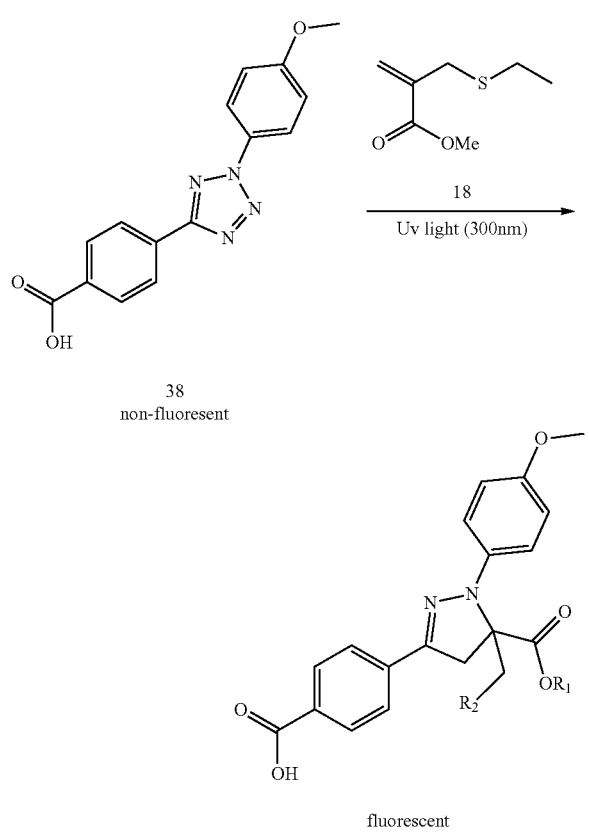

38
non-fluorescent fluorescent

Hydrogel photo-patterning: Solution of compound 37 (24.48 mg, 40 µmol) in 2 mL 50 mM pH6.8 sodium phosphate buffer and solution of 4 arm PEG10000-thiol (100 mg, 20 µmol) in 2 mL 50 mM pH6.8 sodium phosphate buffer was prepared. 0.75 mL of each solution was mixed in a petri dish and allowed to cure for 30 minutes. The petri dish was placed on the top of a hand-hold UV lamp with a patterned cover in between. Then 1 mL solution of compound 38 with concentration of 1.25 mM in MeOH was added to the middle of the dish followed by the irradiation at λ300 nm on the UV lamp. After irradiation, the hydrogel was washed with 2 mL of MeOH for 3 times to remove unreacted compound 38.

BSA loading hydrogel formation and thiol triggered BSA release. To a glass vial, 50 µL of 1.0 mg/mL FITC labelled BSA was diluted with 150 µL of 50 mM pH 7.4 sodium phosphate buffer followed by addition of 100 µL of 4-arm PEG10000 thiol (100 mg/mL). Then, 100 µL of compound 37 solution (12.24 mg/mL) in 50 mM pH 7.4 sodium phosphate buffer was added to the vial to form BSA loaded hydrogel in seconds. Two identical hydrogels were prepared using the same procedure at the same time. Then, one of hydrogel was added with 3 mL of 50 mM pH 7.4 sodium phosphate buffer, while the other one was added with 3 mL of 50 mM 2-(2-Methoxyethoxy) ethanethiol solution in 50 mM pH 7.4 sodium phosphate buffer. To monitor the release of BSA, 50 µL of liquid from each hydrogel was sampled and diluted to 1 mL and subjected for fluorescence measurement at different interval. Here, it was assumed that BSA would diffuse to liquid phase once it is released due to dissolution of hydrogel, while the BSA in intact hydrogel should be entrapped in the solid gel phase.

Hydrogel sample preparation of rheological measurement: Solution of compound 37 (24.48 mg, 40 µmol) in 2 mL 50 mM pH6.8 sodium phosphate buffer and solution of 4 arm PEG10000-thiol (100 mg, 20 µmol) in 2 mL 50 mM pH6.8 sodium phosphate buffer was prepared respectively. 0.75 mL of each solution was mixed in cylinder mode with diameter of 2.5 centimeters. Then hydrogel sample was placed in parallel plate and cut to fit the dimension of the plate.

Hydrogel dissolution for rheological measurement: 10 µL of m-PEG6-thiol (Mw 312.4) was placed and spread in parallel plate. Then hydrogel sample was placed on the top of plate and the measurement was started immediately.

Rheometry:

Measurements were performed by using the Malvern Kinexus Pro stress-controlled instrument in a small angle oscillation shear-controlled manner. A stainless parallel plate (20 mm diameter) fixture with a solvent trap was used for all experiments. Sample height was fixed at 1 mm. The shear strain amplitude and angular frequency were 1% and 10 rad/s, respectively. The storage (G') and loss moduli (G") were measured as a function of time. The transient complex viscosity profile was calculated via the IRIS software package. (Winter, et al. 2006 Rheol Acta 45, 331-338.) All experiments were conducted at 25° C.

Analysis of Protein Complexes and Higher Order Structures

Disclosed reagents were capable of being used in the context of covalent labeling/mass spectrometry (CL/MS) experiments that allowed the analysis of protein complexes and the higher order structure of proteins.

Figure 60:
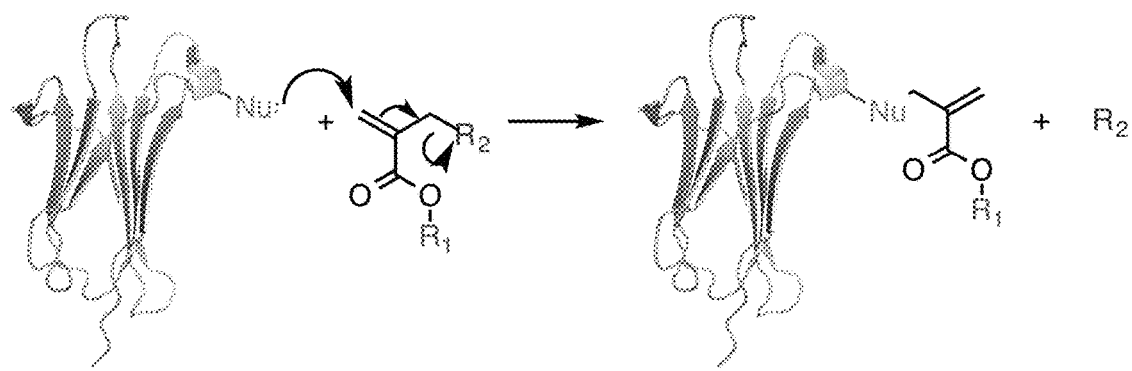
FIG. 60. Nucleophilic residues (-Nu:) on the proteins surface can react with the reagent to generate a covalently attached molecule of well-defined structure, depending on the $R_1$ functional group.

The general reaction scheme for the reagent is seen in FIG. 60.

Figure 61:
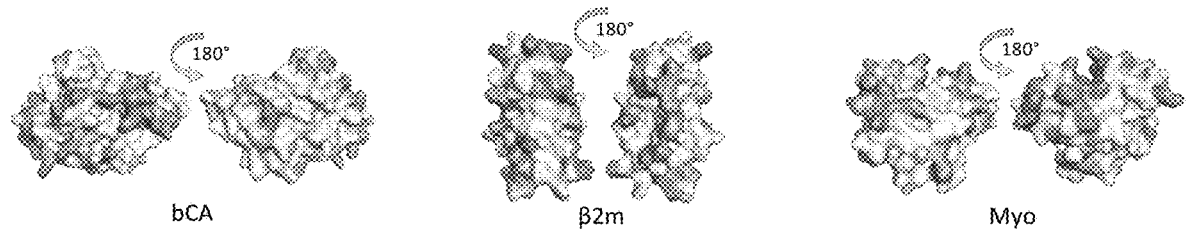
FIG. 61. Space-filling models for bovine carbonic anhydrase (bCA), β-2-microglobulin (β2m), and myoglobin (Myo). The residues labeled on each protein are indicated in orange.
Figure 62:
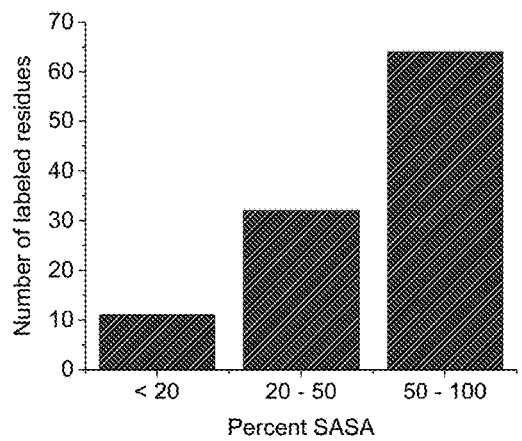
FIG. 62. Bar graph showing that most residues that are labeled by the reagent have high solvent accessible surface areas (SASA).

Upon reacting three different model proteins, including bovine carbonic anhydrase (bCA), β-2-microglobulin (β2m), and myoglobin (Myo), with a reagent that has a —$CH_3$ group as $R_1$ and a —$N(CH_2CH_3)_3^+$ group as $R_2$, we find that the types of residues that can be labeled with the new reagent include Cys, Lys, His, Arg, Ser, Thr, Tyr, Asp, Glu, Trp, Asn, and Gln. These 12 amino acid residues account for about 55% of the sequence of the average protein, indicating that this reagent can cover most of the surface of typical proteins. Example space-filling models showing the residues labeled in bCA, β2m, and Myo are shown in FIG. 61. Of the residues that are labeled, 90% are considered solvent accessible, with most having high percentages of solvent accessible surface area (SASA) (FIG. 62), making the reagent an excellent probe of protein surface topology.

Figure 63:
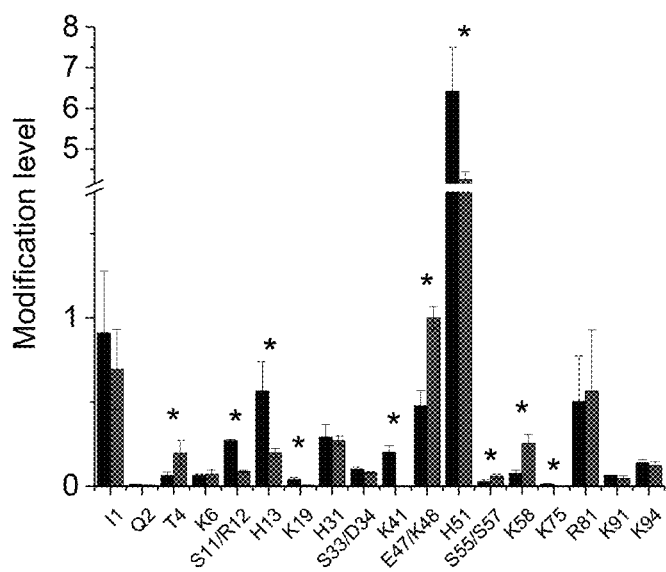
FIG. 63. Residue modification levels after reactions of the reagent with the β2m monomer and Zn-induced β2m dimer. The data with an asterisk (*) indicate a statistically significant change at a 95% confidence interval.

To demonstrate the utility of using the labeling reagent to study protein-protein complexes, we compared the reactivity of the same reagent as above (i.e. the one with $R_1$ as a —$CH_3$ group and $R_2$ as a —$N(CH_2CH_3)_3^+$ group) with the monomer of β2m and the Zn-induced dimer of β2m. A comparison of the modification levels for the monomer and dimer can be found in FIG. 63. Ten residues are found to undergo significantly different changes in modification extents, with four of them undergoing increases in reactivity and six of them undergoing decreases in reactivity.

Figure 64:
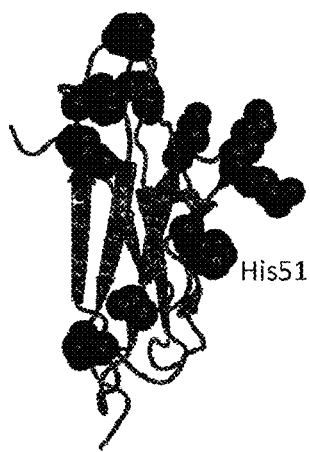
FIG. 64. Sites of modification level changes mapped onto the monomeric structure of β2m. The labeling decreases are clustered around the C-terminal 'tail' of β2m, with the exception of His51, which is the known binding site of Zn. The increases in labeling are also indicated.

The sites of these changes can be mapped onto the structure of the β2m monomer (FIG. 64). Together these results help reveal the site of the monomer-monomer interface in the dimer as involving a 'tail-to-tail' interaction of the C-terminal end of the protein.

Figure 65:
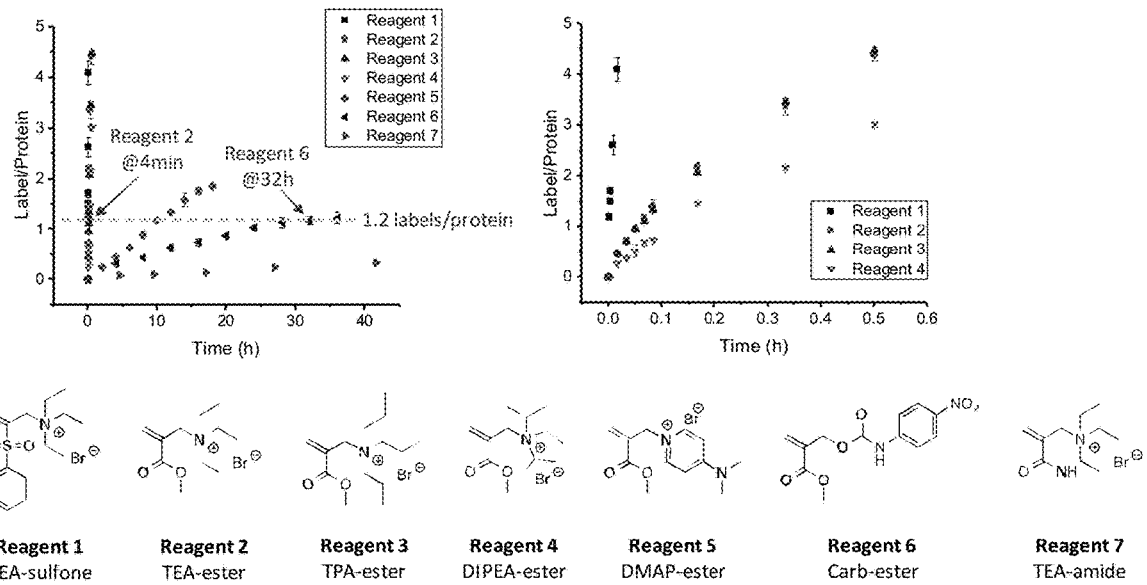
FIG. 65. Variations to the functional groups on the covalent labeling reagent can tune the reactivity. As an example in the top left graph, Reagent 2 reacts to yield 1.2 labels per protein during a 4-minute reaction, whereas Reagent 6 requires a 32 h reaction to achieve the same labeling extent.
Figure 66:
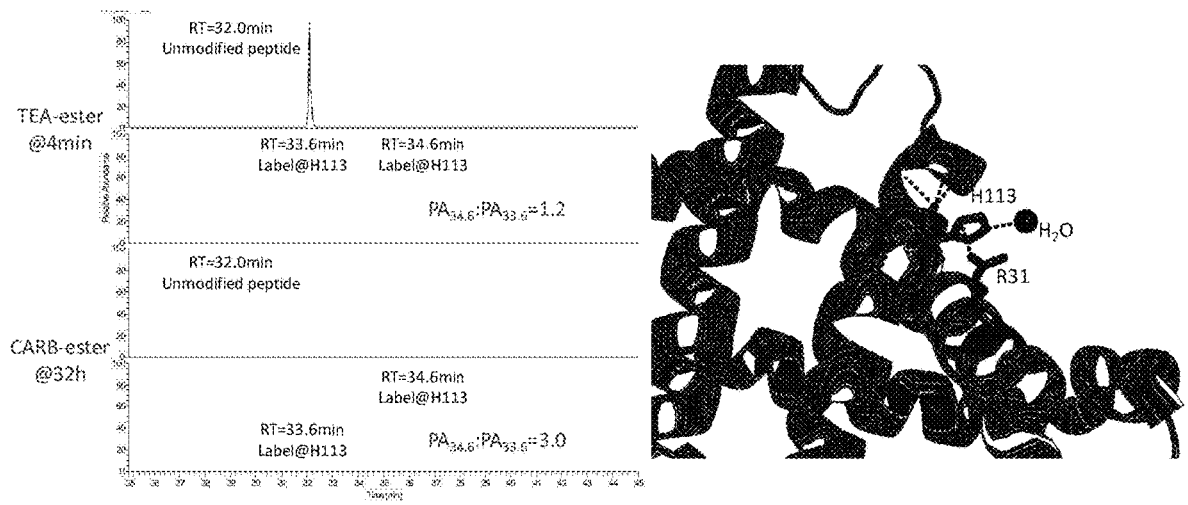
FIG. 66. Different functional groups on the reagent can also affect the covalent labeling selectivity. (Left) As an example, Reagent 2 reacts approximately equally with both nitrogens on His113 in myoglobin, whereas Reagent 6 reacts three times more extensively with one of the nitrogens on this residue. (Right) The difference in reactivity might arise from the different solvent accessibilities of the two nitrogens on His113, suggesting that the reactivity of Reagent 6 might be sensitive to subtle differences in protein structure.

Another interesting feature of the reagent indicated in FIG. 60 is that the $R_1$ group, $R_2$ group, and other functional groups in the reagent can be varied to introduce new reactivity or new capability for the covalent labeling reagent. For example, the functional groups on the reagent can be varied to control the reaction kinetics (FIG. 65). Tuning the reaction kinetics can also allow for the tuning of the labeling selectivity (FIG. 66). As an example of this latter point, the TEA-ester reagent (i.e. Reagent 2 in FIG. 65) reacts about equally with the two nitrogens on the side chain of His113 of Myo, whereas the Carb-ester reagent (i.e. Reagent 6 in FIG. 65) reacts more selectivity with only one of the nitrogens on side chain of His113. This reaction selectivity likely reflects differences in the SASAs of the two nitrogens on the His113 side chain that can be revealed only by Reagent 6.

Figure 67:
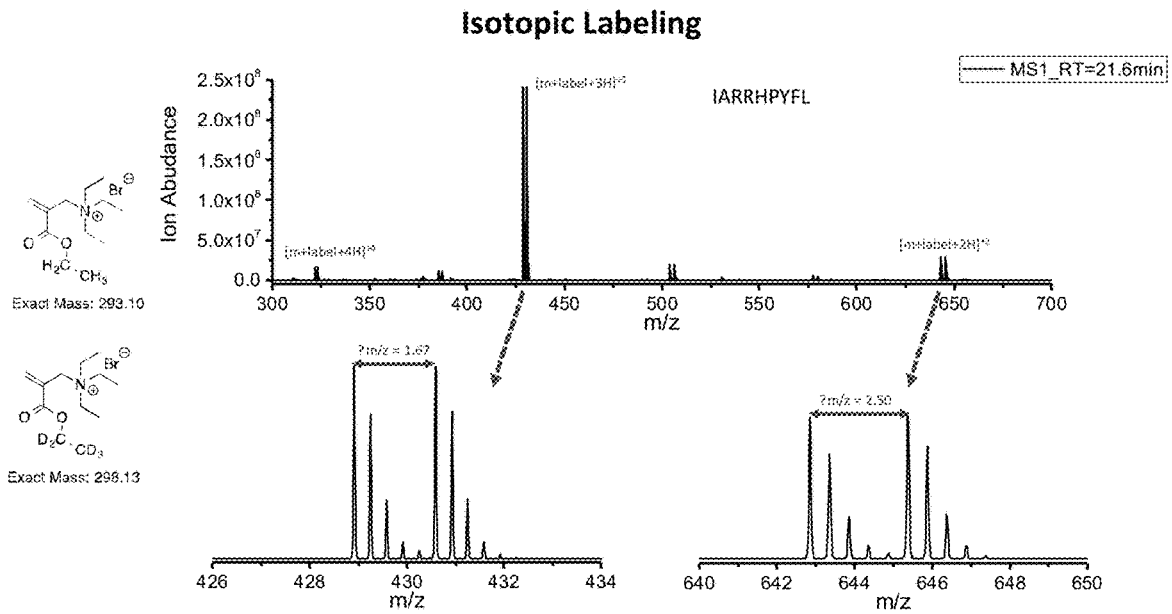
FIG. 67. Simultaneous reaction of a deuterated and non-deuterated form of the reagent with proteins can simplify identification of labeled peptides in complex protein digests. A characteristic 5 mass unit difference (Δm/z of 1.67 for a +3 ion or Δm/z of 2.5 for a +2 ion) allows the labeled peptide to be readily identified.
Figure 68:
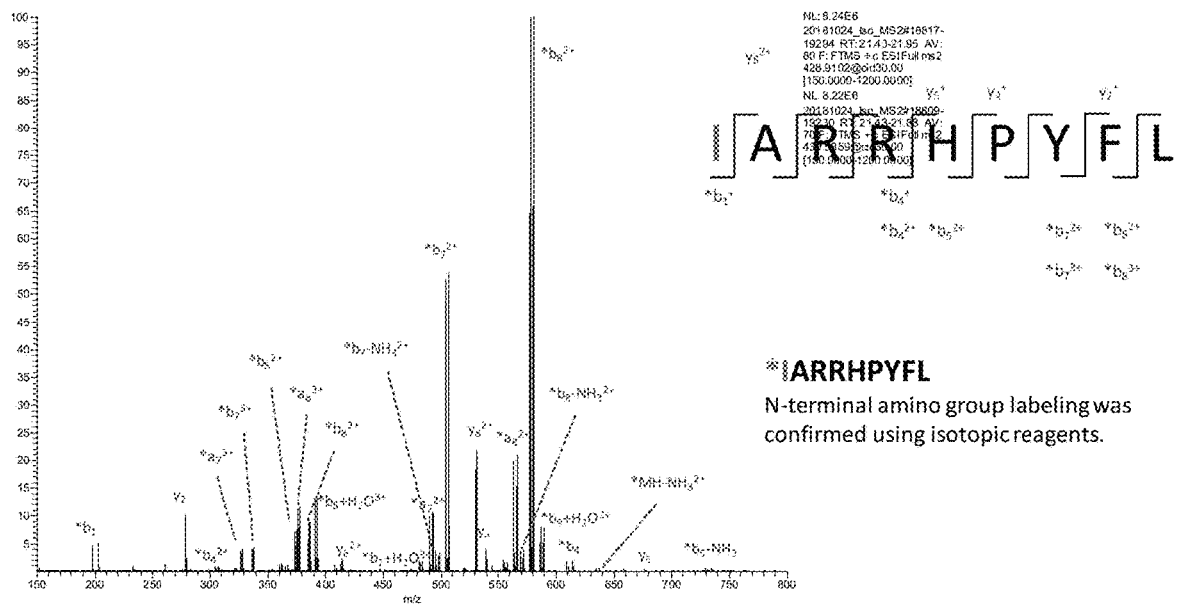
FIG. 68. Simultaneous tandem mass spectrometry of the deuterated and non-deuterated form of the covalently labeled peptide simplifies identification of the labeled residue. In this example, the N-terminus on the peptide is labeled, so all the b product ions contain a doublet of isotopic peaks, whereas all the y product ions have a single set of isotopic peaks. Figure discloses "IARRHPYFL" as SEQ ID NO: 10.

As another example, the $R_1$ group in the reagent can be isotopically enriched with deuterium instead of hydrogen on the ethyl group (FIG. 67), and if both the deuterated and normal form are simultaneously reacted with proteins, the labeled peptides after digestion can be readily identified by the characteristic multiplet of peaks that are separated by 5 mass units (FIG. 67). Moreover, simultaneous tandem MS of both covalently labeled peptides (i.e. the deuterium enriched and normal peptide) can generate tandem mass spectra that make it easier to identify.

Applicant's disclosure is described herein in preferred embodiments with reference to the figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A method for labeling a protein, comprising:
providing a protein of formula (IV) comprising a nucleophilic group (Nu) at a point of desired labeling:

R-Nu, (IV)

wherein R-Nu is R—SH or R—$NH_2$;
reacting the protein of formula (IV) with a compound of formula (V) having both a label and a reporter group:

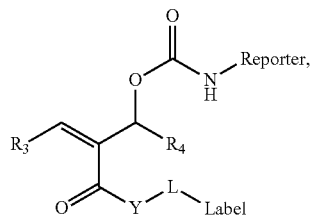
(V)

wherein
$R_3$ is H;
$R_4$ is H;
Y is O;
L is a linking group comprising —$(CH_2CH_2O)_n$—, wherein n is an integer from 1 to 10, and the reaction results in releasing of the reporter and formation of a labeled protein of formula (VI)

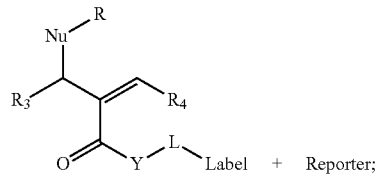
(VI)

and
detecting a signal of the reporter and/or the presence of the label to analyze or quantify the protein.

2. The method of claim 1, wherein R-Nu is R—SH.

3. The method of claim 1, wherein R-Nu is R—$NH_2$.

4. The method of claim 1, wherein the point of desired labeling is selected from cysteine, lysine, arginine, asparagine and glutamine.

5. The method of claim 1, wherein the reporter is chromogenic upon release from compound (V).

6. The method of claim 1, wherein the reporter is fluorescent.

7. The method of claim 1, wherein the point of desired labeling is cysteine.

8. The method of claim 1, wherein the point of desired labeling is lysine.

* * * * *